US012588951B2

(12) United States Patent
Casey et al.

(10) Patent No.: US 12,588,951 B2
(45) Date of Patent: Mar. 31, 2026

(54) PATIENT-SPECIFIC IMPLANT DESIGN AND MANUFACTURING SYSTEM WITH A SURGICAL IMPLANT POSITIONING MANAGER

(71) Applicant: Carlsmed, Inc., Carlsbad, CA (US)

(72) Inventors: Niall Patrick Casey, Carlsbad, CA (US); Rodrigo Junqueira Nicolau, Cardiff, CA (US); Syed Shariq Hussain, Vista, CA (US); Jeffery Pennal, San Diego, CA (US); Matthew Chen, San Diego, CA (US)

(73) Assignee: Carlsmed, Inc., Carlsbad, CA (US)

( * ) Notice: Subject to any disclaimer, the term of this patent is extended or adjusted under 35 U.S.C. 154(b) by 0 days.

(21) Appl. No.: 19/082,149

(22) Filed: Mar. 17, 2025

(65) Prior Publication Data

US 2025/0318876 A1      Oct. 16, 2025

Related U.S. Application Data

(63) Continuation of application No. 18/415,577, filed on Jan. 17, 2024, now Pat. No. 12,274,510.

(Continued)

(51) Int. Cl.
*A61B 34/10*          (2016.01)
*A61B 34/00*          (2016.01)
(Continued)

(52) U.S. Cl.
CPC ............ *A61B 34/10* (2016.02); *A61F 2/4611* (2013.01); *G06T 19/20* (2013.01); *G16H 30/20* (2018.01);
(Continued)

(58) Field of Classification Search
CPC ........ A61B 2034/102; A61B 2034/104; A61B 2034/105; A61B 2034/108;
(Continued)

(56) References Cited

U.S. PATENT DOCUMENTS

| | | | |
|---|---|---|---|
| 4,704,686 A | 11/1987 | Aldinger | |
| 6,772,026 B2 | 8/2004 | Bradbury | |

(Continued)

FOREIGN PATENT DOCUMENTS

| | | |
|---|---|---|
| CN | 104318009 A | 1/2015 |
| CN | 104353121 A | 2/2015 |

(Continued)

OTHER PUBLICATIONS

Endo, Kenji et al. "Measurement of whole spine sagittal alignment using the Slot radiography of the Sonialvision safire series clinical application." Medical Now, No. 78; Aug. 2015, 4 pages.

(Continued)

*Primary Examiner* — Sing-Wai Wu
(74) *Attorney, Agent, or Firm* — Perkins Coie LLP

(57)          ABSTRACT

Systems and methods for designing and implementing patient-specific surgical procedures and/or medical devices are disclosed. In some embodiments, a method includes receiving intra-operative data during a surgical procedure to install a patient-specific implant in a patient. The system can compare the intra-operative data to a pre-operative plan to determine whether the implant is positioned and located according to the pre-operative plan.

23 Claims, 24 Drawing Sheets

Radiograph from intra-op imaging capturing using the camera feature within the app 3D surgical plan viewed within the app with implant outline

Related U.S. Application Data

(60) Provisional application No. 63/443,676, filed on Feb. 6, 2023.

(51) Int. Cl.

| | |
|---|---|
| *A61F 2/46* | (2006.01) |
| *G06T 19/20* | (2011.01) |
| *G16H 30/20* | (2018.01) |
| *G16H 30/40* | (2018.01) |
| *A61B 90/00* | (2016.01) |

(52) U.S. Cl.
CPC ........ *G16H 30/40* (2018.01); *A61B 2034/102* (2016.02); *A61B 2034/104* (2016.02); *A61B 2034/105* (2016.02); *A61B 2034/108* (2016.02); *A61B 2034/252* (2016.02); *A61B 2034/256* (2016.02); *A61B 2090/364* (2016.02); *A61F 2002/4633* (2013.01); *G06T 2219/2004* (2013.01)

(58) Field of Classification Search
CPC ........ A61B 2034/252; A61B 2034/256; A61B 2090/364; A61B 34/10; A61F 2/4611; A61F 2002/4633; G06T 19/20; G06T 2219/2004; G16H 30/20; G16H 30/40
See application file for complete search history.

(56) References Cited

U.S. PATENT DOCUMENTS

| | | | |
|---|---|---|---|
| 7,174,282 | B2 | 2/2007 | Hollister et al. |
| 7,799,077 | B2 | 9/2010 | Lang |
| 8,246,680 | B2 | 8/2012 | Betz |
| 8,265,949 | B2 | 9/2012 | Haddad |
| 8,275,594 | B2 | 9/2012 | Lin |
| 8,337,507 | B2 | 12/2012 | Lang |
| 8,394,142 | B2 | 3/2013 | Bertagnoli |
| 8,457,930 | B2 | 6/2013 | Shroeder |
| 8,556,983 | B2 | 10/2013 | Bojarski et al. |
| 8,644,568 | B1 | 2/2014 | Hoffman |
| 8,735,773 | B2 | 5/2014 | Lang |
| 8,758,357 | B2 | 6/2014 | Frey |
| 8,775,133 | B2 | 7/2014 | Schroeder |
| 8,781,557 | B2 | 7/2014 | Dean |
| 8,843,229 | B2 | 9/2014 | Vanasse |
| 8,855,389 | B1 | 10/2014 | Hoffman |
| 8,870,889 | B2 | 10/2014 | Frey |
| 9,198,678 | B2 | 12/2015 | Frey et al. |
| 9,208,558 | B2 | 12/2015 | Dean |
| 9,445,907 | B2 | 9/2016 | Meridew |
| 9,542,525 | B2 | 1/2017 | Arisoy et al. |
| 9,642,633 | B2 | 5/2017 | Frey et al. |
| 9,693,831 | B2 | 7/2017 | Mosnier et al. |
| 9,707,058 | B2 | 7/2017 | Bassett |
| 9,775,680 | B2 | 10/2017 | Bojarski et al. |
| 9,782,228 | B2 | 10/2017 | Mosnier et al. |
| 9,993,341 | B2 | 6/2018 | Vanasse |
| 10,292,770 | B2 | 5/2019 | Ryan |
| 10,390,958 | B2 | 8/2019 | Maclennan |
| 10,646,258 | B2 | 5/2020 | Donner et al. |
| 10,937,237 | B1 * | 3/2021 | Kim ......................... G06T 7/75 |
| 11,112,770 | B2 | 9/2021 | Roh et al. |
| 11,185,369 | B2 | 11/2021 | Ryan |
| 11,376,076 | B2 | 7/2022 | Casey et al. |
| 11,793,577 | B1 | 10/2023 | Casey et al. |
| 12,232,885 | B2 | 2/2025 | Casey et al. |
| 2007/0270680 | A1 | 11/2007 | Sheffer et al. |
| 2015/0150523 | A1 | 6/2015 | Sirpad |
| 2016/0045317 | A1 | 2/2016 | Lang |
| 2017/0135706 | A1 | 5/2017 | Frey et al. |
| 2017/0143831 | A1 | 5/2017 | Varanasi et al. |
| 2017/0220740 | A1 | 8/2017 | D'Urso |
| 2018/0303552 | A1 | 10/2018 | Ryan |
| 2019/0175277 | A1 | 6/2019 | Chav |
| 2019/0274735 | A1 | 9/2019 | Drozd et al. |
| 2020/0078180 | A1 | 3/2020 | Casey et al. |
| 2020/0261156 | A1 | 8/2020 | Schmidt |
| 2021/0259776 | A1 | 8/2021 | Upadrasta et al. |
| 2022/0013211 | A1 | 1/2022 | Steinberg et al. |
| 2022/0031396 | A1 | 2/2022 | Ryan et al. |
| 2022/0211507 | A1 | 7/2022 | Simoes |
| 2023/0016297 | A1 * | 1/2023 | Gillman ................ G16H 20/40 |
| 2023/0104580 | A1 | 4/2023 | Roh et al. |
| 2024/0115398 | A1 | 4/2024 | Frey |
| 2024/0252248 | A1 | 8/2024 | Casey et al. |
| 2024/0261029 | A1 | 8/2024 | Casey et al. |

FOREIGN PATENT DOCUMENTS

| | | |
|---|---|---|
| CN | 204468348 U | 7/2015 |
| CN | 105796214 A | 7/2016 |
| CN | 110575289 A | 12/2019 |
| EP | 3120796 A1 | 1/2017 |
| WO | 2014180972 A2 | 11/2014 |
| WO | 2016172694 A1 | 10/2016 |
| WO | 2019112917 A1 | 6/2019 |
| WO | 2022124916 A1 | 6/2022 |
| WO | 2024064299 A1 | 3/2024 |

OTHER PUBLICATIONS

International Search Report and Written Opinion mailed Feb. 8, 2024 in International Patent Application No. PCT/US23/33896, 17 pages.

International Search Report and Written Opinion mailed May 30, 2024 in International Patent Application No. PCT/US24/10943, 19 pages.

International Search Report and Written Opinion mailed Jul. 5, 2024 in International Patent Application No. PCT/US24/14514, 14 pages.

Materialise Mimics, "Efficiently turn scans into accurate virtual 3D models," Retrieved on Nov. 1, 2019 at www. materialize.com/en/ medical/software/mimics, 1 page.

Pimenta, Dr. Luiz, "Current Surgical Strategies to Restore Proper Sagittal Alignment," Journal of Spine 2015, vol. 4, Issue 4, 2 pages.

Pyo et al., "Methods Used to Assess the 3D Accuracy of Dental Implant Positions in Computer- Guided Implant: A Review.," Jour. Of Clin. Med., vol. 8(1): 54, Issue 07, Jan. 2019, 12 pages.

* cited by examiner

400

| PATIENT | |
|---|---|
| PT. ID | JDoe |
| Metric | Value |
| Age | 58 |
| Gender | M |
| BMI | 32 |
| LL | 40 |
| PI | 55 |
| Levels | 4 |

620

| Obtain images of patient | 622 |

| Calculate measurements of the implant placement | 624 |

| Display measurements on user interface | 626 |

| Notify user of comparison results of the pre-operative plan to intra-operative data | 628 |

700
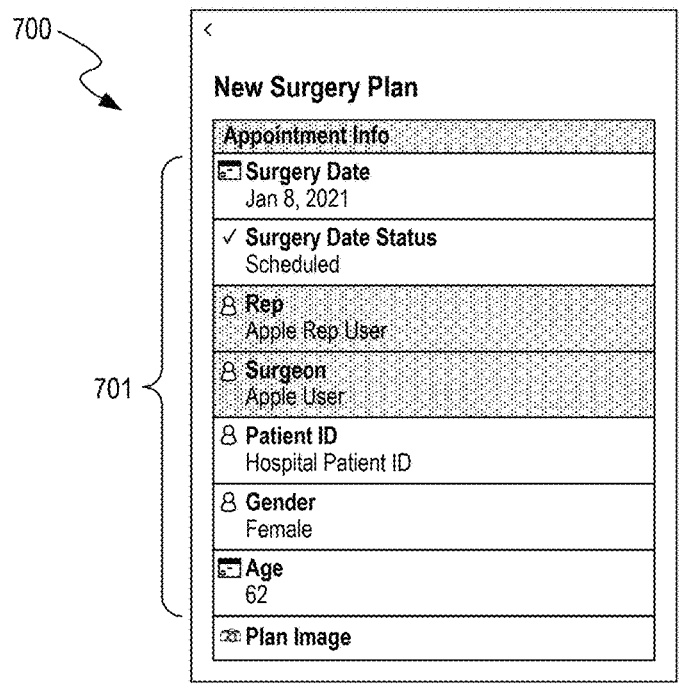
FIG. 7A
700
700
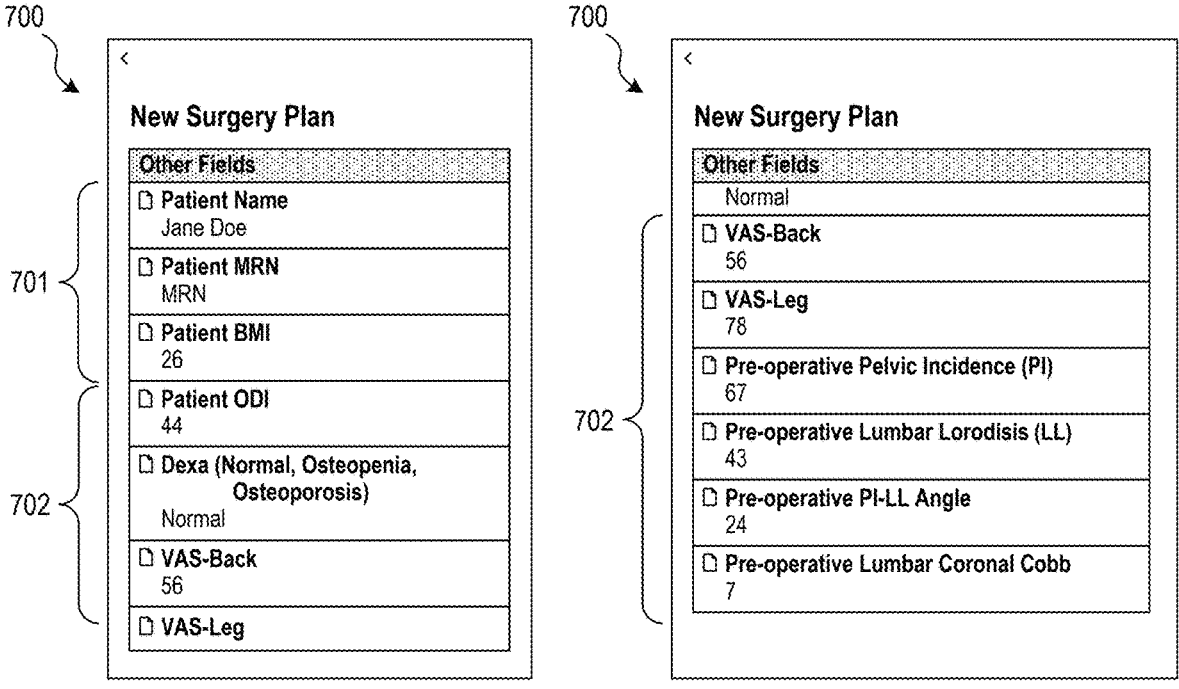
FIG. 7B                 FIG. 7C

1060

1ˢᵗ Stage <u>1062</u>  ——————

2ⁿᵈ Stage <u>1064</u> — — — — — — —

3D surgical plan viewed within the app with implant outline

1084

1086

Radiograph from intra-op imaging capturing using the camera feature within the app

1082

1088

PATIENT-SPECIFIC IMPLANT DESIGN AND MANUFACTURING SYSTEM WITH A SURGICAL IMPLANT POSITIONING MANAGER

CROSS REFERENCE TO RELATED APPLICATIONS

This application is a continuation of U.S. application Ser. No. 18/415,577, filed Jan. 17, 2024, which claims priority to and the benefit of U.S. Provisional Patent Application No. 63/443,676, filed Feb. 6, 2023, the contents of which are incorporated herein by reference in their entireties.

TECHNICAL FIELD

The present disclosure is generally related to designing, manufacturing, and implementing medical care, and more particularly to systems and methods for monitoring intra-operative positioning for patient-specific surgical procedures and/or medical devices.

BACKGROUND

Numerous types of data associated with patient treatments and surgical interventions are available. To determine treatment protocols for a patient, physicians often rely on a subset of patient data available via the patient's medical record and historical outcome data. However, the amount of patient data and historical data may be limited, and the available data may not be correlated or relevant to the particular patient to be treated. Conventional technologies in the field of orthopedics may lack the capability to draw upon large data sets to generate and optimize patient-specific treatments (e.g., surgical interventions and/or implant designs) to achieve favorable treatment outcomes. Unfortunately, during a patient-specific treatments there is no current way to actively monitor and assess if the treatment is proceeding as planned.

BRIEF DESCRIPTION OF THE DRAWINGS

The accompanying drawings illustrate various embodiments of systems, methods, and embodiments of various other aspects of the disclosure. Any person with ordinary skill in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 4A illustrates a patient data set. FIG. 4B illustrates a plurality of reference patient data sets. FIG. 4C illustrates similarity scores and outcome scores for the reference patient data sets of FIG. 4B.

FIGS. 7A-7D illustrates an exemplary patient data set that may be used and/or generated in connection with the methods described herein, according to an embodiment.

FIGS. 9A-1-9B-2 illustrate an exemplary virtual model of a patient's spine in a pre-operative anatomical configuration and a corrected anatomical configuration. More specifically, FIGS. 9A-1 and 9A-2 illustrates the pre-operative anatomical configuration of the patient, FIGS. 9B-1 and 9B-2 illustrates the corrected anatomical configuration.

DETAILED DESCRIPTION

Figure 1:
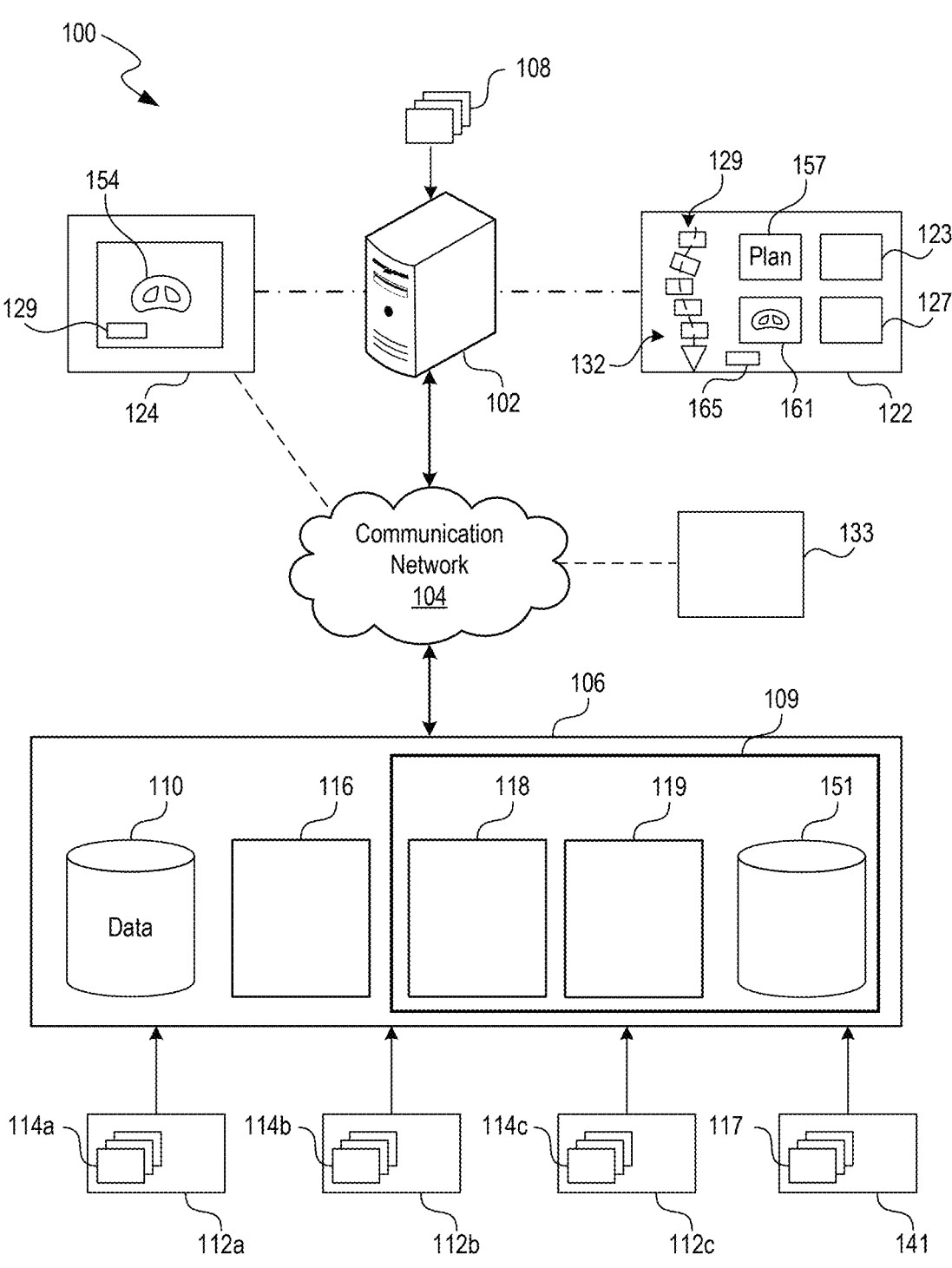
FIG. 1 is a network connection diagram illustrating a system for providing patient-specific medical care, according to an embodiment.

The present technology is directed to systems and methods for monitoring surgical procedures based on pre-operatively generated surgical plans. The present technology can provide confirmation of intra-operative positioning of surgical instruments, surgical implants, and/or anatomic elements (e.g., intra-operative pathology, anatomical configurations, etc.) based on pre-operative plans, user input, or other data sources. The present technology can display, via a display on a device, a patient-specific interactive surgical plan generated by a surgical planning platform. The patient-specific interactive surgical plan can include a user input element for modifying and/or approving the interactive surgical plan, inputting operative data (e.g., physician notes, observations, etc.), etc. In some cases, the interactive surgical plan includes a viewable planned intra-operative pathology for the patient. The system can overlay intra-operative image(s) over pre-operatively planned image(s) to confirm that the positioning of a patient-specific implant is located and positioned according to the surgical plan. The system can confirm the placement of the implant during a surgical procedure using, for example, images (e.g., real-time images, radiographic images, fluoroscopy, etc.), direct visualization, and/or other data. The intra-operative images can show, for example, the position of implants relative to anatomical elements. The planned images can be generated based on one or more patient images, virtual models of the patient's anatomy, images from surgical plans, etc. The intra-operative images of the actual anatomy can be synchronized or keyed to the planned images to determine whether surgical instruments, implants, or other image features are at planned locations. In some embodiments, the system can provide a positioning score (e.g., position score for current position of the implant or group of implants) to provide a likelihood of reaching a targeted outcome. The user can reposition implant(s) any number of times until achieving a suitable score. The system to provide real-time feedback (e.g., post-operative predicted outcomes) based on real-time imaging data to ensure proper positioning. Each time the implant is moved, the system can generate new simulations to output feedback. The predictions can be used to confirm that the implant position will provide the desired outcome.

Patient-specific implants can be designed to be placed in a singular, specific location of a patient. In some instances, it is difficult to assess if the implant reached the intended/planned position during a surgical procedure to install the patient-specific implant. The system can use one or more cameras or imaging devices (e.g., MRI, X-Ray, CT scan, direct visualization, optical visualization, machine visualization, etc.) to capture intra-operative images. The system can virtually overlay images (e.g., intra-operative images on to planned or target images (or vice-versa)) to determine whether the implant is positioned according to the pre-op surgical plan. The planned or target images can be generated from virtual models representing the patient's anatomy. The virtual models can be three dimensional models with anatomical features in, for example, targeted or planned intra-operative positions. In some embodiments, the system can overlay images showing planned positions of instrument and actual intra-operative positions of instruments. The user can view the comparison to reposition instruments to facilitate insertion and/or delivery of implants. If instruments, implants, or other surgical devices are mispositioned, the system can notify the user whether the mispositioning will likely affect the patient outcome. The system can perform simulations to generate predicted mis-positioning outcomes (e.g., biomechanics of joints, anatomical configurations, pathologies, pain outcomes, etc.). If the predicted mis-positioning outcome is acceptable, the user may leave the instrument, implants, or other devices at the new positions. This allows the user to intra-operatively evaluate and alter the surgical procedure to achieve desired outcomes.

Confirming or aiding in optimal implant positioning is helpful for personalized implant solutions, as the implants are designed to reside and fit in one particular location. If the implant is not positioned in the particular location, it may result in a less-than-optimal fit, undesired outcome, and/or impaired function for the patient. In some embodiments, planned or target images can be overlayed onto continuous imaging (e.g., fluoroscopic imaging) to provide continuous, real-time guidance. An operator can reposition fluoroscopic imaging equipment to facilitate alignment of the planned or target images and the fluoroscopic imaging. In some embodiments, planned or target images can include visual indicators (e.g., annotation, boxes, templates for implants, templates for instruments, etc.) to facilitate alignment and/or positioning. The system can scale and manipulate the planned or target images to achieve a best fit with the fluoroscopic imaging, or other type of imaging.

The systems and methods can update a plan for medical treatment. In some embodiments, image data can include a depiction of a native anatomical configuration of anatomical elements. The method can then include identifying one or more ancillary, alternative, additional, and/or unconventional steps and/or procedures (referred to collectively as "additional steps" or "ancillary steps") for adjusting intra-operative mobility of anatomical elements (e.g., vertebrae of the patient's spine in spinal procedures, joint elements in joint repair procedures, etc.) to achieve the corrected anatomical configuration. The additional steps can include, surgically altering an implantation site, manipulating soft tissue or anatomical elements, etc. In some embodiments, additional steps can be displayed to a user for modification and/or approval. In some embodiments, the method can compare pre-operative planned anatomical configurations to intra-operative image data collected during a surgical procedure. This allows a user to visually identify differences between planned and actual positions. The additional steps can be designed to limit, minimize, or eliminate one or more of those differences. For example, the additional steps can include intra-operatively generated steps based on the intra-operative data to facilitate accurate positioning of implants at targeted sites. In spine-related surgical procedures, additional steps can include manipulation of tissue. For example, soft tissue surrounding the patient's spine (e.g., ligaments, muscles, nerves, discs, and the like), vertebrae (e.g., vertebrae outside of the target vertebrae), and other anatomical features can be manipulated, such as enlarge access pass to implantation sites, adjust the size of the implantation sites, or otherwise position anatomical elements to facilitate the implantation process. Examples of the additional steps can include severing a ligament along the subject's spine, removing at least a portion of an annulus of intervertebral disc, resecting cartilage along the spine; performing an additional decompression procedure, an osteotomy, and/or facetectomy; interrupting an unintended (or undesired) bone fusion; and/or addressing malformities and/or irregularities in a bone (e.g., addressing fibrous dysplasia). Next, the method can include pre-operatively and/or intra-operatively generating a surgical plan and/or series of surgical steps, which include at least one of the additional surgical steps.

The system can compare planned positions to actual/intra-operative positions. The positions can be of instruments, anatomical elements, tissues, implants, or other positions disclosed herein. Additional or alternative surgical steps can be generated based on the comparisons using, for example, machine-learning platforms. In some embodiments, the comparisons can be displayed to a user to visually review planned positions to the actual positions. The method can generate one or more alerts if the planned positions deviate from the actual positions by, for example, a threshold. The threshold can be based on predicted adverse outcomes, user input, or the like. In some embodiments, the user can preoperatively identify an envelope or boundary for an implantation site. The system can determine whether the implant is positioned within the envelope or boundary. The system can also predict the post-operative position of the implant after the patient recovers from surgery. For example, the system can predict the position of the implant in various loading conditions when the user performs tasks. Based on these predictions, the system can determine whether the implant will remain within the boundary. If the system predicts that the implant will be positioned outside the boundary, the system can modify a surgical plan to position the implant at another site to achieve the desired outcome post-operatively. In some embodiments, the threshold may be a percentage of the implant (e.g., by volume) located within the boundary, predicted mobility score, predicted quality of life outcome, or combinations thereof (e.g., a composite score threshold).

The system can provide information for non-planned positions of implants. The system can identify the current position of the implant being different than the planned position. The system can analyze the current position and provide analytics to the user. The analytics can include, without limitation, modified anatomical configurations of the patient (e.g., configuration or curvature of the patient's spine and spinal procedures, joint function and joint repair procedures, bone configuration and bone repair procedures, etc.), predicted outcome scores, disease progression predictions, etc. In some embodiments, the system can compare and display outcomes for the planned procedure and the outcomes for the implant in the current position. This allows the user to assess whether the implant positioned at a non-planned position is acceptable. For example, the surgical plan may designate a particular implantation site for the implant. During the surgical procedure, the user may experience difficulty or may be unable to adequately deliver the implant to the planned implantation site. The user may decide to implant the implant at another location. The system can provide real time analytics based on intraoperative data to determine whether the alternative position is acceptable. In some embodiments, the system can generate new simulations and virtual models based on the intraoperative data. The intraoperative analytics can be used to determine whether the current position of the implant it is acceptable.

In some procedures, anatomical features can be altered in unplanned ways in order to, for example, access one or more surgical sites, provide a sufficient surgical path to deliver an implant to the surgical site, address unplanned adverse events (e.g., unplanned injuries to tissue, organs, etc.), etc. The system can determine whether to modify the surgical plan based on the alterations. In response to determining to modify the procedure, the system can receive intraoperative data describing the altered anatomical features and then intraoperatively generate a new surgical plan or a modified surgical plan.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items. As used herein and in the appended claims, the singular forms "a," "an," and "the" include plural references unless the context clearly dictates otherwise.

Although the disclosure herein primarily describes systems and methods for treatment planning in the context of orthopedic surgery, the technology may be applied equally to medical treatment and devices in other fields (e.g., other types of surgical practice). Additionally, although many embodiments herein describe systems and methods with respect to implanted devices, the technology may be applied equally to other types of medical devices (e.g., non-implanted devices).

FIG. 1 is a network connection diagram illustrating a computing system 100 for patient-specific medical care, according to an embodiment. As described in further detail herein, the system 100 is configured to generate a medical treatment plan based on patient data, patient-specific implants, radiographic images, or the like. The system 100 includes a client computing device 102, which can be a user device, such as a smart phone, mobile device, laptop, desktop, personal computer, tablet, phablet, or other such devices known in the art. As discussed further herein, the client computing device 102 can include one or more processors, and memory storing instructions executable by the one or more processors to perform the methods described herein. The client computing device 102 can be associated with a healthcare provider that is treating the patient. Although FIG. 1 illustrates a single client computing device 102, in alternative embodiments, the client computing device 102 can instead be implemented as a client computing system encompassing a plurality of computing devices, such that the operations described herein with respect to the client computing device 102 can instead be performed by the computing system and/or the plurality of computing devices.

The client computing device 102 is configured to receive a patient data set 108 associated with a patient to be treated. The patient data set 108 can include data representative of the patient's condition, anatomy, pathology, medical history, preferences, and/or any other information or parameters relevant to the patient. For example, the patient data set 108 can include medical history, surgical intervention data, treatment outcome data, progress data (e.g., physician notes), patient feedback (e.g., feedback acquired using quality of life questionnaires, surveys), clinical data, provider information (e.g., physician, hospital, surgical team), patient information (e.g., demographics, sex, age, height, weight, type of pathology, occupation, activity level, tissue information, health rating, comorbidities, health related quality of life (HRQL)), vital signs, diagnostic results, medication information, allergies, image data (e.g., camera images, Magnetic Resonance Imaging (MRI) images, ultrasound images, Computerized Aided Tomography (CAT) scan images, Positron Emission Tomography (PET) images, X-Ray images), diagnostic equipment information (e.g., manufacturer, model number, specifications, user-selected settings/configurations, etc.), or the like. In some embodiments, the patient data set 108 includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine.

The client computing device 102 is operably connected via a communication network 104 to a server 106, thus allowing for data transfer between the client computing device 102 and the server 106. The communication network 104 may be a wired and/or a wireless network. The communication network 104, if wireless, may be implemented using communication techniques such as Visible Light Communication (VLC), Worldwide Interoperability for Microwave Access (WiMAX), Long term evolution (LTE), Wireless local area network (WLAN), Infrared (IR) communication, Public Switched Telephone Network (PSTN), Radio waves, and/or other communication techniques known in the art.

The server 106, which may also be referred to as a "treatment assistance network" or "prescriptive analytics network," can include one or more computing devices and/or systems. As discussed further herein, the server 106 can include one or more processors, and memory storing instructions executable by the one or more processors to perform the methods described herein. In some embodiments, the server 106 is implemented as a distributed "cloud" computing system or facility across any suitable combination of hardware and/or virtual computing resources.

The client computing device 102 and server 106 can individually or collectively perform the various methods described herein for providing patient-specific medical care. For example, some or all of the steps of the methods described herein can be performed by the client computing device 102 alone, the server 106 alone, or a combination of the client computing device 102 and the server 106. Thus, although certain operations are described herein with respect to the server 106, it shall be appreciated that these operations can also be performed by the client computing device 102, and vice-versa.

The server 106 includes at least one database 110 configured to store reference data useful for the treatment planning methods described herein. The reference data can include historical and/or clinical data from the same or other patients, data collected from prior surgeries and/or other treatments of patients by the same or other healthcare providers, data relating to medical device designs, data collected from study groups or research groups, data from practice databases, data from academic institutions, data from implant manufacturers or other medical device manufacturers, data from imaging studies, data from simulations, clinical trials, demographic data, treatment data, outcome data, mortality rates, or the like.

In some embodiments, the database 110 includes a plurality of reference patient data sets, each patient reference data set associated with a corresponding reference patient. For example, the reference patient can be a patient that previously received treatment or is currently receiving treatment. Each reference patient data set can include data representative of the corresponding reference patient's condition, anatomy, pathology, medical history, disease progression, preferences, and/or any other information or parameters relevant to the reference patient, such as any of the data described herein with respect to the patient data set 108. In some embodiments, the reference patient data set includes pre-operative data, intra-operative data, and/or post-operative data. For example, a reference patient data set can include data representing one or more of patient ID, age, gender, BMI, lumbar lordosis, Cobb angle(s), pelvic incidence, disc height, segment flexibility, bone quality, rotational displacement, and/or treatment level of the spine. As another example, a reference patient data set can include treatment data regarding at least one treatment procedure performed on the reference patient, such as descriptions of surgical procedures or interventions (e.g., surgical approaches, bony resections, surgical maneuvers, corrective maneuvers, placement of implants or other devices). In some embodiments, the treatment data includes medical device design data for at least one medical device used to treat the reference patient, such as physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties). In yet another example, a reference patient data set can include outcome data representing an outcome of the treatment of the reference patient, such as corrected anatomical metrics, presence of fusion, HRQL, activity level, return to work, complications, recovery times, efficacy, mortality, and/or follow-up surgeries.

In some embodiments, the server 106 receives at least some of the reference patient data sets from a plurality of healthcare provider computing systems (e.g., systems 112a-112c, collectively 112). The server 106 can be connected to the healthcare provider computing systems 112 via one or more communication networks (not shown). Each healthcare provider computing system 112 can be associated with a corresponding healthcare provider (e.g., physician, surgeon, medical clinic, hospital, healthcare network, etc.). Each healthcare provider computing system 112 can include at least one reference patient data set (e.g., reference patient data sets 114a-114c, collectively 114) associated with reference patients treated by the corresponding healthcare provider. The reference patient data sets 114 can include, for example, electronic medical records, electronic health records, biomedical data sets, biomechanical data sets, mobility data sets, pain data sets, intra-operative image data, payment information, insurance information, insurer information, etc. The reference patient data sets 114 can be received by the server 106 from the healthcare provider computing systems 112 and can be reformatted into different formats for storage in the database 110. Optionally, the reference patient data sets 114 can be processed (e.g., cleaned) to ensure that the represented patient parameters are likely to be useful in the treatment planning methods described herein.

The server 106 can receive at least some information from an intra-operative image system 141 (e.g., device(s) capturing radiographic images, fluoroscopic images, C-Arm device images, x-ray images, etc.). In some embodiments, the radiographic images are captured using an x-ray machine, C-Arm machine, fluoroscopic imaging device, etc. For example, the server 106 can be connected to the system 141 via one or more communication networks (not shown). The system 141 can include one or more outcome data databases, image databases, pre-op, intra-operative, and post-operative databases, or the like. The server 106 can request and retrieve data sets 117 from the system 141. The system 141 can include, without limitation, an x-ray machine, fluoroscopic imaging device, a CT scanner, an MRI machine, or other imaging equipment that can be located approximate or within the surgical suite.

As described in further detail herein, the server 106 can be configured with one or more algorithms that generate patient-specific treatment plan data (e.g., treatment procedures, medical devices, etc.) based on the reference data. In some embodiments, the patient-specific data is generated based on correlations between the patient data set 108 and the reference data. Optionally, the server 106 can predict outcomes, including recovery times, efficacy based on clinical end points, likelihood of success, predicted mortality, predicted related follow-up surgeries, or the like. In some embodiments, the server 106 can continuously or periodically analyze patient data (including patient data obtained during the patient stay) to determine near real-time or real-time risk scores, mortality prediction, etc.

In some embodiments, the server 106 includes one or more modules for performing one or more steps of the patient-specific treatment planning methods described herein. For example, in the depicted embodiment, the server 106 includes a data analysis module 116 and a surgical planning and confirmation platform 109 ("SPC platform 109"). The SPC platform 109 includes a treatment planning module 118, a surgical implant positioning manager 119, and a database 151. In alternative embodiments, one or more of these modules may be combined with each other, or may be omitted. Thus, although certain operations are described herein with respect to a particular module or modules, this is not intended to be limiting, and such operations can be performed by a different module or modules in alternative embodiments. For example, the SPC platform 109 can be incorporated into the data analysis module 116. In other embodiments, the modules of the system 100 can be combined with modules of other systems. For example, the SPC platform 109 can be part of or incorporated into a healthcare system 133 and can manage reconciliation of intra-operative implant positioning to surgical plans. The reconciliation can be outcome-driven reconciliation for reducing or eliminating intra-operative implant mispositioning that is likely to affect one or more outcomes more than acceptable threshold amount(s).

The data analysis module 116 is configured with one or more algorithms for identifying a subset of reference data from the database 110 that is likely to be useful in developing a patient-specific treatment plan. For example, the data analysis module 116 can compare patient-specific data (e.g., the patient data set 108 received from the client computing device 102) to the reference data from the database 110 (e.g., the reference patient data sets) to identify similar data (e.g., one or more similar patient data sets in the reference patient data sets). The comparison can be based on one or more parameters, such as age, gender, BMI, lumbar lordosis, pelvic incidence, and/or treatment levels. The parameter(s) can be used to calculate a similarity score for each reference patient. The similarity score can represent a statistical correlation between the patient data set 108 and the reference patient data set. Accordingly, similar patients can be identified based on whether the similarity score is above, below, or at a specified threshold value. For example, as described in greater detail below, the comparison can be performed by assigning values to each parameter and determining the aggregate difference between the subject patient and each reference patient. Reference patients whose aggregate difference is below a threshold can be considered to be similar patients.

The data analysis module 116 can further be configured with one or more algorithms to select a subset of the reference patient data sets, e.g., based on similarity to the patient data set 108 and/or treatment outcome of the corresponding reference patient. For example, the data analysis module 116 can identify one or more similar patient data sets in the reference patient data sets, and then select a subset of the similar patient data sets based on whether the similar patient data set includes data indicative of a favorable or desired treatment outcome. The outcome data can include data representing one or more outcome parameters, such as corrected anatomical metrics, presence of fusion, HRQL, activity level, complications, recovery times, efficacy, mortality, or follow-up surgeries. As described in further detail below, in some embodiments, the data analysis module 116 calculates an outcome score by assigning values to each outcome parameter. A patient can be considered to have a favorable outcome if the outcome score is above, below, or at a specified threshold value.

In some embodiments, the data analysis module 116 selects a subset of the reference patient data sets based at least in part on user input (e.g., from a clinician, surgeon, physician, healthcare provider). For example, the user input can be used in identifying similar patient data sets. In some embodiments, weighting of similarity and/or outcome parameters can be selected by a healthcare provider or physician to adjust the similarity and/or outcome score based on clinician input. In further embodiments, the healthcare provider or physician can select the set of similarity and/or outcome parameters (or define new similarity and/or outcome parameters) used to generate the similarity and/or outcome score, respectively.

In some embodiments, the data analysis module 116 includes one or more algorithms used to select a set or subset of the reference patient data sets based on criteria other than patient parameters. For example, the one or more algorithms can be used to select the subset based on healthcare provider parameters (e.g., based on healthcare provider ranking/ scores such as hospital/physician expertise, number of procedures performed, hospital ranking, etc.) and/or healthcare resource parameters (e.g., diagnostic equipment, facilities, surgical equipment such as surgical robots), or other non-patient related information that can be used to predict outcomes and risk profiles for procedures for the present healthcare provider. For example, reference patient data sets with images captured from similar diagnostic equipment can be aggregated to reduce or limit irregularities due to variation between diagnostic equipment. Additionally, patient-specific treatment plans can be developed for a particular health-care provider using data from similar healthcare providers (e.g., healthcare providers with traditionally similar outcomes, physician expertise, surgical teams, etc.). In some embodiments, reference healthcare provider data sets, hospital data sets, physician data sets, surgical team data sets, post-treatment data set, and other data sets can be utilized. By way of example, a patient-specific treatment plan to perform a battlefield surgery can be based on reference patient data from similar battlefield surgeries and/or data sets associated with battlefield surgeries. In another example, the patient-specific treatment plan can be generated based on available robotic surgical systems. The reference patient data sets can be selected based on patients that have been operated on using comparable robotic surgical systems under similar conditions (e.g., size and capabilities of surgical teams, hospital resources, etc.).

The SPC platform 109 can include the treatment planning module 118, the surgical implant positioning manager 119, and the database 151. The treatment planning module 118 is configured with one or more algorithms to generate at least one treatment plan (e.g., pre-operative plans, intra-operative plans, surgical plans, post-operative plans, etc.) based on the output from the data analysis module 116. In some embodiments, the treatment planning module 118 is configured to develop and/or implement at least one predictive model for generating plans. The predictive model(s) can be developed using clinical knowledge, statistics, machine learning, AI, neural networks, or the like. In some embodiments, the output from the data analysis module 116 is analyzed (e.g., using statistics, machine learning, neural networks, AI) to identify correlations between data sets, patient parameters, healthcare provider parameters, healthcare resource parameters, treatment procedures, medical device designs, and/or treatment outcomes. These correlations can be used to develop at least one predictive model that predicts the likelihood that a treatment plan will produce a favorable outcome for the particular patient. The predictive model(s) can be validated, e.g., by inputting data into the model(s) and comparing the output of the model to the expected output. Machine learning models can be trained to analyze pre-operative plans and intra-operative data to determine whether the position (e.g., location, orientation, etc.) of anatomical element(s), instrument(s), or implant(s) in a patient during a surgical procedure matches the position in the pre-operative plan.

In orthopedic procedures, the machine learning models can be trained to determine whether anatomical elements, such as bones and/or joints, are at targeted positions. The instruments can be surgical instruments for accessing surgical sites, implanting implants, anchoring (e.g., securing implants to bony tissue), or the like. In joint repair procedures, the anatomical elements can include bones, cartilage, connective tissue, and other anatomical elements that affect joint position and/or function. The instruments can be joint repair instruments. In spinal procedures, the position of anatomical elements can include soft tissue that may contribute to nerve compression. The system can identify tissue that can be removed to, for example, reduce nerve compression, facilitate implantation of implants, and/or perform other steps for decompression. The machine learning models can be trained based on the procedure to be performed.

The system 100 can predict intra-operative patient mobility and identify mobility related surgical steps. The system 100 can perform the techniques and methods disclosed in U.S. patent application Ser. No. 17/868,729, which is incorporated by reference in its entirety. For example, the SPC platform 109 can identify soft tissue surgical steps for adjusting intra-operative mobility of anatomical features to facilitate implantation at target locations. One or more predictive models can identify specific soft tissue (e.g., tissue of cartilage, ligaments, etc.) that can be cut, removed, or manipulated to achieve desired operative mobility of, for example, bones, organs, or other anatomical elements. The modified intra-operative ability can facilitate delivery and positioning of the implant. In some embodiments, the intra-operative mobility can be predicted prior to beginning of surgery, a sequence of surgical steps, or the like. In some embodiments, the system 100 can intra-operative generate surgical steps based on intra-operative data. This allows real-time intra-operative steps to be generated based on the current condition of the patient. In some procedures, a surgical plan can include soft tissue surgical steps to facilitate movement of anatomical elements, implantation of implants, or the like. Additionally, the methods and systems disclosed herein can be combined or used with techniques or methods disclosed in U.S. patent application Ser. No. 17/978,746, which is incorporated by reference in its entirety. For example, one or more decompression steps can be performed during the surgical procedure. Sites of nerve compression can be pre-operatively and/or intra-operatively identified. Targeted tissue that contributes to the nerve compression can be identified. The system 100 can develop one or more surgical steps for accessing and performing one or more decompression steps on the targeted tissue (e.g., removal and/or repositioning of targeted tissues). This allows for spinal decompression procedures to be performed to enhanced outcomes.

The treatment planning module 118 can be configured include one or more soft tissue surgical steps. The soft tissue surgical steps can facilitate movement of anatomical features to facilitate implantation. The soft tissue surgical steps can include severing, dissecting, cutting, and/or removing tissue. For example, ligaments (e.g., supraspinous ligament, interspinous ligaments, spinal ligaments, etc.) can be severed to access and move apart adjacent spinous processes, vertebral bodies, etc. In some example plans, the soft tissue surgical steps include one or more of severing soft tissue located along the patient's spine, removing at least a portion of an annulus, and/or resecting cartilage along the spine. The treatment planning module 118 can virtually move anatomical elements to identify soft tissue that inhibits or prevents desired movement, block access paths to implantation sites, etc. Simulations of soft tissue surgical steps can be performed to select recommended soft tissue surgical steps for achieving positionality of the anatomical elements.

In some example plans, the soft tissue surgical steps include one or more decompression procedures. The system can predict a decompression score for each decompression procedure. The nerve decompression score can be based on, for example, a predicted percentage decrease of pain felt by the patient. The system can generate a plurality of decompression plans, determine a decompression score (e.g., postoperative pain score, nerve decompression score, etc.) for each decompression plan, receive selection of one of the decompression plans, and generate a decompression surgical plan based on the selected decompression plan. The user can modify the selected decompression plan based on a corrected configuration of the patient's spine. The decompression plans can include at least one of a laminectomy, a laminotomy, a microdiscectomy, a foraminotomy, and/or an osteophyte procedure.

In some example plans, the planned surgical steps include one or more decompression steps for spinal procedures. The system can predict a decompression score for each decompression step, series of steps, and/or decompression procedure. The nerve decompression score can be based on, for example, a predicted percentage decrease of pain felt by the patient. The system can generate a plurality of decompression plans, determine a decompression score (e.g., postoperative pain score, nerve decompression score, etc.) for each decompression plan, receive selection of one of the decompression plans, and generate a decompression surgical plan based on the selected decompression plan. The user can modify the selected decompression plan based on a corrected configuration of the patient's spine. The decompression plans can include at least one of a laminectomy, a laminotomy, a microdiscectomy, a foraminotomy, and/or an osteophyte procedure.

The amount of movement of implants, anatomical elements, and other features of interest attributable to each step can be predicted to facilitate surgical planning and simulations. A simulation can predict joint mobility of the patient's spine or specific joints. A user can select one or more of the implant position(s) (e.g., pre-operative planned position, intra-operative planned position, predicted post-operative position based one or more loading conditions) identified surgical steps based on the simulated joint mobility, targeted corrective anatomical configuration, etc. The treatment planning module 118 can predict intra-operative joint mobility and/or post-operative joint mobility associated with the selected soft tissue surgical steps. This allows the user to select a surgical plan with surgical steps for helping reposition anatomical elements, implantation at targeted site(s), etc.

In some embodiments, the treatment planning module 118 is configured to generate the treatment plan based on previous treatment data from reference patients. For example, the treatment planning module 118 can receive a selected subset of reference patient data sets and/or similar patient data sets from the data analysis module 116, and determine or identify treatment data from the selected subset. The treatment data can include, for example, treatment procedure data (e.g., surgical procedure or intervention data) and/or medical device design data (e.g., implant design data) that are associated with favorable or desired treatment outcomes for the corresponding patient. The treatment planning module 118 can analyze the treatment procedure data and/or medical device design data to determine an optimal treatment protocol for the patient to be treated. For example, the treatment procedures and/or medical device designs can be assigned values and aggregated to produce a treatment score. The patient-specific treatment plan can be determined by selecting treatment plan(s) based on the score (e.g., higher or highest score; lower or lowest score; score that is above, below, or at a specified threshold value). The personalized patient-specific treatment plan can be based on, at least in part, the patient-specific technologies or patient-specific selected technology.

Alternatively or in combination, the treatment planning module 118 can generate the treatment plan based on correlations between data sets. For example, the treatment planning module 118 can correlate treatment procedure data and/or medical device design data from similar patients with favorable outcomes (e.g., as identified by the data analysis module 116). Correlation analysis can include transforming correlation coefficient values to values or scores. The values/scores can be aggregated, filtered, or otherwise analyzed to determine one or more statistical significances. These correlations can be used to determine treatment procedure(s) and/or medical device design(s) that are optimal or likely to produce a favorable outcome for the patient to be treated.

Alternatively or in combination, the treatment planning module 118 can generate the treatment plan using one or more AI techniques. AI techniques can be used to develop computing systems capable of simulating aspects of human intelligence, e.g., learning, reasoning, planning, problem solving, decision making, etc. AI techniques can include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems.

In some embodiments, the treatment planning module 118 generates the treatment plan using one or more trained machine learning models. Various types of machine learning models, algorithms, and techniques are suitable for use with the present technology. In some embodiments, the machine learning model is initially trained on a training data set, which is a set of examples used to fit the parameters (e.g., weights of connections between "neurons" in artificial neural networks) of the model. For example, the training data set can include any of the reference data stored in database 110, such as a plurality of reference patient data sets or a selected subset thereof (e.g., a plurality of similar patient data sets).

In some embodiments, the machine learning model (e.g., a neural network or a naïve Bayes classifier) may be trained on the training data set using a supervised learning method (e.g., gradient descent or stochastic gradient descent). The training data set can include pairs of generated "input vectors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some embodiments, the error of the validation data set error can fluctuate during training, such that ad-hoc rules may be used to decide when overfitting has truly begun. Finally, a test data set can be used to provide an unbiased evaluation of a final model fit on the training data set.

To generate a treatment plan, the patient data set 108 can be input into the trained machine learning model(s). Additional data, such as the selected subset of reference patient data sets and/or similar patient data sets, and/or treatment data from the selected subset, can also be input into the trained machine learning model(s). The trained machine learning model(s) can then calculate whether various candidate treatment procedures and/or medical device designs are likely to produce a favorable outcome for the patient, meet one or more parameters (e.g., coverage parameters, reimbursement parameters, regulatory parameters, or the like). Based on these calculations, the trained machine learning model(s) can select at least one treatment plan for the patient. In embodiments where multiple trained machine learning models are used, the models can be run sequentially or concurrently to compare outcomes and can be periodically updated using training data sets. The treatment planning module 118 can use one or more of the machine learning models based the model's predicted accuracy score.

The patient-specific treatment plan generated by the treatment planning module 118 can include at least one patient-specific treatment procedure (e.g., a surgical procedure or intervention) and/or at least one patient-specific medical device (e.g., an implant or implant delivery instrument). A patient-specific treatment plan can include an entire surgical procedure or portions thereof. Additionally, one or more patient-specific medical devices can be specifically selected or designed for the corresponding surgical procedure, thus allowing for the various components of the patient-specific technology to be used in combination to treat the patient.

In some embodiments, the patient-specific treatment procedure includes an orthopedic surgery procedure, such as spinal surgery, hip surgery, knee surgery, jaw surgery, hand surgery, shoulder surgery, elbow surgery, total joint reconstruction (arthroplasty), skull reconstruction, foot surgery, or ankle surgery. Spinal surgery can include spinal fusion surgery, such as posterior lumbar interbody fusion (PLIF), cervical fusion, anterior lumbar interbody fusion (ALIF), transverse or transforaminal lumbar interbody fusion (TLIF), lateral lumbar interbody fusion (LLIF), direct lateral lumbar interbody fusion (DLIF), or extreme lateral lumbar interbody fusion (XLIF). In some embodiments, the patient-specific treatment procedure includes descriptions of and/or instructions for performing one or more aspects of a patient-specific surgical procedure. For example, the patient-specific surgical procedure can include one or more of a surgical approach, a corrective maneuver, a bony resection, or implant placement.

In some embodiments, the patient-specific medical device design includes a design for an orthopedic implant and/or a design for an instrument for delivering an orthopedic implant. Examples of such implants include, but are not limited to, screws (e.g., bone screws, spinal screws, pedicle screws, facet screws), interbody implant devices (e.g., intervertebral implants), cages, plates, rods, disks, fusion devices, spacers, rods, expandable devices, stents, brackets, ties, scaffolds, fixation device, anchors, nuts, bolts, rivets, connectors, tethers, fasteners, joint replacements, hip implants, or the like. Examples of instruments include, but are not limited to, screw guides, cannulas, ports, catheters, insertion tools, or the like.

A patient-specific medical device design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of a corresponding medical device. For example, a design for an orthopedic implant can include implant shape, size, material, and/or effective stiffness (e.g., lattice density, number of struts, location of struts, etc.). In some embodiments, the generated patient-specific medical device design is a design for an entire device. Alternatively, the generated design can be for one or more components of a device, rather than the entire device.

In some embodiments, the design is for one or more patient-specific device components that can be used with standard, off-the-shelf components. For example, in a spinal surgery, a pedicle screw kit can include both standard components and patient-specific customized components. In some embodiments, the generated design is for a patient-specific medical device that can be used with a standard, off-the-shelf delivery instrument. For example, the implants (e.g., screws, screw holders, rods) can be designed and manufactured for the patient, while the instruments for delivering the implants can be standard instruments. This approach allows the components that are implanted to be designed and manufactured based on the patient's anatomy and/or surgeon's preferences to enhance treatment. The patient-specific devices described herein are expected to improve delivery into the patient's body, placement at the treatment site, and/or interaction with the patient's anatomy.

In embodiments where the patient-specific treatment plan includes a surgical procedure to implant a medical device, the treatment planning module 118 can also store various types of implant surgery information, such as implant parameters (e.g., types, dimensions), availability of implants, aspects of a pre-operative plan (e.g., initial implant configuration, detection and measurement of the patient's anatomy, etc.), FDA requirements for implants (e.g., specific implant parameters and/or characteristics for compliance with FDA regulations), or the like. In some embodiments, the treatment planning module 118 can convert the implant surgery information into formats useable for machine-learning based models and algorithms. For example, the implant surgery information can be tagged with particular identifiers for formulas or can be converted into numerical representations suitable for supplying to the trained machine learning model(s). The treatment planning module 118 can also store information regarding the patient's anatomy, such as two- or three-dimensional images or models of the anatomy, and/or information regarding the biology, geometry, and/or mechanical properties of the anatomy. The anatomy information can be used to inform implant design and/or placement.

The treatment plan(s) generated by the treatment planning module 118 can be transmitted via the communication network 104 to the client computing device 102 for output to a user (e.g., clinician, surgeon, healthcare provider, patient). In some embodiments, the client computing device 102 includes or is operably coupled to a display 122 for outputting the treatment plan(s). The display 122 can include a graphical user interface (GUI) for visually depicting various aspects of the treatment plan(s). For example, the display 122 can show various aspects of a surgical procedure to be performed on the patient, such as the surgical approach, treatment levels, corrective maneuvers, tissue resection, and/or implant placement. To facilitate visualization, a virtual model of the surgical procedure can be displayed. As another example, the display 122 can show a design for a medical device to be implanted in the patient, such as a two- or three-dimensional model of the device design. The display 122 can also show patient information, such as two- or three-dimensional images or models of the patient's anatomy where the surgical procedure is to be performed and/or where the device is to be implanted. The client computing device 102 can further include one or more user input devices (not shown) allowing the user to modify, select, approve, and/or reject the displayed treatment plan(s).

The surgical implant positioning manager 119 can analyze and manage confirmation of intra-operative positioning data, intra-operative data (e.g., radiographic images, ultrasound, MRI, etc.) and other information. The database 151 can search for, retrieve, and store data from systems 141 or other systems. For example, the server 106 can be trained to generate new treatment plans, and the database 151 can provide reconciliation of intra-op implant positioning to surgical plans. The database 151 can then retrieve the intra-operative data sets, pre-operative data sets, and post-operative data sets, from the system 141. The surgical implant positioning manager 119 can analyze and provide confirmation of intra-operative positioning of surgical implants based on the pre-operative plan. The surgical implant positioning manager 119 can compensate for the loading conditions of anatomical elements associated with the pre-operative data sets. For example, the surgical implant positioning manager 119 can modify the pre-operative data sets (or virtual model generated based on the pre-operative data sets) to compensate for differences in loading conditions of the pre-operative data sets (for example, the patient was standing to obtain pre-operative standing x-ray data) and intra-operative data sets with other loaded conditions (e.g., the patient is laying down).

In some embodiments, the medical device design(s) generated by the server 106 can be transmitted from the client computing device 102 and/or server 106 to a manufacturing system 124 for manufacturing a corresponding medical device. The manufacturing system 124 can be located on site or off site. On-site manufacturing can reduce the number of sessions with a patient and/or the time to be able to perform the surgery whereas off-site manufacturing can be useful make the complex devices. Off-site manufacturing facilities can have specialized manufacturing equipment. In some embodiments, more complicated device components can be manufactured off site, while simpler device components can be manufactured on site.

Various types of manufacturing systems are suitable for use in accordance with the embodiments herein. Manufacturing can be achieved using human design, machine design, a combination of human and machine design, or other design techniques. For example, the manufacturing system 124 can be configured for additive manufacturing, such as three-dimensional (3D) printing, stereolithography (SLA), digital light processing (DLP), fused deposition modeling (FDM), selective laser sintering (SLS), selective laser melting (SLM), selective heat sintering (SHM), electronic beam melting (EBM), laminated object manufacturing (LOM), powder bed printing (PP), thermoplastic printing, direct material deposition (DMD), inkjet photo resin printing, or like technologies, or combination thereof. Alternatively or in combination, the manufacturing system 124 can be configured for subtractive (traditional) manufacturing, such as CNC machining, electrical discharge machining (EDM), grinding, laser cutting, water jet machining, manual machining (e.g., milling, lathe/turning), or like technologies, or combinations thereof. The manufacturing system 124 can manufacture one or more patient-specific medical devices based on fabrication instructions or data (e.g., CAD data, 3D data, digital blueprints, stereolithography data, or other data suitable for the various manufacturing technologies described herein). Different components of the system 100 can generate at least a portion of the manufacturing data used by the manufacturing system 124. The manufacturing data can include, without limitation, fabrication instructions (e.g., programs executable by additive manufacturing equipment, subtractive manufacturing equipment, etc.), 3D data, CAD data (e.g., CAD files), CAM data (e.g., CAM files), path data (e.g., print head paths, tool paths, etc.), material data, tolerance data, surface finish data (e.g., surface roughness data), regulatory data (e.g., FDA requirements, reimbursement data, etc.), or the like. The manufacturing system 124 can analyze the manufacturability of the implant design based on the received manufacturing data. The implant design can be finalized by altering geometries, surfaces, etc. and then generating manufacturing instructions. In some embodiments, the server 106 generates at least a portion of the manufacturing data, which is transmitted to the manufacturing system 124.

The manufacturing system 124 can generate CAM data, print data (e.g., powder bed print data, thermoplastic print data, photo resin data, etc.), or the like and can include additive manufacturing equipment, subtractive manufacturing equipment, thermal processing equipment, or the like. The additive manufacturing equipment can be 3D printers, stereolithography devices, digital light processing devices, fused deposition modeling devices, selective laser sintering devices, selective laser melting devices, electronic beam melting devices, laminated object manufacturing devices, powder bed printers, thermoplastic printers, direct material deposition devices, or inkjet photo resin printers, or like technologies. The subtractive manufacturing equipment can be CNC machines, electrical discharge machines, grinders, laser cutters, water jet machines, manual machines (e.g., milling machines, lathes, etc.), or like technologies. Both additive and subtractive techniques can be used to produce implants with complex geometries, surface finishes, material properties, etc. The generated fabrication instructions can be configured to cause the manufacturing system 124 to manufacture the patient-specific orthopedic implant that matches or is therapeutically the same as the patient-specific design.

In some embodiments, the patient-specific medical device can include features, materials, and designs shared across designs to simplify manufacturing. For example, deployable patient-specific medical devices for different patients can have similar internal deployment mechanisms but have different deployed configurations. In some embodiments, the components of the patient-specific medical devices are selected from a set of available pre-fabricated components and the selected pre-fabricated components can be modified based on the fabrication instructions or data.

The manufacturing system 124, implant analyzer 129, and/or surgical implant positioning manager 119 can communicate directly with one another or via the communication network 104. The system 100 can perform one or more validation steps for a manufactured implant. The analyzer 129 can include one or more scanners, cameras, or imaging devices and can be incorporated into the manufacturing system 124 or other components of the system 100 and can scan the manufactured implant to, for example, identify manufacturing defects, confirm the implant meets one or regulatory requirements, etc. By analyzing implant characteristics (e.g., composition of the material, surface topology, etc.) and manufacturing parameters (e.g., composition of the material, temperature, speed of printing, manufacturing conditions, accuracy of printer, etc.), the system 100 can determine whether the implant should be implanted in a patient. If the implant is not acceptable, system 100 can determine manufacturing adjustments for the implant to be remanufactured. The analyzer 129 can be onsite manufacturing scanners positioned to scan implants during and/or after fabrication. In some embodiments, the analyzers 129 are offsite of the manufacturing location. For example, the analyzers 129 can be located at a healthcare provider (e.g., at a hospital, clinic, surgical suite, etc.) to allow quality control checking immediately prior to implantation, verification of regulatory compliance, etc.

The manufacturing system 124 can manufacture all or some of the components of a kit. The kit components can be selected based on requirement(s), including regulatory requirements, reimbursement requirements, or other requirements. Surgical kits can include one or more implants, instruments, instructions for use, and reusable and disposable components. The kit requirements can be retrieved from a database 151. The system 100 can synchronize the surgical plan with the requirements to generate patient-specific surgical kits meeting the requirements.

The treatment plans described herein can be performed by a surgeon, a surgical robot, or a combination thereof, thus allowing for treatment flexibility. In some embodiments, the surgical procedure can be performed entirely by a surgeon, entirely by a surgical robot, or a combination thereof. For example, one step of a surgical procedure can be manually performed by a surgeon and another step of the procedure can be performed by a surgical robot. In some embodiments the treatment planning module 118 generates control instructions configured to cause a surgical robot (e.g., robotic surgery systems, navigation systems, etc.) to partially or fully perform a surgical procedure. The control instructions can be transmitted to the robotic apparatus by the client computing device 102 and/or the server 106.

Following the treatment of the patient in accordance with the treatment plan, treatment progress can be monitored over one or more time periods to update the data analysis module 116 and/or treatment planning module 118. Post-treatment data can be added to the reference data stored in the database 110. The post-treatment data can be used to train machine learning models for developing patient-specific treatment plans, patient-specific medical devices, or combinations thereof.

It shall be appreciated that the components of the system 100 can be configured in many different ways. For example, in alternative embodiments, the database 110, the data analysis module 116 and/or the treatment planning module 118 can be components of the client computing device 102, rather than the server 106. As another example, the database 110 the data analysis module 116, and/or the treatment planning module 118 can be located across a plurality of different servers, computing systems, or other types of cloud-computing resources, rather than at a single server 106 or client computing device 102.

The treatment planning module 118 can communicate with the surgical implant positioning manager 119 to obtain intra-operative data. The display 122 can display an intra-operative data 123 and pre-operative data 127 virtually overlaid on each other to illustrate the placement and position of the implant 161. A user can review proposed pathology 129, a treatment plan 157, and implant(s) 161. The treatment plan 157 can be an interactive plan having a user input element 165 (e.g., one or more buttons, a drop-down menu, toggle, etc.) for modification and/or approval. The intra-operative data 123 and pre-operative data 127 can be dynamically updated based on the user input. This allows a user to identify the intra-op positioning of surgical implants based on the pre-operative plan. The display 122 can graphically overlay an intra-operative image over a pre-operative plan/model/image. A user (e.g., healthcare provider, such as a surgeon) can manipulate (e.g., zoom, stretch, crop, and/or rotate) the intra-operative image to align with the pre-operative model (e.g., virtual 3D model), images (e.g., images of virtual models), anatomical renderings, or other images displaying anatomical position information on the device. In some cases, a user can zoom, stretch, and/or rotate the virtual 3D model (or other pre-operative images) to align with the intra-operative image on the device or other viewing platform. In some embodiments, the treatment planning module 118 can analyze pre-operative data and then manipulate pre-operative data (e.g., pre-operative images, virtual 3D models, etc.) to align or otherwise synchronize the pre-operative and intra-operative data. For example, the treatment planning module 118 can generate images of a virtual 3D model of patient anatomy in a corrected configuration such that those images match intra-operative images. The treatment planning module 118 can use a machine learning engine to align anatomical features in the virtual 3D model with corresponding anatomical features in the images by, for example, manipulating the virtual 3D model, images, or both. The 3D virtual model can include, for example, representations of patient's anatomy, implants, instruments, or other models disclosed herein.

The system 100 is configured to determine one or more measurements to confirm implant placement. For example, the system 100 calculates a difference (e.g., delta, deviation, etc.) between the intra-operative data and the pre-operative plan. Display 122 can display the measurements to a user. In some implementations, display 122 shows, during a surgical procedure, a live comparison between the intra-operative data and the pre-operative plan. In some embodiments, a threshold delta can be determined by the system 100, inputted by a user, or the like. The system 100 can notify the user if the measurement exceeds the threshold delta. In some procedures, the threshold delta can be based on implantation envelopes, boundaries, or other targeting features determined by the system 100, user, or the like. For example, a user can draw a two-dimensional or three-dimensional boundary on anatomical images for acceptable positions of the implant. The system 100 can then determine whether the implant, or sufficient amount of the implant, is positioned within the boundary. System 100 can calculate a completion score for a surgical procedure and display the score on display 122. In an illustrative example, a device captures an intra-operative image and displays the intra-operative image over the pre-operative plan. System 100 can scale and orient the intra-operative image to closely match the pre-operative plan, reflecting the location of anatomical landmarks and implant. The matching can be performed using one or more segmentation program, best fit algorithms, image manipulation programs, or the like.

System 100 can display, correlate, and/or measure the planned position of an implant and the current location of the implant to help healthcare providers properly implant and position an implant in a patient. Additionally, system 100 can compare post-operative imaging to pre-operative models, intra-operative images, and treatment plans, according to the techniques described herein. System 100 can utilize the techniques described herein for multiple stage surgeries (e.g., anterior surgery performed first, posterior surgery performed next, lateral surgery performed next, etc.). System 100 can perform confirmation of placement of implant based on surgical plan or monitoring migration during other aspects of patient care or subsequent surgery. The system 100 can predict post-operative outcomes based on, for example, the monitoring, local anatomical environment conditions. Image analysis can be used to determine/predict post-operative mobility (e.g., anatomical configurations, mobility after surgical intervention, etc.) based, at least in part, on the intra-operative data, disease progression scores, etc.

The system 100 is configured to design the physical patient-specific implants 154 for achieving the approved planned pathology 129. The surgical implant positioning manager 119 can also retrieve information regarding the patient's anatomy, such as pre-operative measurements, two- or three-dimensional images or models of the anatomy, and/or information regarding the biology, geometry, and/or mechanical properties of the anatomy. Example implant designing is discussed in connection with FIGS. 3-13.

Additionally, in some embodiments, the system 100 can be operational with numerous other computing system environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

Figure 2:
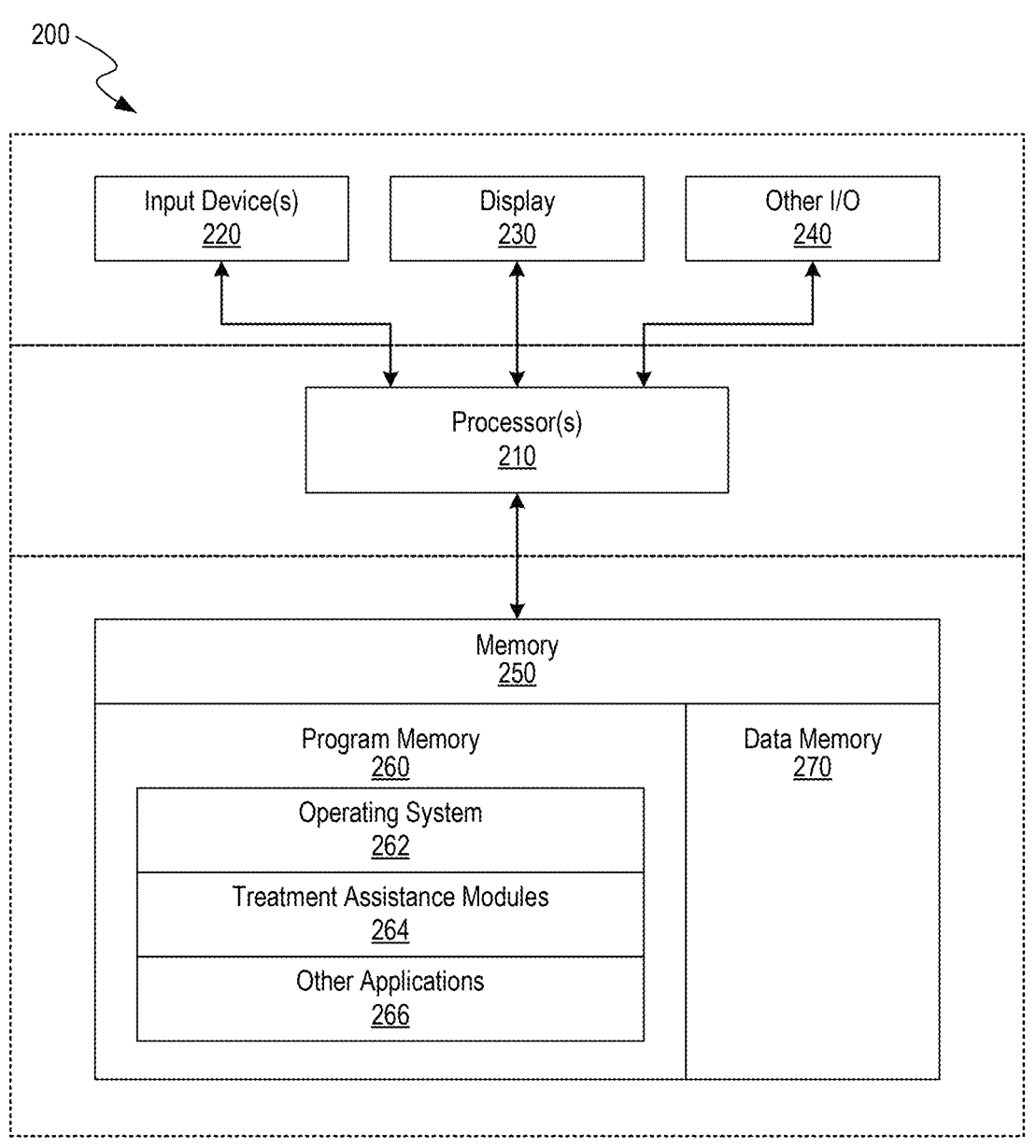
FIG. 2 illustrates a computing device suitable for use in connection with the system of FIG. 1, according to an embodiment.

FIG. 2 illustrates a computing device 200 suitable for use in connection with the system 100 of FIG. 1, according to an embodiment. The computing device 200 can be incorporated in various components of the system 100 of FIG. 1, such as the client computing device 102 or the server 106. The computing device 200 includes one or more processors 210 (e.g., CPU(s), GPU(s), HPU(s), etc.). The processor(s) 210 can be a single processing unit or multiple processing units in a device or distributed across multiple devices. The processor(s) 210 can be coupled to other hardware devices, for example, with the use of a bus, such as a PCI bus or SCSI bus. The processor(s) 210 can be configured to execute one more computer-readable program instructions, such as program instructions to carry out of any of the methods described herein.

The computing device 200 can include one or more input devices 220 that provide input to the processor(s) 210, e.g., to notify it of actions from a user of the device 200. The actions can be mediated by a hardware controller that interprets the signals received from the input device and communicates the information to the processor(s) 210 using a communication protocol. Input device(s) 220 can include, for example, a mouse, a keyboard, a touchscreen, an infrared sensor, a touchpad, a wearable input device, a camera- or image-based input device, a microphone, or other user input devices.

The computing device 200 can include a display 230 used to display various types of output, such as text, models, virtual procedures, surgical plans, implants, graphics, and/or images (e.g., images with voxels indicating radiodensity units or Hounsfield units representing the density of the tissue at a location). In some embodiments, the display 230 provides graphical and textual visual feedback to a user. The processor(s) 210 can communicate with the display 230 via a hardware controller for devices. In some embodiments, the display 230 includes the input device(s) 220 as part of the display 230, such as when the input device(s) 220 include a touchscreen or is equipped with an eye direction monitoring system. In alternative embodiments, the display 230 is separate from the input device(s) 220. Examples of display devices include an LCD display screen, an LED display screen, a projected, holographic, or augmented reality display (e.g., a heads-up display device or a head-mounted device), and so on.

Optionally, other I/O devices 240 can also be coupled to the processor(s) 210, such as a network card, video card, audio card, USB, firewire or other external device, camera, printer, speakers, CD-ROM drive, DVD drive, disk drive, or Blu-Ray device. Other I/O devices 240 can also include input ports for information from directly connected medical equipment such as imaging apparatuses, including MRI machines, X-Ray machines, CT machines, etc. Other I/O devices 240 can further include input ports for receiving data from these types of machine from other sources, such as across a network or from previously captured data, for example, stored in a database.

In some embodiments, the computing device 200 also includes a communication device (not shown) capable of communicating wirelessly or wire-based with a network node. The communication device can communicate with another device or a server through a network using, for example, TCP/IP protocols. The computing device 200 can utilize the communication device to distribute operations across multiple network devices, including imaging equipment, manufacturing equipment, etc.

The computing device 200 can include memory 250, which can be in a single device or distributed across multiple devices. Memory 250 includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. In some embodiments, the memory 250 is a non-transitory computer-readable storage medium that stores, for example, programs, software, data, or the like. In some embodiments, memory 250 can include program memory 260 that stores programs and software, such as an operating system 262, one or more treatment assistance modules 264, and other application programs 266. The treatment assistance module(s) 264 can include one or more modules configured to perform the various methods described herein (e.g., the data analysis module 116 and/or treatment planning module 118 described with respect to FIG. 1). Memory 250 can also include data memory 270 that can include, e.g., reference data, configuration data, settings, user options or preferences, etc., which can be provided to the program memory 260 or any other element of the computing device 200.

Figure 3:
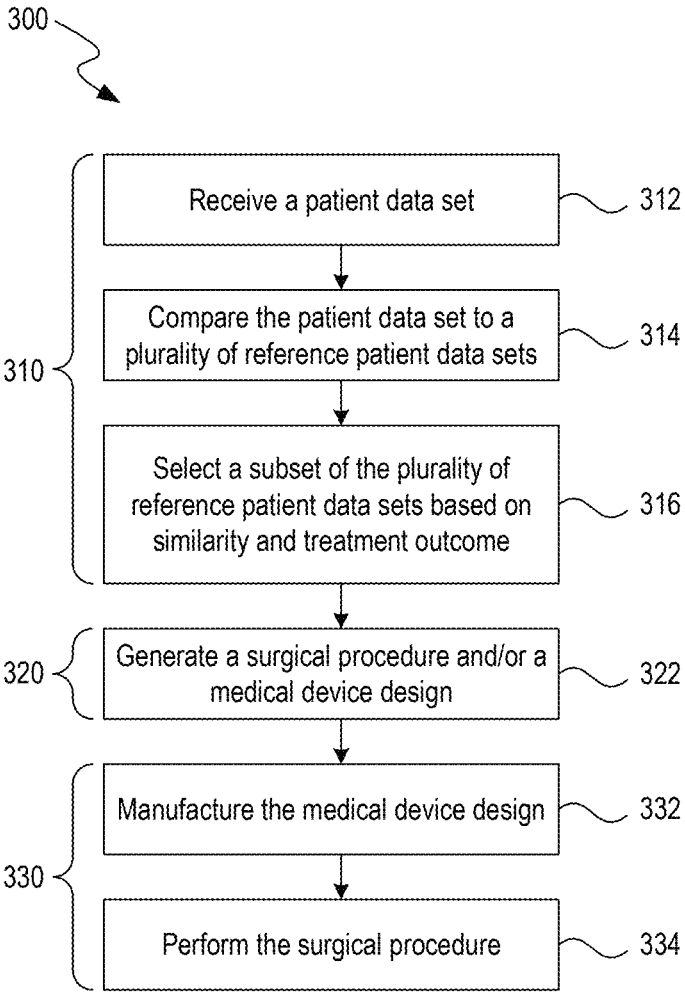
FIG. 3 is a flow diagram illustrating a method for providing patient-specific medical care, according to an embodiment.

FIG. 3 is a flow diagram illustrating a method 300 for providing patient-specific medical care, according to an embodiment. The method 300 can include a data phase 310, a modeling phase 320, and an execution phase 330. The data phase 310 can include collecting data of a patient to be treated (e.g., pathology data), and comparing the patient data to reference data (e.g., prior patient data such as pathology, surgical, and/or outcome data). For example, a patient data set can be received (block 312). The patient data set can be compared to a plurality of reference patient data sets (block 314), e.g., in order to identify one or more similar patient data sets in the plurality of reference patient data sets. Each of the plurality of reference patient data sets can include data representing one or more of age, gender, BMI, lumbar lordosis, Cobb angle(s), pelvic incidence, disc height, coronal offset distance, segment flexibility, LL-PI is greater than predetermined degrees (e.g., 5 degrees, 10 degrees, etc.), LL-PI mismatch (e.g., age-adjusted), sagittal vertical axis offset distance, coronal offset distance, coronal angle, bone quality, rotational displacement, or treatment level of the spine.

A subset of the plurality of reference patient data sets can be selected (block 316), e.g., based on similarity to the patient data set and/or treatment outcomes of the corresponding reference patients. For example, a similarity score can be generated for each reference patient data set, based on the comparison of the patient data set and the reference patient data set. The similarity score can represent a statistical correlation between the patient data and the reference patient data set. One or more similar patient data sets can be identified based, at least partly, on the similarity score.

In some embodiments, each patient data set of the selected subset includes and/or is associated with data indicative of a favorable treatment outcome (e.g., a favorable treatment outcome based on a single target outcome, aggregate outcome score, outcome thresholding). The data can include, for example, data representing one or more of corrected anatomical metrics, presence of fusion, health related quality of life, activity level, or complications. In some embodiments, the data is or includes an outcome score, which can be calculated based on a single target outcome, an aggregate outcome, and/or an outcome threshold.

Optionally, the data analysis phase 310 can include identifying or determining, for at least one patient data set of the selected subset (e.g., for at least one similar patient data set), surgical procedure data and/or medical device design data associated with the favorable treatment outcome. The surgical procedure data can include data representing one or more of a surgical approach, a corrective maneuver, a bony resection, or implant placement. The at least one medical device design can include data representing one or more of physical properties, mechanical properties, or biological properties of a corresponding medical device. In some embodiments, the at least one patient-specific medical device design includes a design for an implant or an implant delivery instrument.

In the modeling phase 320, a surgical procedure and/or medical device design is generated (block 322). The generating step can include developing at least one predictive model based on the patient data set and/or selected subset of reference patient data sets (e.g., using statistics, machine learning, neural networks, AI, or the like). The predictive model can be configured to generate the surgical procedure and/or medical device design.

In some embodiments, the predictive model includes one or more trained machine learning models that generate, at least partly, the surgical procedure and/or medical device design. For example, the trained machine learning model(s) can determine a plurality of candidate surgical procedures and/or medical device designs for treating the patient. Each surgical procedure can be associated with a corresponding medical device design. In some embodiments, the surgical procedures and/or medical device designs are determined based on surgical procedure data and/or medical device design data associated with favorable outcomes, as previously described with respect to the data analysis phase 310. For each surgical procedure and/or corresponding medical device design, the trained machine learning model(s) can calculate a probability of achieving a target outcome (e.g., favorable or desired outcome) for the patient. The trained machine learning model(s) can then select at least one surgical procedure and/or corresponding medical device design based, at least partly, on the calculated probabilities.

The execution phase 330 can include manufacturing the medical device design (block 332). In some embodiments, the medical device design is manufactured by a manufacturing system configured to perform one or more of additive manufacturing, 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing. The execution phase 330 can optionally include generating fabrication instructions configured to cause the manufacturing system to manufacture a medical device having the medical device design.

The execution phase 330 can include performing the surgical procedure (block 334). The surgical procedure can involve implanting a medical device having the medical device design into the patient. The surgical procedure can be performed manually, by a surgical robot, or a combination thereof. In embodiments where the surgical procedure is performed by a surgical robot, the execution phase 330 can include generating control instructions configured to cause the surgical robot to perform, at least partly, the patient-specific surgical procedure.

The method 300 can be implemented and performed in various ways. In some embodiments, one or more steps of the method 300 (e.g., the data phase 310 and/or the modeling phase 320) can be implemented as computer-readable instructions stored in memory and executable by one or more processors of any of the computing devices and systems described herein (e.g., the system 100), or a component thereof (e.g., the client computing device 102 and/or the server 106). Alternatively, one or more steps of the method 300 (e.g., the execution phase 330) can be performed by a healthcare provider (e.g., physician, surgeon), a robotic apparatus (e.g., a surgical robot), a manufacturing system (e.g., manufacturing system 124), or a combination thereof. In some embodiments, one or more steps of the method 300 are omitted (e.g., the execution phase 330).

Figure 4A:
FIGS. 4A-4C illustrate exemplary data sets that may be used and/or generated in connection with the methods described herein, according to an embodiment.
Figure 4B:
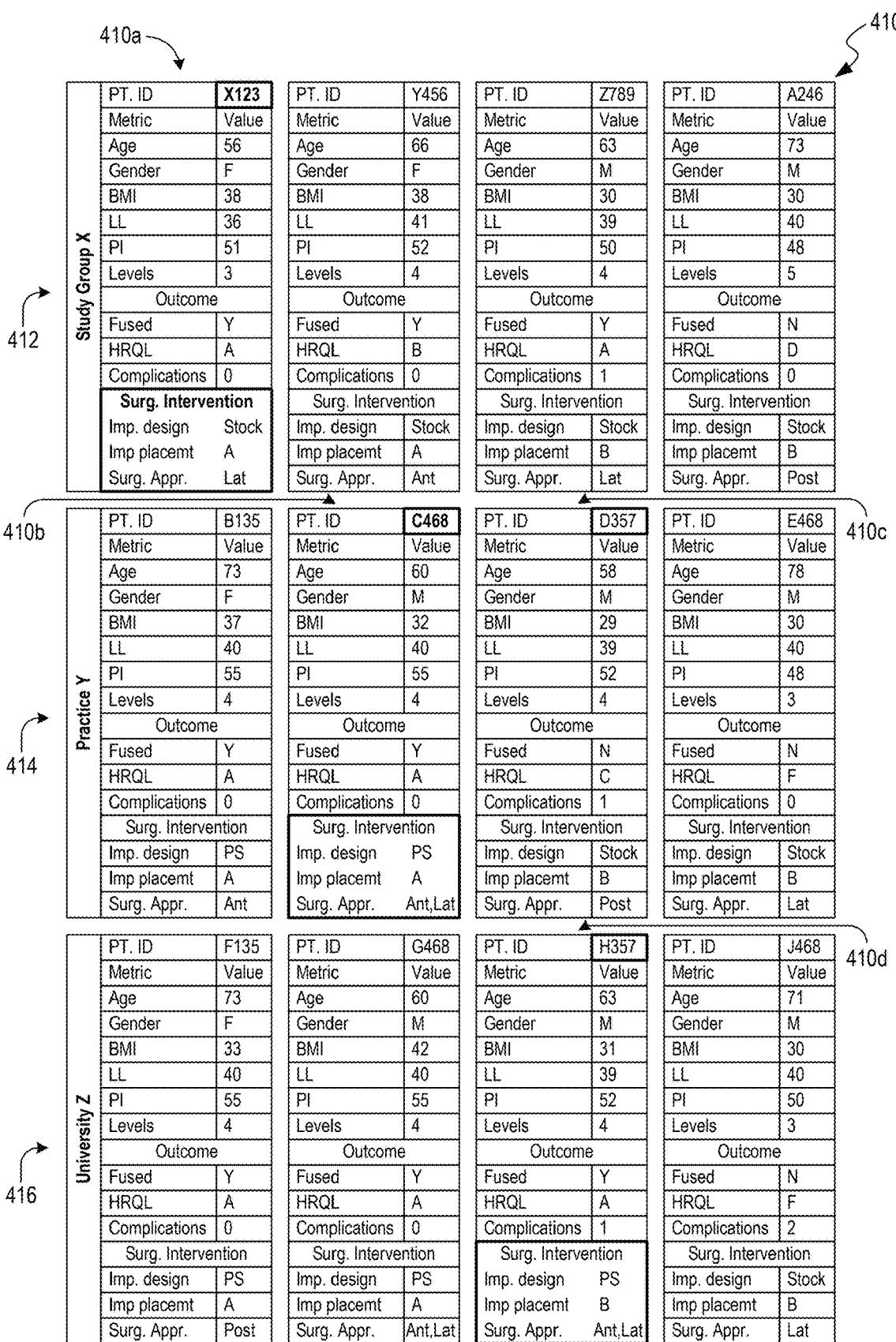
Figure 4C:
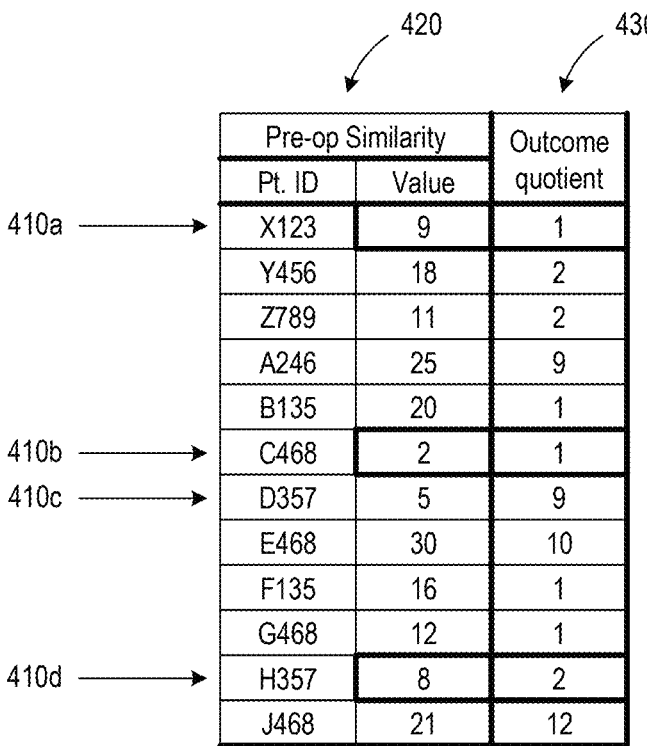

FIGS. 4A-4C illustrate exemplary data sets that may be used and/or generated in connection with the methods described herein (e.g., the data analysis phase 310 described with respect to FIG. 3), according to an embodiment. FIG. 4A illustrates a patient data set 400 of a patient to be treated. The patient data set 400 can include a patient ID and a plurality of pre-operative patient metrics (e.g., age, gender, BMI, lumbar lordosis (LL), pelvic incidence (PI), and treatment levels of the spine (levels)). FIG. 4B illustrates a plurality of reference patient data sets 410. In the depicted embodiment, the reference patient data sets 410 include a first subset 412 from a study group (Study Group X), a second subset 414 from a practice database (Practice Y), and a third subset 416 from an academic group (University Z). In alternative embodiments, the reference patient data sets 410 can include data from other sources, as previously described herein. Each reference patient data set can include a patient ID, a plurality of pre-operative patient metrics (e.g., age, gender, BMI, lumbar lordosis (LL), pelvic incidence (PI), and treatment levels of the spine (levels)), treatment outcome data (Outcome) (e.g., presence of fusion (fused), HRQL, complications), and treatment procedure data (Surg. Intervention) (e.g., implant design, implant placement, surgical approach).

FIG. 4C illustrates comparison of the patient data set 400 to the reference patient data sets 410. As previously described, the patient data set 400 can be compared to the reference patient data sets 410 to identify one or more similar patient data sets from the reference patient data sets. In some embodiments, the patient metrics from the reference patient data sets 410 are converted to numeric values and compared the patient metrics from the patient data set 400 to calculate a similarity score 420 ("Pre-op Similarity") for each reference patient data set. Reference patient data sets having a similarity score below a threshold value can be considered to be similar to the patient data set 400. For example, in the depicted embodiment, reference patient data set 410a has a similarity score of 9, reference patient data set 410b has a similarity score of 2, reference patient data set 410c has a similarity score of 5, and reference patient data set 410d has a similarity score of 8. Because each of these scores are below the threshold value of 10, reference patient data sets 410a-d are identified as being similar patient data sets.

The treatment outcome data of the similar patient data sets 410a-d can be analyzed to determine surgical procedures and/or implant designs with the highest probabilities of success. For example, the treatment outcome data for each reference patient data set can be converted to a numerical outcome score 430 ("Outcome Quotient") representing the likelihood of a favorable outcome. In the depicted embodiment, reference patient data set 410a has an outcome score of 1, reference patient data set 410b has an outcome score of 1, reference patient data set 410c has an outcome score of 9, and reference patient data set 410d has an outcome score of 2. In embodiments where a lower outcome score correlates to a higher likelihood of a favorable outcome, reference patient data sets 410a, 410b, and 410d can be selected. The treatment procedure data from the selected reference patient data sets 410a, 410b, and 410d can then be used to determine at least one surgical procedure (e.g., implant placement, surgical approach) and/or implant design that is likely to produce a favorable outcome for the patient to be treated.

In some embodiments, a method for providing medical care to a patient is provided. The method can include comparing a patient data set to reference data. The patient data set and reference data can include any of the data types described herein. The method can include identifying and/or selecting relevant reference data (e.g., data relevant to treatment of the patient, such as data of similar patients and/or data of similar treatment procedures), using any of the techniques described herein. A treatment plan can be generated based on the selected data, using any of the techniques described herein. The treatment plan can include one or more treatment procedures (e.g., surgical procedures, instructions for procedures, models or other virtual representations of procedures), one or more medical devices (e.g., implanted devices, instruments for delivering devices, surgical kits), or a combination thereof.

In some embodiments, a system for generating a medical treatment plan is provided. The system can compare a patient data set to a plurality of reference patient data sets, using any of the techniques described herein. A subset of the plurality of reference patient data sets can be selected, e.g., based on similarity and/or treatment outcome, or any other technique as described herein. A medical treatment plan can be generated based at least in part on the selected subset, using any of the techniques described herein. The medical treatment plan can include one or more treatment procedures, one or more medical devices, or any of the other aspects of a treatment plan described herein, or combinations thereof.

In further embodiments, a system is configured to use historical patient data. The system can select historical patient data to develop or select a treatment plan, design medical devices, or the like. Historical data can be selected based on one or more similarities between the present patient and prior patients to develop a prescriptive treatment plan designed for desired outcomes. The prescriptive treatment plan can be tailored for the present patient to increase the likelihood of the desired outcome. In some embodiments, the system can analyze and/or select a subset of historical data to generate one or more treatment procedures, one or more medical devices, or a combination thereof. In some embodiments, the system can use subsets of data from one or more groups of prior patients, with favorable outcomes, to produce a reference historical data set used to, for example, design, develop or select the treatment plan, medical devices, or combinations thereof.

Figure 5:
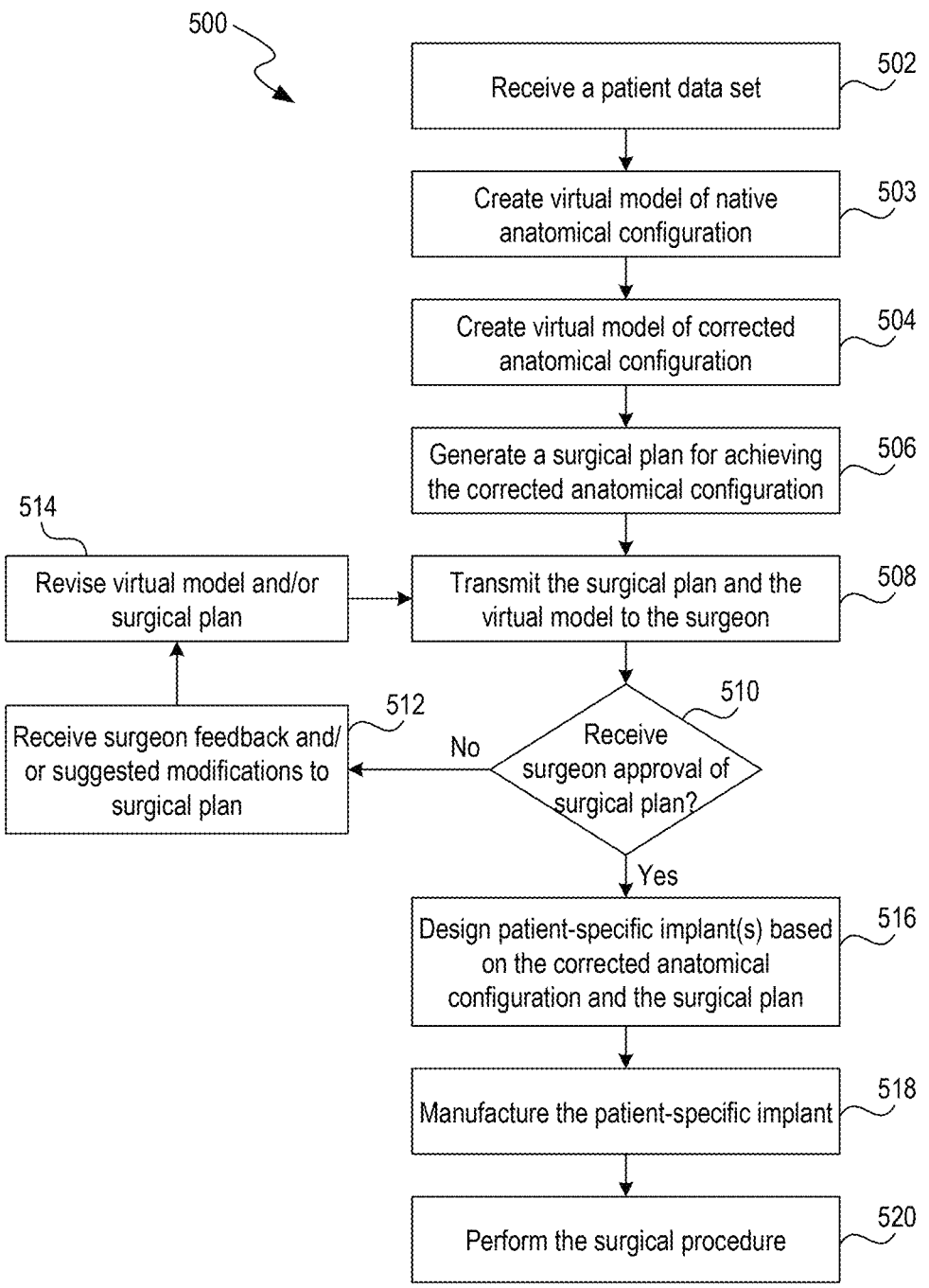
FIG. 5 is a flow diagram illustrating another method for providing patient-specific medical care, according to an embodiment.

FIG. 5 is a flow diagram illustrating a method 500 for providing patient-specific medical care, according to another embodiment of the present technology. The method 500 can begin in step 502 by receiving a patient data set for a particular patient in need of medical treatment. The patient data set can include data representative of the patient's condition, anatomy, pathology, symptoms, medical history, preferences, intra-operative data, and/or any other information or parameters relevant to the patient. For example, the patient data set 850 can include surgical intervention data, treatment outcome data, progress data (e.g., surgeon notes), patient feedback (e.g., feedback acquired using quality of life questionnaires, surveys), clinical data, patient information (e.g., demographics, sex, age, height, weight, type of pathology, occupation, activity level, tissue information, health rating, comorbidities, health related quality of life (HRQL)), vital signs, diagnostic results, medication information, allergies, diagnostic equipment information (e.g., manufacturer, model number, specifications, user-selected settings/configurations, etc.) or the like. The patient data set can also include image data, such as camera images, Magnetic Resonance Imaging (MRI) images, ultrasound images, Computerized Aided Tomography (CAT) scan images, Positron Emission Tomography (PET) images, X-Ray images, and the like. In some embodiments, the patient data set includes data representing one or more of patient identification number (ID), age, gender, body mass index (BMI), lumbar lordosis, Cobb angle(s), pelvic incidence, disc height, segment flexibility, bone quality, rotational displacement, and/or treatment level of the spine. The patient data set can be received at a server, computing device, or other computing system. For example, in some embodiments the patient data set can be received by the server 106 shown in FIG. 1. In some embodiments, the computing system that receives the patient data set in step 502 also stores one or more software modules (e.g., the data analysis module 116 and/or the treatment planning module 118, shown in FIG. 1, or additional software modules for performing various operations of the method 500). Additional details for collecting and receiving the patient data set are described below with respect to FIGS. 6-7D.

In some embodiments, the received patient data set can include disease metrics such as lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine). In some embodiments, the disease metrics are not included in the patient data set, and the method 500 includes determining (e.g., automatically determining) one or more of the disease metrics based on the patient image data, as described below.

Once the patient data set is received in step 502, the method 500 can continue in step 503 by creating a virtual model of the patient's native anatomical configuration (also referred to as "pre-operative anatomical configuration"). The virtual model can be based on the image data included in the patient data set received in step 502. For example, the same computing system that received the patient data set in step 502 can analyze the image data in the patient data set to generate a virtual model of the patient's native anatomical configuration. The virtual model can be a two- or three-dimensional visual representation of the patient's native anatomy. The virtual model can include one or more regions of interest, and may include some or all of the patient's anatomy within the regions of interest (e.g., any combination of tissue types including, but not limited to, bony structures, cartilage, soft tissue, vascular tissue, nervous tissue, etc.). As a non-limiting example, the virtual model can include a visual representation of the patient's spinal cord region, including some or all of the sacrum, lumbar region, thoracic region, and/or cervical region. In some embodiments, the virtual model includes soft tissue, cartilage, and other non-bony structures. In other embodiments, the virtual model only includes the patient's bony structures. An example of a virtual model of the native anatomical configuration is described below with respect to FIGS. 8A and 8B. In some embodiments, the method 500 can optionally omit creating a virtual model of the patient's native anatomy in step 503, and proceed directly from step 502 to step 504.

In some embodiments, the computing system that generated the virtual model in step 502 can also determine (e.g., automatically determine or measure) one or more disease metrics of the patient based on the virtual model. For example, the computing system may analyze the virtual model to determine the patient's pre-operative lumbar lordosis, Cobb angles, coronal parameters (e.g., coronal balance, global coronal balance, coronal pelvic tilt, etc.), sagittal parameters (e.g., pelvic incidence, sacral slope, thoracic kyphosis, etc.) and/or pelvic parameters. The disease metrics can include micro-measurements (e.g., metrics associated with specific or individual segments of the patient's spine) and/or macro-measurements (e.g., metrics associated with multiple segments of the patient's spine).

The method 500 can continue in step 504 by creating a virtual model of a corrected anatomical configuration (which can also be referred to herein as the "planned configuration," "optimized geometry," "post-operative anatomical configuration," or "target outcome") for the patient. For example, the computing system can, using the analysis procedures described previously, determine a "corrected" or "optimized" anatomical configuration for the particular patient that represents an ideal surgical outcome for the particular patient. This can be done, for example, by analyzing a plurality of reference patient data sets to identify post-operative anatomical configurations for similar patients who had a favorable post-operative outcome, as previously described in detail with respect to FIGS. 1-4C (e.g., based on similarity of the reference patient data set to the patient data set and/or whether the reference patient had a favorable treatment outcome). This may also include applying one or more mathematical rules defining optimal anatomical outcomes (e.g., positional relationships between anatomic elements) and/or target (e.g., acceptable) post-operative metrics/design criteria (e.g., adjust anatomy so that the post-operative sagittal vertical axis is less than 7 mm, the post-operative Cobb angle less than 10 degrees, etc.). Target post-operative metrics can include, but are not limited to, target coronal parameters, target sagittal parameters, target pelvic incidence angle, target Cobb angle, target shoulder tilt, target iliolumbar angle, target coronal balance, target Cobb angle, target lordosis angle, and/or a target intervertebral space height. The different between the native anatomical configuration and the corrected anatomical configuration may be referred to as a "patient-specific correction" or "target correction."

Once the corrected anatomical configuration is determined, the computing system can generate a two- or three-dimensional visual representation of the patient's anatomy with the corrected anatomical configuration. As with the virtual model created in step 503, the virtual model of the patient's corrected anatomical configuration can include one or more regions of interest, and may include some or all of the patient's anatomy within the regions of interest (e.g., any combination of tissue types including, but not limited to, bony structures, cartilage, soft tissue, vascular tissue, nervous tissue, etc.). As a non-limiting example, the virtual model can include a visual representation of the patient's spinal cord region in a corrected anatomical configuration, including some or all of the sacrum, lumbar region, thoracic region, and/or cervical region. In some embodiments, the virtual model includes soft tissue, cartilage, and other non-bony structures. In other embodiments, the virtual model only includes the patient's bony structures. An example of a virtual model of the native anatomical configuration is described below with respect to FIGS. 9A-1-9B-2.

In step 504, images of the patient can be segmented to isolate separate anatomic elements of the anatomy of interest. The spatial relationships between the isolated anatomic elements can be modified to generate a target or corrected patient pathology. The modifications can be selected based on regulatory criteria, financial parameters, etc. Other techniques can be used to generate anatomical configurations based on the available patient data.

The method 500 can continue in step 506 by generating (e.g., automatically generating) a surgical plan for achieving the corrected anatomical configuration shown by the virtual model. The surgical plan can include pre-operative plans, operative plans, post-operative plans, and/or specific spine metrics associated with the optimal surgical outcome. For example, the surgical plans can include a specific surgical procedure for achieving the corrected anatomical configuration. In the context of spinal surgery, the surgical plan may include a specific fusion surgery (e.g., PLIF, ALIF, TLIF, LLIF, DLIF, XLIF, etc.) across a specific range of vertebral levels (e.g., L1-L4, L1-5, L3-T12, etc.). Of course, other surgical procedures may be identified for achieving the corrected anatomical configuration, such as non-fusion surgical approaches and orthopedic procedures for other areas of the patient. The surgical plan may also include one or more expected spine metrics (e.g., lumbar lordosis, Cobb angles, coronal parameters, sagittal parameters, and/or pelvic parameters) corresponding to the expected post-operative patient anatomy. The surgical plan can be generated by the same or different computing system that created the virtual model of the corrected anatomical configuration. In some embodiments, the surgical plan can also be based on one or more reference patient data sets as previously described with respect to FIGS. 1-4C. In some embodiments, the surgical plan can also be based at least in part on surgeon-specific preferences and/or outcomes associated with a specific surgeon performing the surgery. In some embodiments, more than one surgical plan is generated in step 506 to provide a surgeon with multiple options. An example of a surgical plan is described below with respect to FIG. 10.

After the virtual model of the corrected anatomical configuration is created in step 504 and the surgical plan is generated in step 506, the method 500 can continue in step 508 by transmitting the virtual model of the corrected anatomical configuration and the surgical plan, including interactive surgical plans, for surgeon review. In some embodiments, the virtual model and the surgical plan are transmitted as a surgical plan report, an example of which is described with respect to FIG. 11. In some embodiments, the same computing system used in steps 502-506 can transmit the virtual model and surgical plan to a computing device for surgeon review (e.g., the client computing device 102 described in FIG. 1). This can include directly transmitting the virtual model and the surgical plan to the computing device or uploading the virtual model and the surgical plan to a cloud or other storage system for subsequent downloading. Although step 508 describes transmitting the surgical plan and the virtual model to the surgeon, one skilled in the art will appreciate from the disclosure herein that images of the virtual model may be included in the surgical plan transmitted to the surgeon, and that the actual model need not be included (e.g., to decrease the file size being transmitted). Additionally, the information transmitted to the surgeon in step 508 may include the virtual model of the patient's native anatomical configuration (or images thereof) in addition to the virtual model of the corrected anatomical configuration. In embodiments in which more than one surgical plan is generated in step 506, the method 500 can include transmitting more than one surgical plan to the surgeon for review and selection.

The surgeon can review the virtual model and surgical plan and, in step 510, either approve or reject the surgical plan (or, if more than one surgical plan is provided in step 508, select one of the provided surgical plans). If the surgeon does not approve the surgical plan in step 510, the surgeon can optionally provide feedback and/or suggested modifications to the surgical plan (e.g., by adjusting the virtual model or changing one or more aspects about the plan). Accordingly, the method 500 can include receiving (e.g., via the computing system) the surgeon feedback and/or suggested modifications. If surgeon feedback and/or suggested modifications are received in step 512, the method 500 can continue in step 514 by revising (e.g., automatically revising via the computing system) the virtual model and/or surgical plan based at least in part on the surgeon feedback and/or suggested modifications received in step 512. In some embodiments, the surgeon does not provide feedback and/or suggested modifications if they reject the surgical plan. In such embodiments, step 512 can be omitted, and the method 500 can continue in step 514 by revising (e.g., automatically revising via the computing system) the virtual model and/or the surgical plan by selecting new and/or additional reference patient data sets. The revised virtual model and/or surgical plan can then be transmitted to the surgeon for review. Steps 508, 510, 512, and 514 can be repeated as many times as necessary until the surgeon approves the surgical plan. Although described as the surgeon reviewing, modifying, approving, and/or rejecting the surgical plan, in some embodiments the surgeon can also review, modify, approve, and/or reject the corrected anatomical configuration shown via the virtual model.

Once surgeon approval of the surgical plan is received in step 510, the method 500 can continue in step 516 by designing (e.g., via the same computing system that performed steps 502-514) a patient-specific implant based on the corrected anatomical configuration and the surgical plan. The implant(s) (e.g., implants 154 or 161 of FIG. 1) can be designed by mapping a negative space between the anatomic elements and filling at least a portion of the negative space with a medical virtual implant. U.S. application Ser. No. 16/569,494 discloses techniques for generating corrected patient pathologies, mapping spaces, designing implants, and manufacturing implants. U.S. application Ser. No. 16/569,494 is incorporated by reference in its entirety.

The patient-specific implant can be specifically designed such that, when it is implanted in the particular patient, it directs the patient's anatomy to occupy the corrected anatomical configuration (e.g., transforming the patient's anatomy from the native anatomical configuration to the corrected anatomical configuration). The patient-specific implant can be designed such that, when implanted, it causes the patient's anatomy to occupy the corrected anatomical configuration for the expected service life of the implant (e.g., 5 years or more, 10 years or more, 20 years or more, 50 years or more, etc.). In some embodiments, the patient-specific implant is designed solely based on the virtual model of the corrected anatomical configuration and/or without reference to pre-operative patient images.

The patient-specific implant can be any of the implants described herein or in any patent references incorporated by reference herein. For example, the patient-specific implant can include one or more of screws (e.g., bone screws, spinal screws, pedicle screws, facet screws), interbody implant devices (e.g., intervertebral implants), cages, plates, rods, discs, fusion devices, spacers, rods, expandable devices, stents, brackets, ties, scaffolds, fixation device, anchors, nuts, bolts, rivets, connectors, tethers, fasteners, joint replacements (e.g., artificial discs), hip implants, or the like. A patient-specific implant design can include data representing one or more of physical properties (e.g., size, shape, volume, material, mass, weight), mechanical properties (e.g., stiffness, strength, modulus, hardness), and/or biological properties (e.g., osteo-integration, cellular adhesion, anti-bacterial properties, anti-viral properties) of the implant. For example, a design for an orthopedic implant can include implant shape, size, material, and/or effective stiffness (e.g., lattice density, number of struts, location of struts, etc.). An example of a patient-specific implant designed via the method 500 is described below with respect to FIGS. 12A and 12B.

In some embodiments, designing the implant in step 516 can optionally include generating fabrication instructions for manufacturing the implant. For example, the computing system may generate computer-executable fabrication instructions that that, when executed by a manufacturing system, cause the manufacturing system to manufacture the implant. For example, a virtual 3D model of the one or more patient-specific implants can be created based on filling of negative spaces between anatomical elements of the corrected patient pathology. The virtual 3D model can be converted into 3D fabrication data for manufacturing the one or more patient-specific implants.

In some embodiments, the patient-specific implant is designed in step 516 only after the surgeon has reviewed and approved the virtual model with the corrected anatomical configuration and the surgical plan. Accordingly, in some embodiments, the implant design is neither transmitted to the surgeon with the surgical plan in step 508, nor manufactured before receiving surgeon approval of the surgical plan. Without being bound by theory, waiting to design the patient-specific implant until after the surgeon approves the surgical plan may increase the efficiency of the method 500 and/or reduce the resources necessary to perform the method 500.

The method 500 can continue in step 518 by manufacturing the patient-specific implant. The implant can be manufactured using additive manufacturing techniques, such as 3D printing, stereolithography, digital light processing, fused deposition modeling, selective laser sintering, selective laser melting, electronic beam melting, laminated object manufacturing, powder bed printing, thermoplastic printing, direct material deposition, or inkjet photo resin printing, or like technologies, or combination thereof. Alternatively or additionally, the implant can be manufactured using subtractive manufacturing techniques, such as CNC machining, electrical discharge machining (EDM), grinding, laser cutting, water jet machining, manual machining (e.g., milling, lathe/turning), or like technologies, or combinations thereof. The implant may be manufactured by any suitable manufacturing system (e.g., the manufacturing system 124 shown in FIG. 1). In some embodiments, the implant is manufactured by the manufacturing system executing the computer-readable fabrication instructions generated by the computing system in step 516.

Once the implant is manufactured in step 518, the method 500 can continue in step 520 by implanting the patient-specific implant into the patient. The surgical procedure can be performed manually, by a robotic surgical platform (e.g., a surgical robot), or a combination thereof. In embodiments in which the surgical procedure is performed at least in part by a robotic surgical platform, the surgical plan can include computer-readable control instructions configured to cause the surgical robot to perform, at least partly, the patient-specific surgical procedure.

The method 500 can be implemented and performed in various ways. In some embodiments, steps 502-516 can be performed by a computing system associated with a first entity, step 518 can be performed by a manufacturing system associated with a second entity, and step 520 can be performed by a surgical provider, surgeon, and/or robotic surgical platform associated with a third entity. During the surgical procedure, method 500 can collect intra-operative data. Any of the foregoing steps may also be implemented as computer-readable instructions stored in memory and executable by one or more processors of the associated computing system(s). In some implementations, steps 502-514 are performed with intra-operative data to provide confirmation that the location and position of the implant during a surgical procedure is within a threshold (e.g., delta threshold) of the pre-operative plan.

Figure 6A:
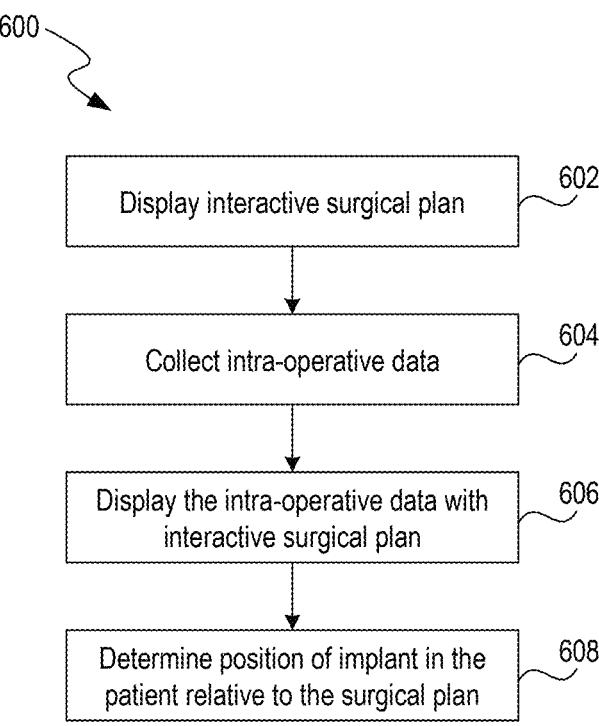
FIGS. 6A and 6B are flow diagrams illustrating methods for providing confirmation of intra-operative positioning of surgical implants, according to an embodiment.

FIG. 6A is a flow diagram illustrating a method 600 for providing confirmation of intra-operative positioning of surgical implants, according to another embodiment of the present technology.

The method 600 can begin in step 602 by displaying an interactive plan generated based on patient data. A patient-specific interactive surgical plan (e.g., plan 132 of FIG. 1, plan 1000 of FIG. 10A, plan 1020 of FIG. 10B, or overlaid image 1060 of FIG. 10C) includes a viewable planned pathology for the patient and is configured to receive user input. The pre-operative and/or intra-operative pathology can be used to validate a diagnosis, qualifying conditions for treatment, or the like based on pre-operative measurements, such as lumbar lordosis, Cobb angle(s), pelvic incidence, disc height(s), coronal offset distance, segment flexibility, LL-PI is greater than predetermined degrees (e.g., 5 degrees, 10 degrees, 15 degrees, etc.), LL-PI mismatch (e.g., age-adjusted), sagittal vertical axis offset distance, coronal offset distance, coronal angle, bone quality, and other metrics disclosed herein. Example displayed interactive plans and viewable pathologies are discussed in connection with FIGS. 7A-11.

The method 600 can continue in step 604 by collecting intra-operative data during a procedure involving a patient-specific implant. For example, a device (e.g., fluoroscopy device, radiographic device, C-Arm device, ultrasound device, MRI device, X-Ray device, tablet, camera, etc.) can capture intra-operative data (e.g., continuous imaging, images, etc.) of a patient during a procedure to install the implant in the patient. The method 600 can collect the intra-operative data randomly, periodically, continuously, or at designated stages of the procedure of installing an implant. In some implementations, the intra-operative data is collected continuously to create a "live" feed of the medical procedure.

In step 606, the method 600 can display the intra-operative data with the interactive surgical plan. For example, method 600 can overlay the intra-operative data on the pre-operative plan to illustrate any differences between the intra-operative data and the pre-operative plan. The intra-operative images and pre-operative images can be configured (adjusted) to be virtually overlaid on each other. In some embodiments, the method 600 can include overlaying portions of preoperative images onto the intra-operative images. The intra-operative images can be segmented to isolate anatomical elements. The segmented anatomical elements can be overlayed onto the pre-operative images to show differences between the planned and actual positions of anatomical elements. The method 600 can use machine learning or other algorithms to identify matching features in the intra-operative and pre-operative images. In other embodiments, the anatomical elements of pre-operative plans can be overlayed onto the intra-operative images. The facing and relative positions of the anatomical elements in the pre-operative images can be compared with the actual positions in the intra-operative images. The method 600 can compensate for loading conditions of the pre-operative images. For example, if the patient has pre-operative standing x-rays, the method 600 can modify the relative positions of anatomical elements based on the intra-operative loading of the patient. For example, if the patient is laying horizontally, the method 600 can move the anatomical elements of the pre-operative images to match an unloaded or laying down condition. Accordingly, pre-operative images can be manipulated or modified based on various loading conditions, patient positions, etc.

Method 600 can match landmarks (e.g., anatomical landmarks, implant landmarks, etc.), reference features, etc. to synchronize or nearly synchronize the intra-operative and pre-operative images. The landmarks can be selected by the system based upon individually identifiable anatomical elements. In some embodiments, a user can select and identify landmarks. For example, a user can review a surgical plan and identify one of more landmarks in pre-operative images, virtual models, images of anatomical models, or the like. The synchronization routine can be selected based on the desired accuracy of placement of the implant. If an implant is to be positioned near nerve tissue (e.g., the spinal cord), the user can select a synchronization routine to ensure that the implant is appropriately spaced apart from the spinal cord. Fixation elements (e.g., bone screws, fixation plates, etc.) can be used to limit or prevent migration of the implant post operation. Method 600 can use machine learning or artificial intelligence to align the images by zooming, stretching, and/or rotating the images on a viewing platform (e.g., user interface, screen, virtual model, etc.). In some implementations, method 600 compares the intra-operative data to the pre-operative plan and displays indications (e.g., tags, highlights, boxes, arrows, etc.) on the interactive surgical plan of any differences between the intra-operative data and pre-operative plan. In some embodiments, the method 600 allows a user to manipulate the images via viewing platform. For example, the user can manually zoom, stretch, crop, rotate, or otherwise manipulate images to achieve desired synchronization. The user can select images, adjust images, and control synchronization. In some embodiments, the method 600 includes analyzing manipulation of images performed by the user. The 600 can generate additional planned images by manipulating one or more pre-operative virtual models to generate additional images. This allows a user to review planned images that match the perspective and scale of intra-operative images. In fluoroscopic imaging, the method 600 can dynamically overlay pre-operative planned images onto continuous real-time fluoroscopic imaging. If the fluoroscopic imaging device is moved, the system can dynamically move the planned images to key those images to the fluoroscopic imaging. This allows the surgical team to obtain images of the patient from different viewing perspectives in real-time while continually viewing the targeted position for the implant.

In step 608, the method 600 can determine whether the position of the implant in the intra-operative data matches the placement in the pre-operative plan. Method 600 can determine if the position of the implant in the intra-operative data matches the placement in the pre-operative plan by determining if the orientation and location of the implant in the patient is the same as the pre-operative plan. The criteria for determining whether the intra-operative data matches a placement can be selected based on the procedure. In some embodiments, the criteria can be generated using machine learning, implemented by the user, or obtained from a database with matching recommendations. The criteria can include, for example, deviations, deltas, distance between intra-operative position and planned position, distances between the implant and anatomical elements (e.g., landmarks, nontargeted anatomical elements, nerves, etc.), interfaces (e.g., interfaces between the implant and anatomical elements, or combinations thereof), etc.

Figure 6B:
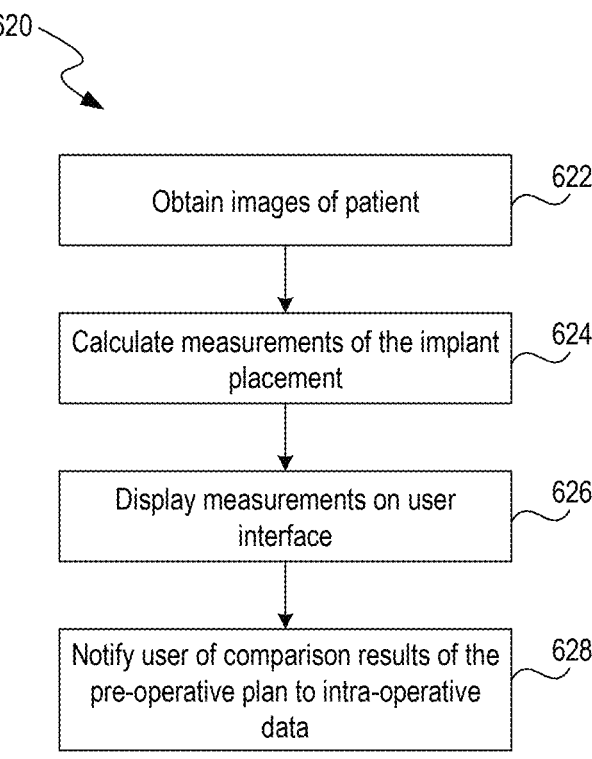
Figure 7D:
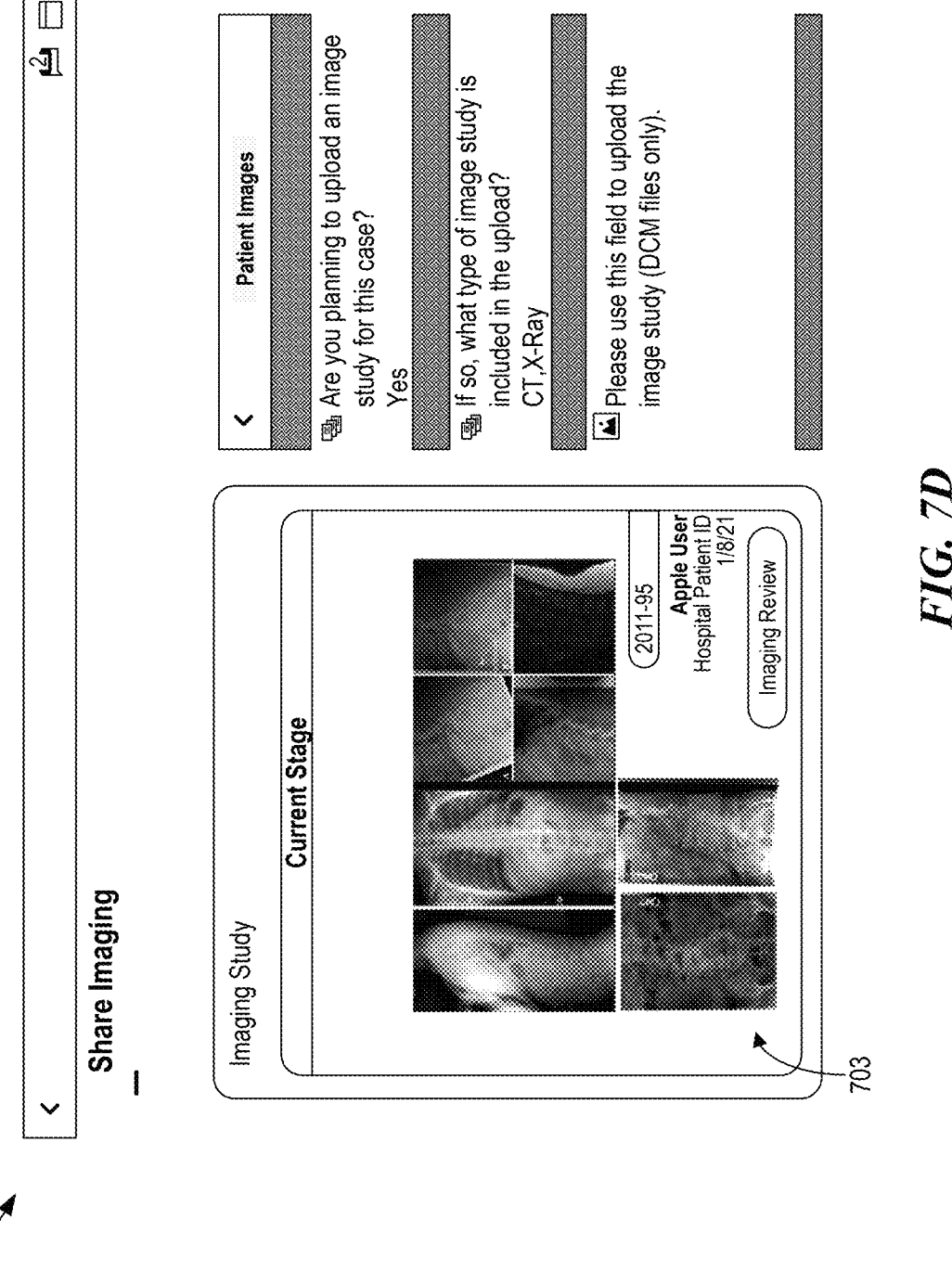

FIG. 6B is a flow diagram illustrating a method 620 for providing confirmation of intra-operative positioning of surgical implants, according to embodiments of the present technology. Steps of the method 620 can be implemented using treatment plans discussed in connection with FIGS. 10A-11. The method 620 can begin in step 622 by obtaining one or more images (e.g., intra-operative images, pre-operative images, etc.) of a patient. The images can include a planned position of an implant in a patient and an actual position of the implant in the placement.

In step 624, the method 620 can calculate measurements of the implant placement in the patient to determine whether the installed implant is at the position (e.g., location, orientation, etc.) that was determined in the pre-operative model (as described in step 503-516 of FIG. 5). The measurements can include coordinates of an implant in the patient's body. For example, the measurements are the distance of the implant from one or more anatomical elements (e.g., bones, organs, joints, etc.), landmarks, reference features (e.g., other implants), or any location on the patient.

In some implementations, the measurements are calculations of the difference (e.g., delta, deviation) between the intra-operative data and the pre-operative plan/model. The measurements can include degrees of rotation that the implant in the patient differs from the pre-operative plan, and/or the metric distance that the implant in the patient needs to move to align with the pre-operative plan. In some implementations, the measurements include a percentage calculation (e.g., 89%, 96%, etc.) that the intra-operative data aligns with the pre-operative plan. Method 620 can calculate a metric for the completion of the installation of the implant in the patient. Based on the severity of the patient's condition, a threshold completion percentage may be adjusted. Method 620 can notify the healthcare provider, when the threshold completion percentage is reached during an installation procedure.

In step 626, the method 620 can display the measurements on a user interface (e.g., display 122 of FIG. 1) for a user (e.g., healthcare provider) to view. Method 620 can display pre-operative and intra-operative metrics (e.g., pre-operative patient metrics or measurements 1002 and intra-operative patient metrics 1004 of FIG. 10A). Method 620 can display a comparison percentage (e.g., illustrated by notification 1022 of FIG. 10B) of the intra-operative data to the pre-operative plan. In some implementations, method 620 displays a metric for the completion (e.g., illustrated by notification 1024 of FIG. 10B) of the installation of the implant in the patient. Method 620 can display a live comparison (e.g., plan 1000 of FIG. 10A, plan 1020 of FIG. 10B, or overlaid image 1060 of FIG. 10D) of the intra-operative data to the pre-operative plan while a healthcare provider is installing an implant in a patient.

In step 628, method 620 can generate a notification of the results of the comparison of pre-operative plan to intra-operative data. Method 620 can notify a healthcare provider if the results differ a threshold amount from the pre-operative model. For example, if the location of the implant in the patient is threshold distance from where the implant located in the surgical plan, a user can receive a notification to adjust the position of the implant before completing the procedure.

Machine learning algorithms can be used perform one or more steps methods 600 of FIG. 6A and method 620 of FIG. 6B. For example, the SPC platform 109 of FIG. 1 can include a machine-learning model trained using the selected reference patient data sets. Patient images can be inputted into the trained machine-learning model to provide confirmation of intra-operative positioning of surgical implants based on the pre-operative plan. The machine learning model can be selected based on design goals, such as optimized patient outcomes.

FIGS. 7A-13 further illustrate select aspects of providing patient-specific medical care, e.g., in accordance with the method 500. For example, FIG. 7A-7D illustrate an example of a patient data set 700 (e.g., as received in step 502 of the method 500). The patient data set 700 can include any of the information previously described with respect to the patient data set. For example, the patient data set 700 includes patient information 701 (e.g., patient identification no., patient MRN, patient name, sex, age, body mass index (BMI), surgery date, surgeon, etc., shown in FIGS. 7A and 7B), diagnostic information 702 (e.g., Oswestry Disability Index (ODI), VAS-back score, VAS-leg score, Pre-operative pelvic incidence, pre-operative lumbar lordosis, pre-operative PI-LL angel, pre-operative lumbar coronal cobb, etc., shown in FIGS. 7B and 7C), and image data 703 (x-ray, CT, MRI, etc., shown in FIG. 7D). In the illustrated embodiment, the patient data set 700 is collected by a healthcare provider (e.g., a surgeon, a nurse, etc.) using a digital and/or fillable report that can be accessed using a computing device. In some embodiments, the patient data set 700 can be automatically or at least partially automatically generated based on digital medical records of the patient. Regardless, once collected, the patient data set 700 can be transmitted to the computing system configured to generate the surgical plan for the patient.

Figure 8A:
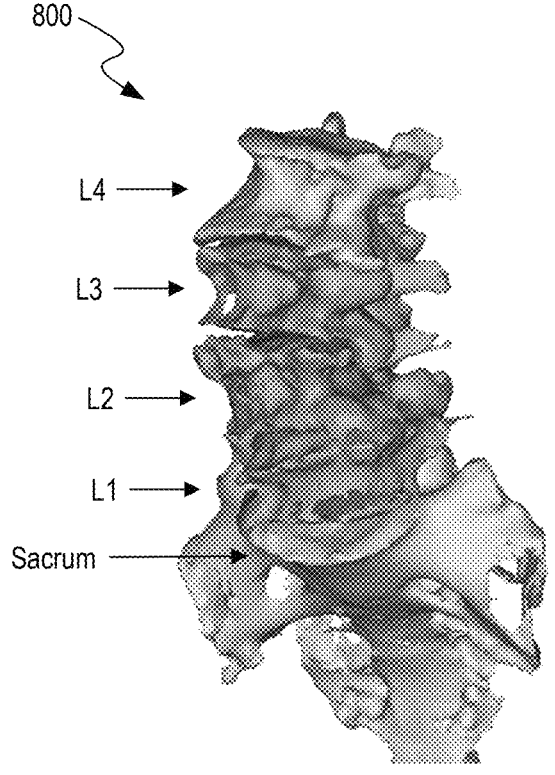
FIGS. 8A and 8B illustrate an exemplary virtual model of a patient's spine that may be used and/or generated in connection with the methods described herein, according to an embodiment.
Figure 8B:
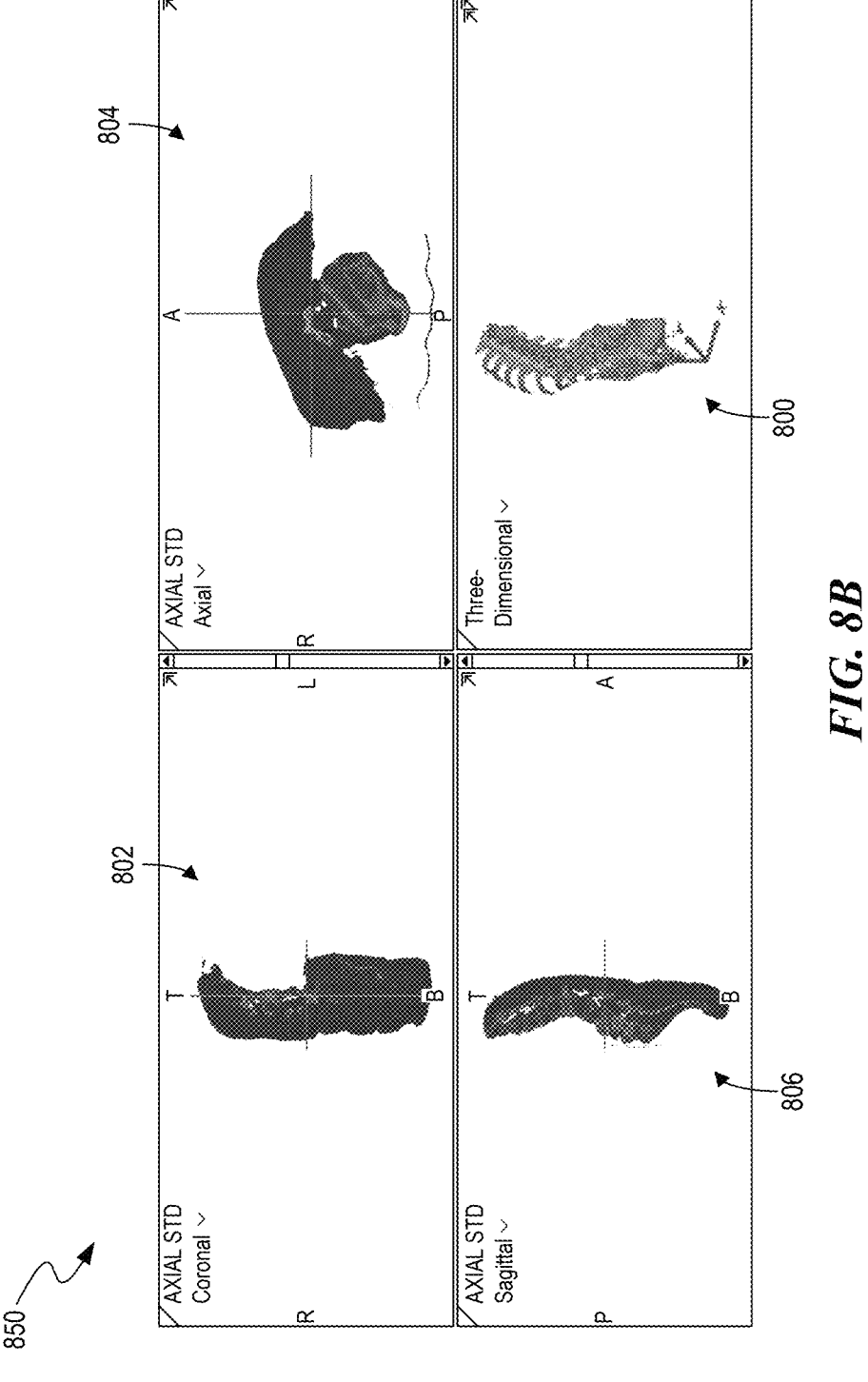

FIGS. 8A and 8B illustrate an example of a virtual model 800 of a patient's native anatomical configuration (e.g., as created in step 503 of the method 500). In particular, FIG. 8A is an enlarged view of the virtual model 800 of the patient's native anatomy and shows the patient's native anatomy of their lower spinal cord region. The virtual model 800 is a three-dimensional visual representation of the patient's native anatomy. In the illustrated embodiment, the virtual model includes a portion of the spinal column extending from the sacrum to the L4 vertebral level. Of course, the virtual model can include other regions of the patient's spinal column, including cervical vertebrae, thoracic vertebrae, lumbar vertebrae, and the sacrum. The illustrated virtual model 800 only includes bony structures of the patient's anatomy, but in other embodiments may include additional structures, such as cartilage, soft tissue, vascular tissue, nervous tissue, etc.

FIG. 8B illustrates a virtual model display 850 (referred to herein as the "display 850") showing different views of the virtual model 800. The virtual model display 850 includes a three-dimensional view of the virtual model 800, one or more coronal cross-section(s) 802 of the virtual model 800, one or more axial cross section(s) 804 of the virtual model 800, and/or one or more sagittal cross-section(s) 806 of the virtual model 800. Of course, other views are possible and can be included on the virtual model display 850. In some embodiments, the virtual model 800 may be interactive such that a user can manipulate the orientation or view of the virtual model 800 (e.g., rotate), change the depth of the displayed cross-sections, select and isolate specific bony structures, or the like.

Figures 1, 2, 9A:
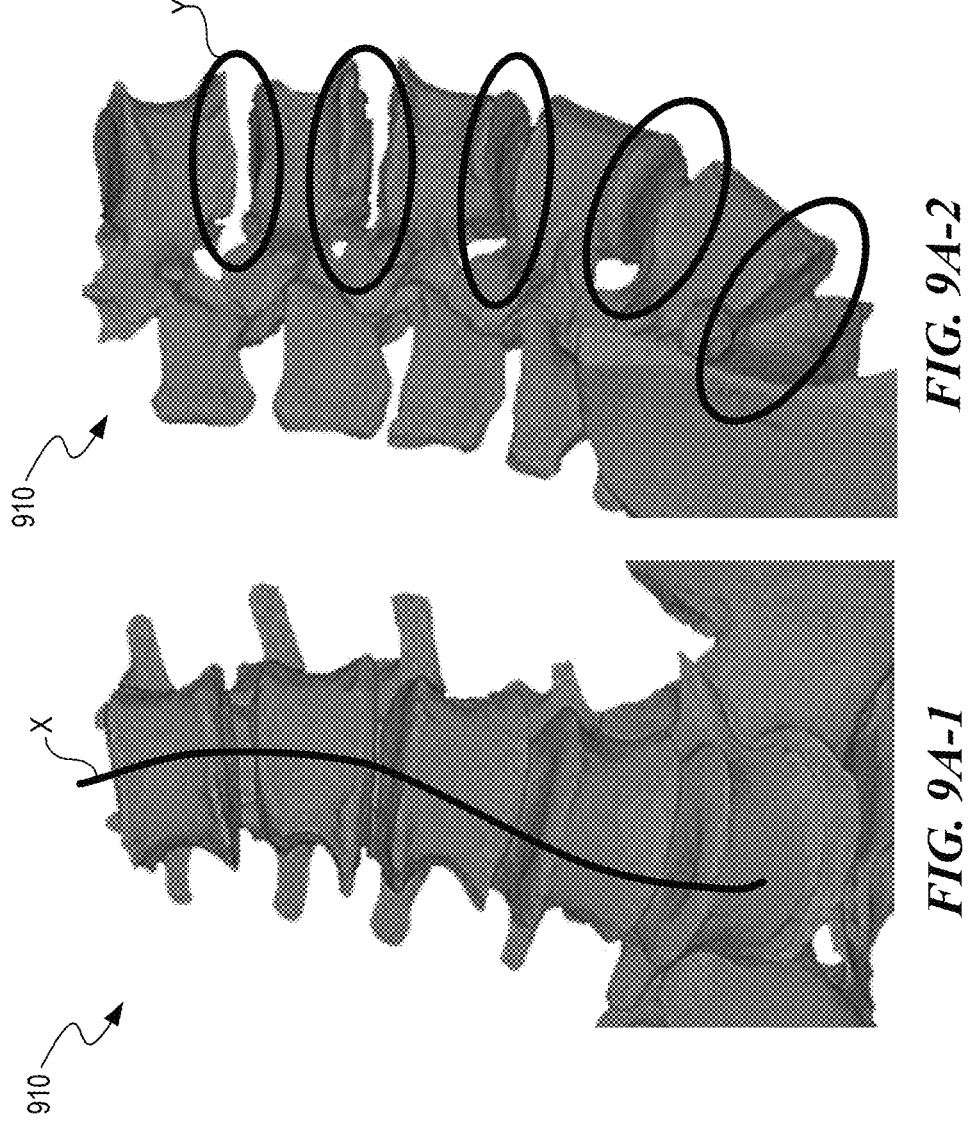
Figures 1, 2, 9B:
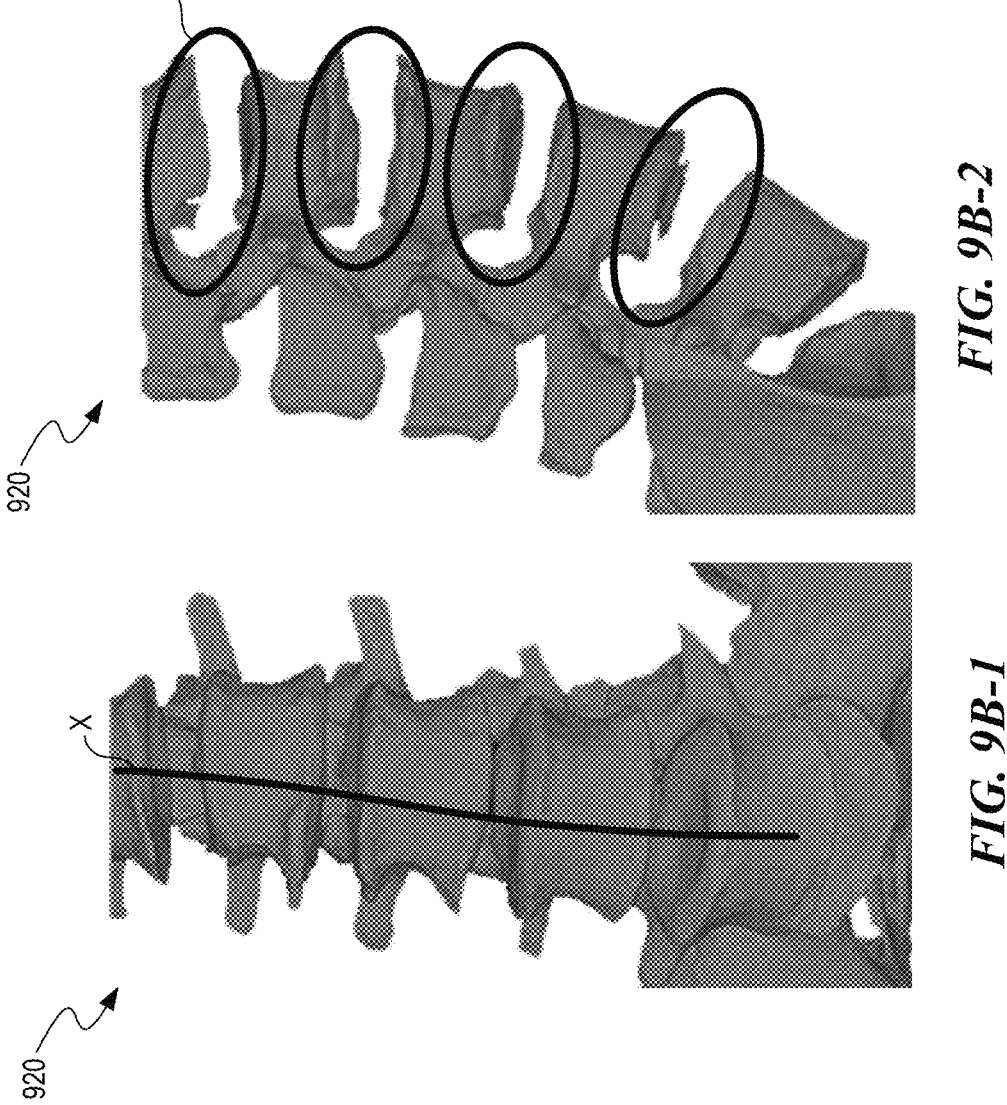

FIGS. 9A-1-9B-2 demonstrate an example of a virtual model of a patient's native anatomical configuration (e.g., as created in step 503 of the method 500) and a virtual model of the patient's corrected anatomical configuration (e.g., as created in step 504 of the method 500). In particular, FIGS. 9A-1 and 9A-2 are anterior and lateral views, respectively, of a virtual model 910 showing a native anatomical configuration of a patient, and FIGS. 9B-1 and 9B-2 are anterior and lateral views, respectively, of a virtual model 920 showing the corrected anatomical configuration for the same patient. Referring first to FIG. 9A-1, the anterior view of the virtual model 910 illustrates the patient has abnormal curvature (e.g., scoliosis) of their spinal column. This is marked by line X, which follows a rostral-caudal axis of the spinal column. Referring next to FIG. 9A-1, the lateral view of the virtual model 910 illustrates the patient has collapsed discs or decreased spacing between adjacent vertebral endplates, marked by ovals Y. FIGS. 9B-1 and 9B-2 illustrate the corrected virtual model 920 accounting for the abnormal anatomical configurations shown in FIGS. 9A-1 and 9A-2. For example, FIG. 9B-1, which is an anterior view of the virtual model 920, illustrates the patient's spinal column having corrected alignment (e.g., the abnormal curvature has been reduced). This correction is shown by line X, which also follows a rostral-caudal axis of the spinal column. FIG. 9B-2, which is a lateral view of the virtual model 920, illustrates the patient's spinal column having restored disc height (e.g., increased spacing between adjacent vertebral endplates), also marked by ovals Y. The lines X and the ovals Y are provided in FIGS. 9A-1-9B-2 to more clearly demonstrate the correction between the virtual models 910 and 920, and are not necessarily included on the virtual models generated in accordance with the present technology.

Figure 10A:
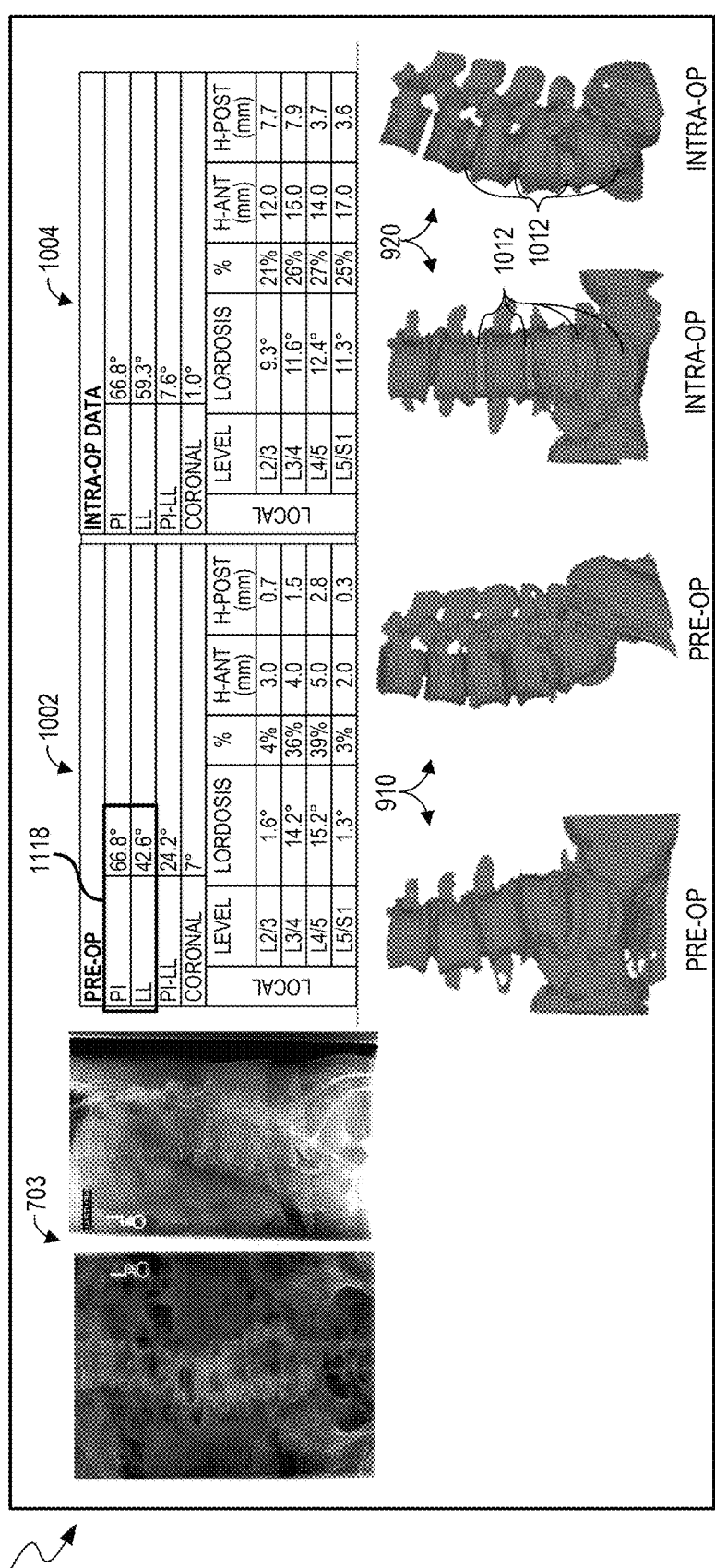
FIG. 10A illustrates an exemplary interactive surgical plan for a patient-specific surgical procedure, according to an embodiment.

FIG. 10A illustrates an example of a surgical plan 1000 (e.g., as generated in step 506 of the method 500, method 600 of FIG. 6A, or method 620 of FIG. 6B). The surgical plan 1000 can include pre-operative patient metrics or measurements 1002, intra-operative patient metrics 1004, one or more patient images (e.g., the patient images 703 received as part of the patient data set), the virtual model 910 (which can be the model itself or one or more images derived from the model) of the patient's native anatomical configuration (e.g., pre-operative patient anatomy), and/or the intra-operative virtual model 920 (which can be the model itself or one or more images derived from the model) of the patient's corrected anatomical configuration (e.g., intra-operative patient anatomy). The pre-operative patient metrics 1002 can include, without limitation, lumbar lordosis, Cobb angle(s), pelvic incidence, disc height, coronal offset distance, segment flexibility, LL-PI is greater than predetermined degrees (e.g., 5 degrees, 10 degrees, etc.), LL-PI mismatch (e.g., age-adjusted), sagittal vertical axis offset distance, coronal offset distance, coronal angle, bone quality, rotational displacement.

The virtual model 920 of the intra-operative patient anatomy can optionally include one or more implants 1012 shown as implanted in the patient's spinal cord region to demonstrate how patient anatomy will look following the surgery. Although four implants 1012 are shown in the virtual model 920, the surgical plan 1000 may include more or fewer implants 1012, including one, two, three, five, six, seven, eight, or more implants 1012.

The surgical plan 1000 can include additional information beyond what is illustrated in FIG. 10. For example, the surgical plan 1000 may include pre-operative instructions, operative instructions, and/or post-operative instructions. Operative instructions can include one or more specific procedures to be performed (e.g., PLIF, ALIF, TLIF, LLIF, DLIF, XLIF, etc.) and/or one or more specific targets of the operation (e.g., fusion of vertebral levels L1-L4, anchoring screw to be inserted in lateral surface of L4, etc.). Although the surgical plan 1000 is demonstrated in FIG. 10A as a visual report, the surgical plan 1000 can also be encoded in computer-executable instructions that, when executed by a processor connected to a computing device, cause the surgical plan 1000 to be displayed by the computing device. In some embodiments, the surgical plan 1000 may also include machine-readable operative instructions for carrying out the surgical plan. For example, the surgical plan can include operative instructions for a robotic surgical platform to carry out one or more steps of the surgical plan 1000.

Figure 10B:
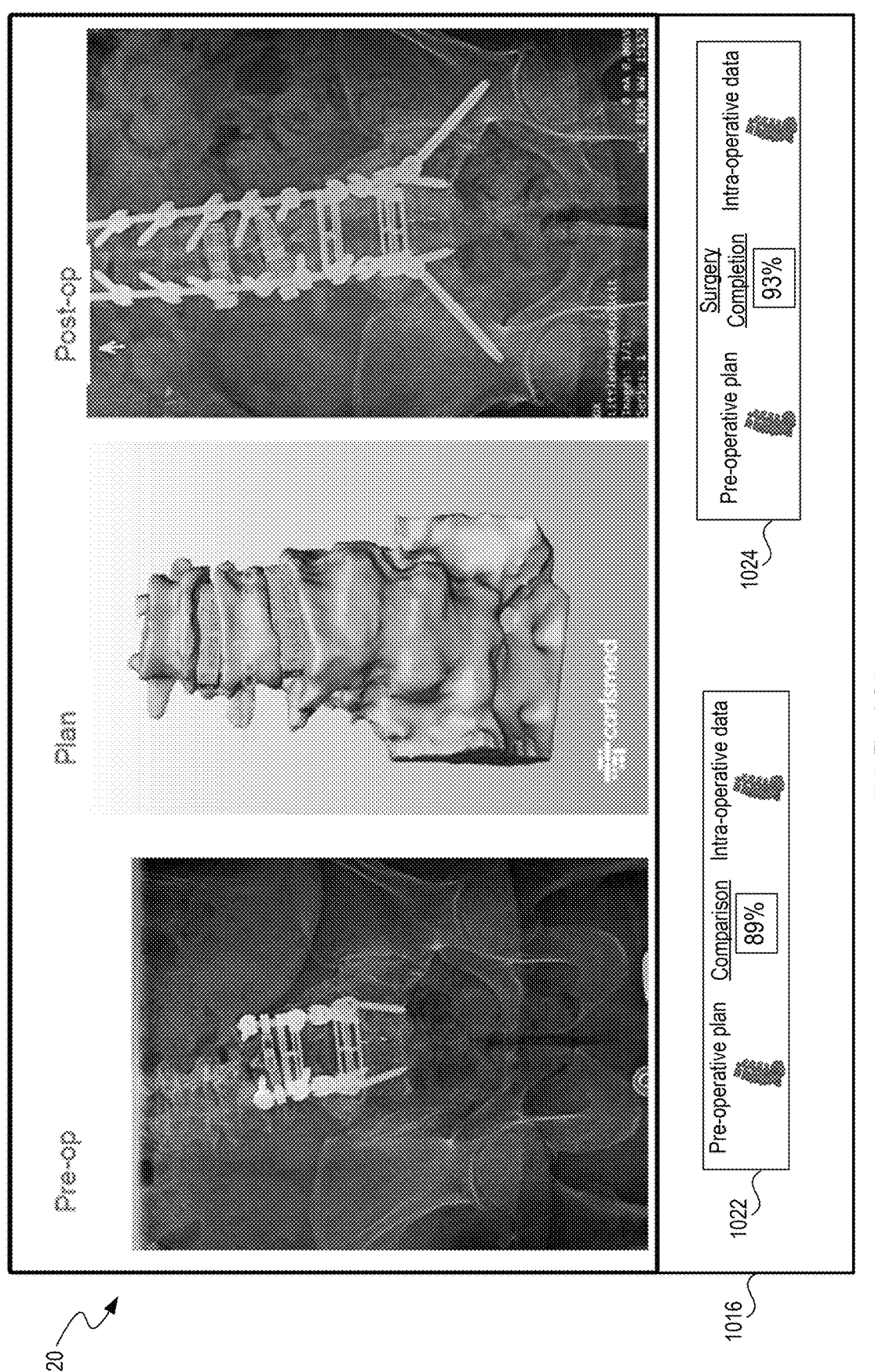
FIG. 10B illustrates pre-operative, plan, intra-operative, and post-operative images to allow for assessment of achievement of surgical goals, according to an embodiment.

FIG. 10B illustrates plan 1020 with a pre-operative imaging, pre-operative plan, intra-operative image, and post-operative image to allow for assessment of achievement of surgical goals, according to an embodiment. Plan 1020 can display a notification 1022 of a comparison percentage (e.g., 89%) of the intra-operative data to the pre-operative plan. Plan 1020 can display notification 1024 which is a metric of completion (e.g., 93%) of the installation of the implant in the patient. The pre-operative plan images can be generated based on one or more pre-operative images, virtual models (e.g., 3D virtual models), and/or other data disclosed herein. The data can be manipulated or modified to, for example, compensate for loading conditions by, for example, repositioning features in the virtual model to match intra-operative loading conditions. The planned image of FIG. 10B shows planned positions for anatomical elements of the patient. The planned image can also include additional features from the pre-operative image, such as the fixation system in the illustrated pre-operative image. The previously implanted fixation system can be used in the landmark for aligning the intra-operative images and the planned images.

Figure 10C:
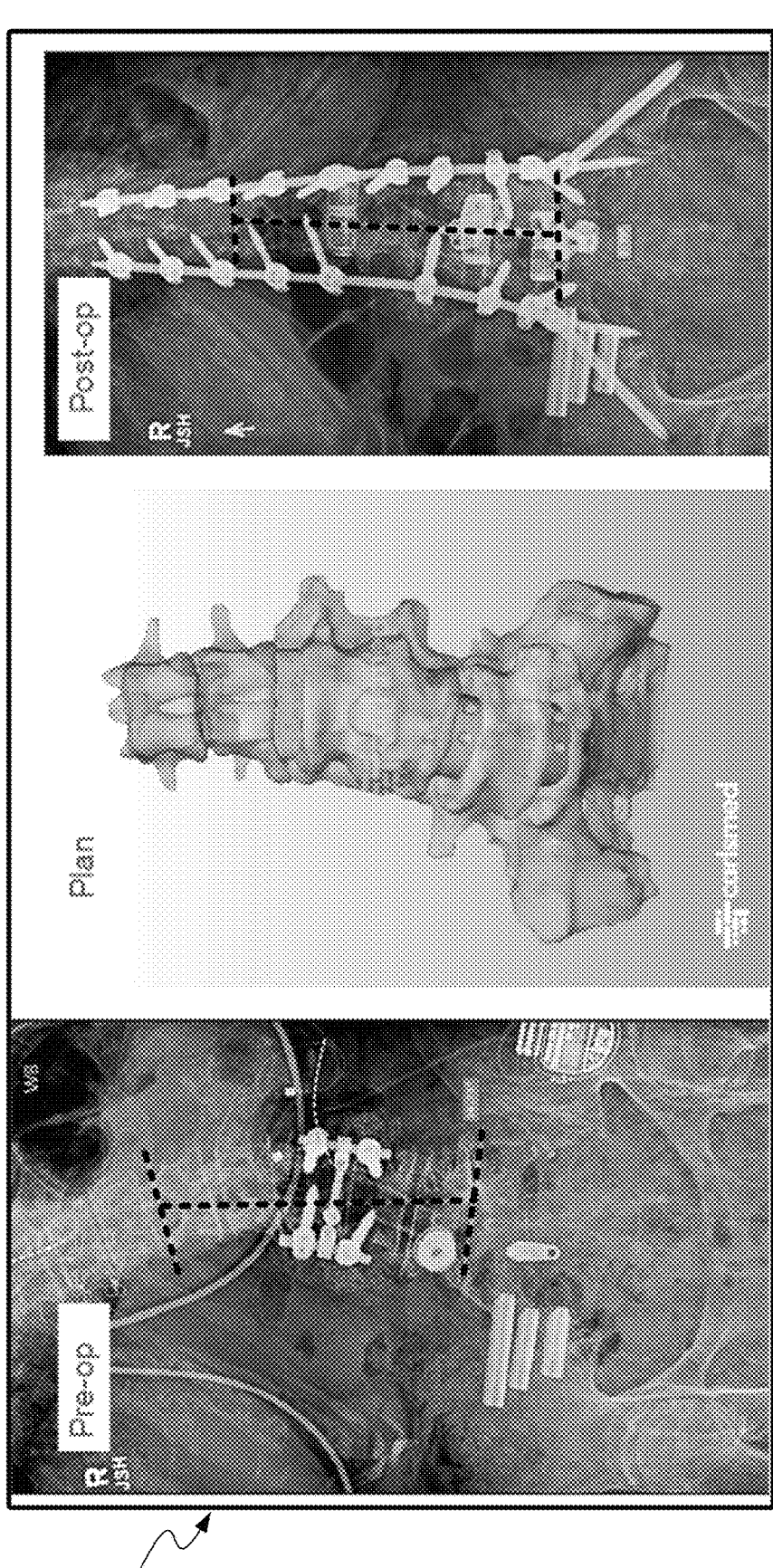
FIG. 10C illustrates pre-operative, plan, intra-operative, and post-operative images to allow for assessment of achievement of surgical goals, according to an embodiment.

FIG. 10C illustrates plan 1040 with a pre-operative imaging, pre-operative plan, intra-operative image, and post-operative image to allow for assessment of achievement of surgical goals, according to an embodiment.

Figure 10D:
FIG. 10D illustrates images that are overlayed to reconcile the pre-operative, plan, intra-operative, and post-operative images to allow for assessment of achievement of surgical goals, according to an embodiment.

FIG. 10D illustrates images 1060 that are overlayed to reconcile the pre-operative plan with the intra-operative images to allow for assessment of achievement of surgical goals, according to an embodiment. Images 1060 illustrate a first stage 1062 (pre-operative plan) and a second stage 1064 (intra-operative image) which show the difference between a pre-operative plan and intra-operative image. This positional information can be used to reposition the implant. The images can include different types of positional information, such as the position of the implant relative to a target planned position, distance between the implant and an anatomical feature, boundary indicating target position for the patient-specific implant, and/or labelling of anatomical elements of the patient proximate to the patient-specific implant.

The images 1060 of FIG. 10D are radiographic images providing lateral view of the patient. The radiographic images can be obtained using an x-ray machine, fluoroscopy imaging machine, or other radiographic imaging device. Other types of images can be acquired and compared. For example, the images 1060 can include a radiographic image from an x-ray machine or C-Arm machine overlaid onto continuous fluoroscopy provided by a fluoroscopic imaging device. In some embodiments, the images 1060 can include pre-operative images, images from a virtual model, and intra-operative images. The number, type, and resolution of the images can be selected based on the comparison. In some embodiments, the system can determine viewing perspectives for the intra-operative image data and can generating one or more reference images of the planned position of the patient-specific implant from the viewing perspective. The system can control imaging devices (or provide instructions to users) to capture intra-operative image data from a target viewing perspective. The perspective matching can facilitate comparisons of image data.

The system (e.g., system 100 of FIG. 1) can overlay the intra-operative data (second stage 1064) on the pre-operative plan (first stage 1062) to illustrate any differences between the intra-operative data and the pre-operative plan. The intra-operative images and pre-operative images can be configured (adjusted) to be virtually overlaid on each other. In some embodiments, the system overlays portions of preoperative images onto the intra-operative images. The intra-operative images can be segmented to isolate anatomical elements. The segmented anatomical elements can be overlayed onto the pre-operative images to show differences between the planned and actual positions of anatomical elements. The system can use machine learning or other algorithms to identify matching features in the intra-operative and pre-operative images. In other embodiments, the anatomical elements of pre-operative plans can be overlayed onto the intra-operative images. The facing and relative positions of the anatomical elements in the pre-operative images can be compared with the actual positions in the intra-operative images. The system can compensate for loading conditions of the pre-operative images. For example, if the patient has pre-operative standing x-rays, the system can modify the relative positions of anatomical elements based on the intra-operative loading of the patient. For example, if the patient is laying horizontally, the method 600 can move the anatomical elements of the pre-operative images to match an unloaded or laying down condition. Accordingly, pre-operative images can be manipulated or modified based on various loading conditions.

The system (e.g., system 100 of FIG. 1) can calculate a difference (e.g., delta) between the intra-operative data (second stage 1064) and the pre-operative plan (first stage 1062). The measurements can include degrees of rotation that the implant in the patient differs from the pre-operative plan, and/or the metric distance that the implant in the patient needs to move to align with the pre-operative plan. A user interface can display the measurements and the overlaid images to a user. For example, the images 1060 of FIG. 10D show, during a surgical procedure, a live comparison between an intra-operative image (second stage 1064) and a pre-operative image (first stage 1062). In some embodiments, a threshold delta can be determined by the system, inputted by a user, or the like. The system can notify the user if the measurement exceeds the threshold delta. In some procedures, the threshold delta can be based on implantation envelopes, boundaries, or other targeting features determined by the system, user, or the like. For example, a user can draw a two-dimensional or three-dimensional boundary on anatomical images for acceptable positions of the implant. The system can then determine whether the implant, or sufficient amount of the implant, is positioned within the boundary.

A user (e.g., healthcare provider, such as a surgeon) can manipulate (e.g., zoom, stretch, crop, and/or rotate) the intra-operative image (second stage 1064) to align with the pre-operative image (first stage 1062), images (e.g., images of virtual models), anatomical renderings, or other images displaying anatomical position information on the device. In some cases, a user can zoom, stretch, and rotate the virtual 3D model (or other pre-operative images) to align with the intra-operative image on the device or other viewing platform. In some embodiments, the system can analyze pre-operative data and then manipulate pre-operative data (e.g., pre-operative images, virtual 3D models, etc.) to align or otherwise synchronize the pre-operative and intra-operative data. For example, the system can generate images of a virtual 3D model of patient anatomy in a corrected configuration such that those images match intra-operative images.

The system can calculate a completion score (e.g., notification 1024 of FIG. 10B) for a surgical procedure and display the score on a display. In the illustrative example of FIG. 10D, a device captures an intra-operative image (second stage 1064) and displays the intra-operative image over the pre-operative image (first stage 1062). The system or user can scale and orient the intra-operative image to closely match the pre-operative plan, reflecting the location of anatomical landmarks and implant. The matching can be performed using one or more segmentation program, best fit algorithms, image manipulation programs, or the like.

Figure 10E:
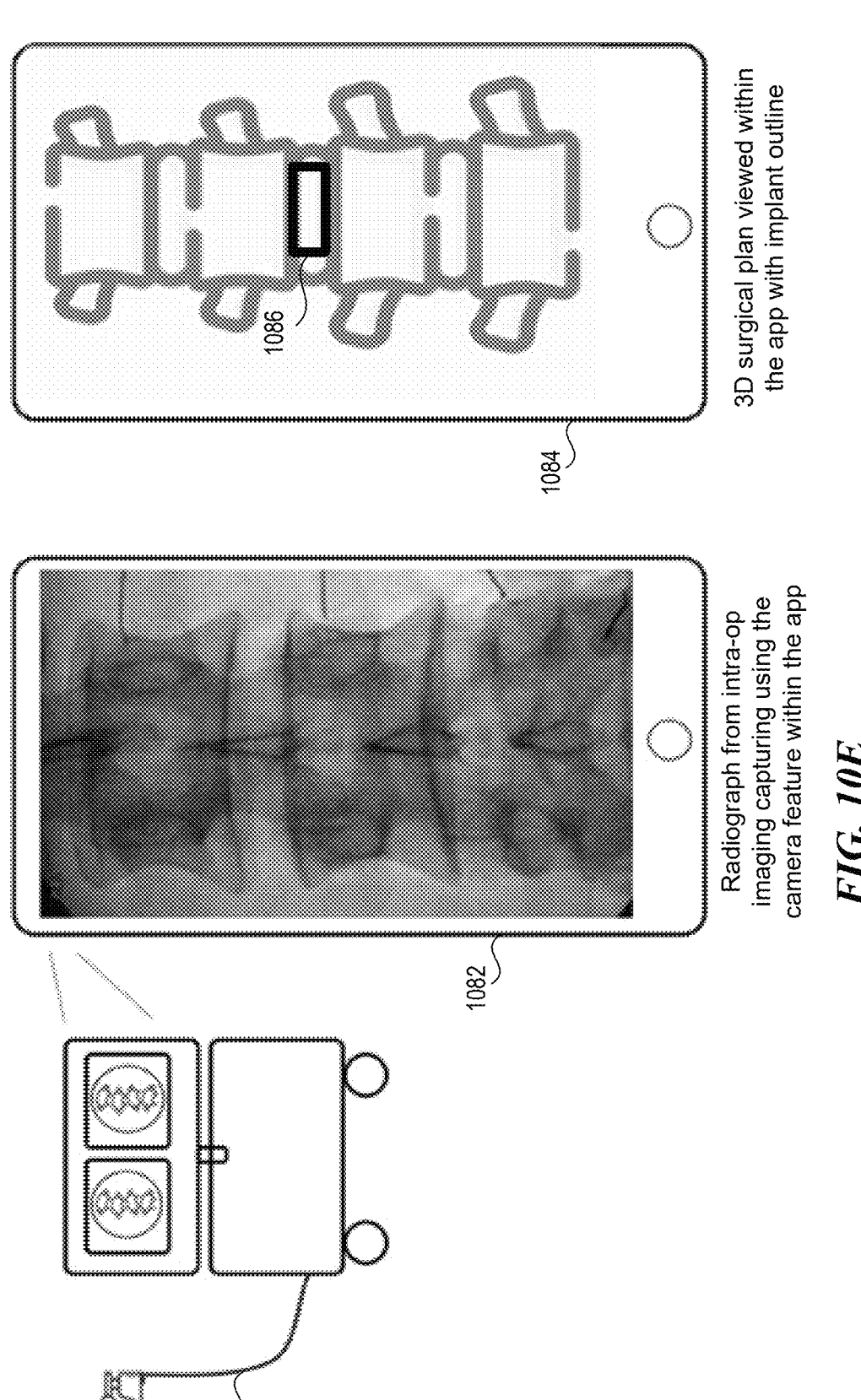
FIG. 10E illustrates intra-operative images and a surgical model displayed on a user interface, according to an embodiment.

FIG. 10E illustrates intra-operative images and a surgical model displayed on a user interface 1082, according to an embodiment. A system, as described in more detail with reference to the system 100 of FIG. 1, can perform one or more checks to repeatedly check positions of anatomical features, positions of instruments, and/or the placement and/or the positioning of one or more implants. The checks can, for example, include dynamic checks, static checks, or the like. The system can obtain image data (e.g., pre-operative images, intraoperative images, etc.), reference models, and anatomical models to perform the checks. The images can be acquired by one or more C-Arms, X-ray machines, cameras (e.g., cameras that capture sequential pictures to use in sequential checks of position), MRI machines, scanners, or the like. The images can include anatomy of the patient, implant(s), equipment positioned in or nearby the patient, or the like. The characteristics (e.g., resolution, number of pixels, etc.) of the image can be selected such that the system can perform one or more image processing techniques. The system can adjust settings on imaging equipment to enhance image data capture, identification accuracy using the image processing techniques, or the like.

The images taken by the one or more visualization systems are referred to as "radiographs", "radiographic images", "intraoperative images", and "radiographic-intra-operative images". Images can be configured (adjusted) to be virtually overlaid on plans (or vice-versa), including a pre-operative plan, an intraoperative plan, or the like. In some embodiments, the system can obtain a series of images showing one or more implants positioned within the patient's body. A physician can then move the implant to a new position. The implant can be imaged again to evaluate the new position. This process can be repeated any number of times to continuously or sequentially image the implant at different locations within the patient until the implant is at a suitable position.

The system can automatically obtain images of the patient based on, for example, one or more surgical plans, pre-defined times, or the like. Additionally or alternatively, a surgical team can control imaging equipment to obtain images at desired times. The system can provide instructions for positioning the imaging equipment (e.g., C-Arms, X-ray machines, fluoroscopy imaging machines, or the like) to obtain suitable images for comparison to, for example, surgical plans, pre-operative simulations showing targeted positions, or the like. The instructions can use imaging equipment to be used, imaging settings, target orientation/ position of imaging equipment, etc.

The system can perform any number of implant position checks to confirm that the implant is in an acceptable location. The position checks can be non-invasive image-guided checks for intraoperatively analyzing the current location of the implant based on obtained images of the patient. The system can identify the implant in the images and then synchronize implant data in the surgical plan with the patient images. For example, the system can synchronize a virtual anatomical model of the surgical plan with radiograph images and then compare the position of the physical implant to a target or acceptable implant position. This process can be repeated until the implant is positioned at an acceptable location in the patient based on the comparison. During a surgical procedure, images can be repeatedly taken to evaluate delivery of the implant.

The system can perform non-invasive image-guided implant position checks by analyzing images to, for example, identify implant information (e.g., the profile of implant within a radiographic image (images taken using a camera, C-Arm, X-ray, etc.)), identify anatomical information (e.g., the types of anatomical elements, tissue type, etc. near the implant), or the like. The system can then compare a reference implant profile with the imaged implant shape to define the implant's current anatomical orientation. The reference implant profile can be retrieved from a set of implant profiles (e.g., a side profile, top profile, oblique profile, etc.) from different viewing perspectives. These implant profiles can be generated from a virtual model of the implant (e.g., CAD model of the implant), or drawn by the user (e.g., drawn via a touch screen). In some embodiments, the system can generate an implant profile based on the viewing perspective and/or implant's current anatomical orientation. In some embodiments, the system can identify one or more image keying features of the implant. Example image keying features can include, for example, opaque markers, edges, or other features of the implant that can be identified using image processing techniques. The system can retrieve image keying feature information from a database containing designs for the implant. For example, a patient-specific implant can have associate virtual models (e.g., three-dimensional virtual model, CAD files, etc.), keying feature files, data for identifying implants, determining implant orientations, unique keying features, or the like. The system can match reference image keying features with corresponding features of the implant in the images to determine the position and orientation of the implant in the patient.

The system can perform one or more synchronization routines using image data and non-image data to command the image system (e.g., camera system, robotic C-Arm imaging system, X-ray system,) and/or provide instructions for obtaining additional images. For example, synchronization routines can include matching landmarks (e.g., keying features) to synchronize or nearly synchronize images (e.g., images taken for performing checks) with one or more virtual models, pre-operative plans, intraoperative plans, or the like. Additionally or alternatively, the system can retrieve manipulate components of the virtual 3D model based on the captured images. For example, the components of a virtual 3D model can be manipulated to be aligned with the radiograph taken by the cameras, X-ray, C-Arm, or the like. The virtual 3D model (or components thereof) can be manipulated (e.g., by zooming, stretching, cropping, and/or rotating the virtual 3D model) to align the 3D virtual model with radiograph. The 3D virtual model can include an anatomical model representing anatomy of a patient, implant model, instrument model, or the like. In some embodiments, the alignment can be performed using one or more best fit routines using, for example, one or more edge detection routines, segmentation routines, filtering routines, image recognition routines, or combinations thereof. The system can confirm placement of implant by confirming the implant in the intra-operative image (e.g., the radiograph) is in the same placement as the placement of the implant in the pre-operative surgical plan. The placement can be scored based on differences between the pre-operative and intra-operative images. The scoring routine can determine the distance between a target position window and the actual position of the implant. If the actual position is within the target position window, the system can indicate that the implant is at the target location. The target position window can be determined using machine learning ML models, inputted by a user, or the like. In some embodiments, the system can confirm the implant is positioned at a target location based certain portions of the implant contacting targeted anatomical features.

In some embodiments, the system can perform real-time checks against a captured images (e.g., sequentially captured images obtained using a C-Arm machine 1088) within an augmented reality (AR) application. For example, the system can use a camera feature within the AR application to view intraoperative radiograph images on a user interface 1082. The camera feature of the AR application does not require a camera on the user interface 1082 to take the intraoperative image, rather it displays the intraoperative radiograph images on the user interface 1082. As shown on the user interface 1082, the radiograph image can be taken prior to implantation of the implant. As described in more detail with reference to FIG. 10F, the subsequent radiograph images can be taken and displayed on the user interface to show the implant and/or an inserter entering, being installed, etc. in the anatomical space.

As shown on the user interface 1084, the implant 1086 is outlined or highlighted in the 3D surgical implant plan being viewed within the AR application on the user interface 1084. The images can be viewed and/or displayed on a user device (e.g., a smartphone, tablet, other computing device, etc.) configured with the AR application to perform the real-time checks against the radiograph images. In some embodiments, the user can open the AR application and hold the user device in a manner to enable viewing of the radiograph images displayed on the user interface 1084. The AR application can use the system to identify the implant and/or viewing perspective of the radiograph image and match the implant profile (e.g., from a preoperative three-dimensional (3D) surgical implant plan, etc.) to the radiograph image. The AR application can then align the 3D surgical implant plan to the radiograph image based on the anatomical landmarks (e.g., anatomical elements, tissue types, etc.) or implant profile (e.g., implant projection, etc.) identified in the radiograph image. As described herein, the user can reorient the 3D surgical implant plan to match the radiograph image taken (e.g., by zooming, stretching, cropping, and/or rotating the implant plan).

Figure 10F:
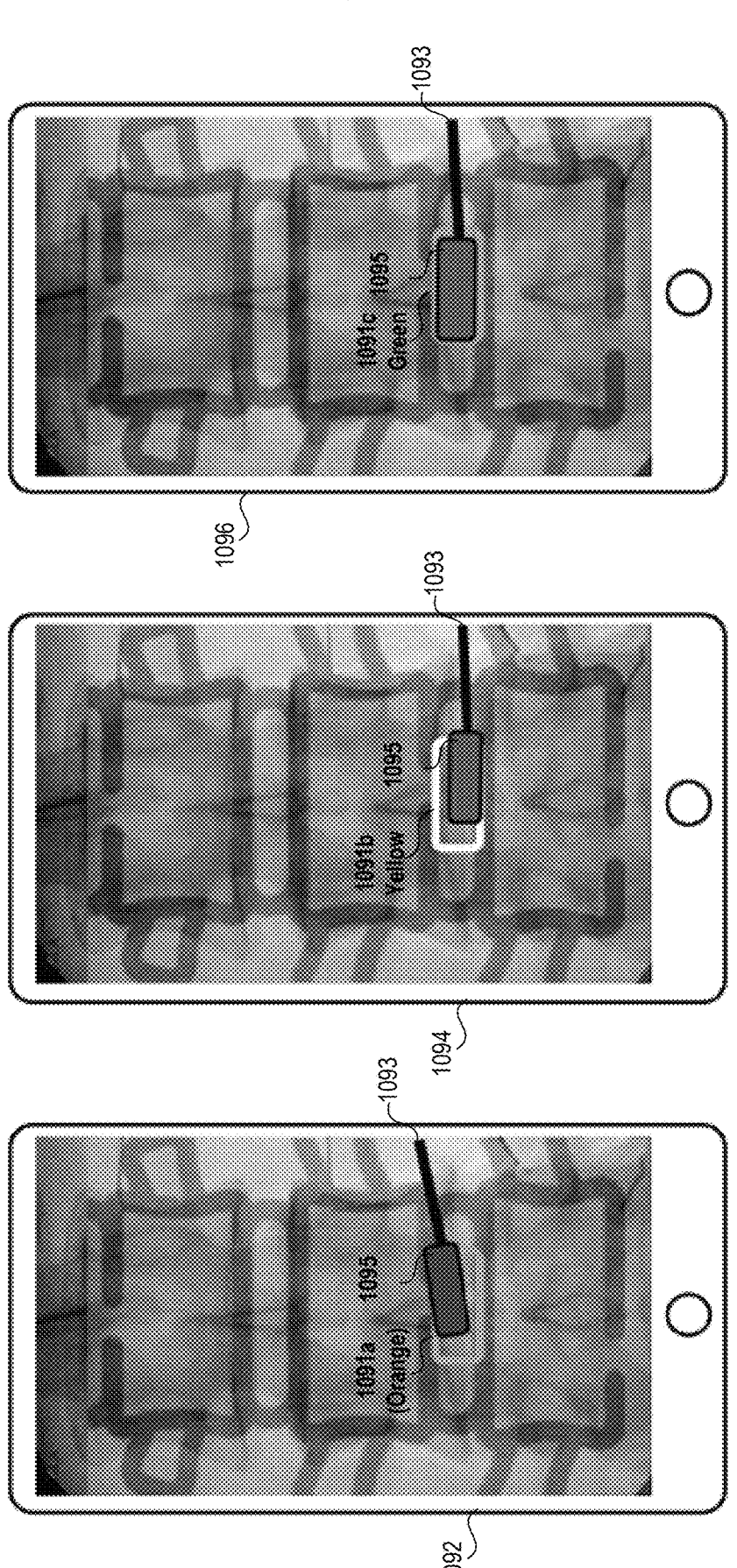
FIG. 10F illustrates images of an implant and an inserter device displayed on a user interface, according to an embodiment.

FIG. 10F illustrates images of an implant and an inserter device displayed on a user interface, according to an embodiment. As the surgical procedure progresses and subsequent radiograph images are taken with the C-Arm machine (as described in FIG. 10E), the AR application can track the progress of the implant's position against the adjacent anatomy and/or the 3D surgical implant plan. For example, as shown on user interface 1092, the 3D surgical plan (as display in user interface 1084 of FIG. 10E) is placed on top of or "snapped" onto the radiograph image in a semi-transparent overlay. As further displayed on the user interface 1092, the inserter instrument 1093 and implant 1095 (e.g., attached to the inserter instrument or held by the inserter instrument) are radiopaque and can be seen on the user interface 1092 as they progress towards the target implant position 1091*a* (illustrated in orange or user selected color). With each subsequent radiograph image taken, the implant can be moved to match the 3D surgical implant plan anatomy. As shown on user interface 1094, the inserter 1093 and implant 1095 have progressed generally closer to the implant 1091*a* on the 3D surgical implant plan. The implant 1091*a* on the 3D surgical implant plan can change in color depending on the proximity to the implant's optimal or target placement. The optimal placement can be determined using a machine learning ML engine or inputted by a user.

As shown on the user interface 1094, the implant 1091*b* on the 3D surgical implant is illustrated in another color (e.g., yellow or another user selected color), indicating the implant 1095 and inserter instrument 1093 are generally closer to optimal placement. Optimal placement can be chosen by a computer system and/or a user (e.g., a physician, surgeon, surgical team, etc.) when making the preoperative surgical plan. As subsequent radiograph images are taken, the implant as displayed and tracked by the radiograph is be moved closer to the optimal position. The images can be annotated to provide, for example, assistance, such as instructions for positioning, physician notes, vitals, implant information. The user interface 1096 shows the implant 1095 and inserter instrument 1093 at the optimal position (or acceptable location) so the target implant position 1091*c* in the 3D surgical implant plan is updated to be, for example, green. Other types of imaging can be used for real-time or near real-time imaging.

Acceptable locations can be determined using a machine learning ML engine or inputted by a user and can be locations within a maximum acceptable distance from an optimal location. In some embodiments, when the implant has reached an acceptable position (or optical location), the 3D surgical plan will be updated with one or more confirmatory messages (e.g., a sound, color change, other audible or visual ques, etc.) and/or a final image will be taken and saved to the patient data. Additional measurements can be taken to confirm the implant's placement. In some embodiments, the measurements can be displayed on the user interface 1092 in addition to the 3D surgical plan snapped onto the radiograph image. These additional measurements can be, for example, a distance between anatomical features, distances between the implant and anatomical features, distances between the intended placement and actual placement of the implant, distances between devices (e.g., instruments, instruments and implants, etc.), angular positions of devices, or the like.

The system can analyze surgical plans to determine whether the implant should be repositioned and can generate instructions for moving the implant toward an optimal position. The instructions can be intraoperatively outputted to assist with repositioning of the implant. For example, the instructions can be displayed via the user interface 1094 and can include including text, annotations (e.g., arrows, boxes, etc.), measurements, drawing/images, and/or surgical steps can be overlaid onto a displayed image (e.g., radiograph image). In some embodiments, an optimal or acceptable position of the implant can be inserted into or overlaid onto the image to show a physician the difference between the optimal position and the current position of the implant. In some embodiments, the optimal position can be illustrated using an outline of the implant, labels, or annotations. In some embodiments, the system can identify an acceptable location window based on the optimal position. This allows a physician to place the implant while allowing for minor adjustments to improve outcomes. The system can also perform any number of intraoperative simulations based on the intraoperative images to update surgical plans, modify acceptable location windows or optimal positions, and provide additional feedback for assistance with a surgical procedure.

Figure 11:
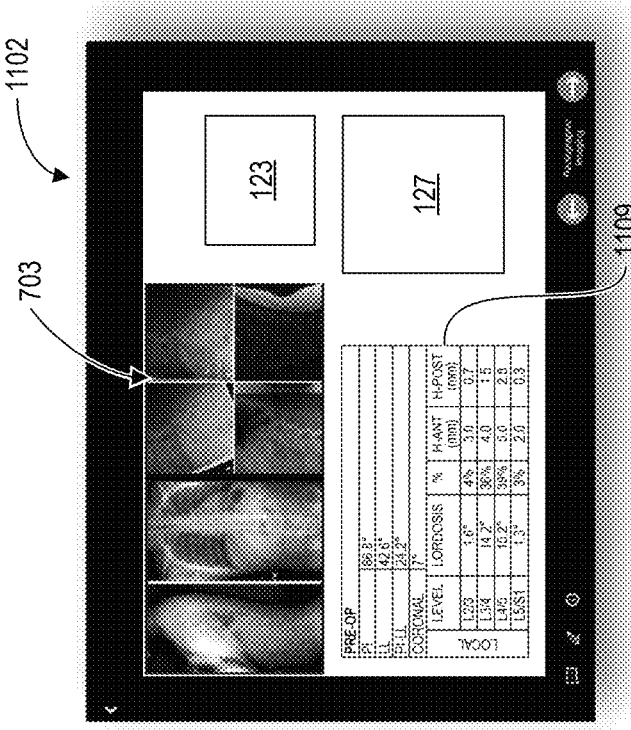
FIG. 11 illustrates an exemplary surgical plan report detailing the surgical plan for surgeon review and that may be used and/or generated in connection with the methods described herein, according to an embodiment.
Figure 11:
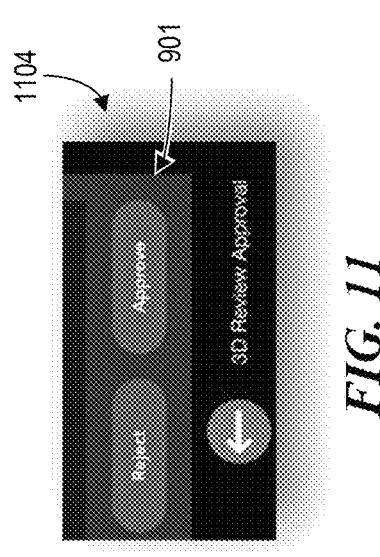
Figure 11:
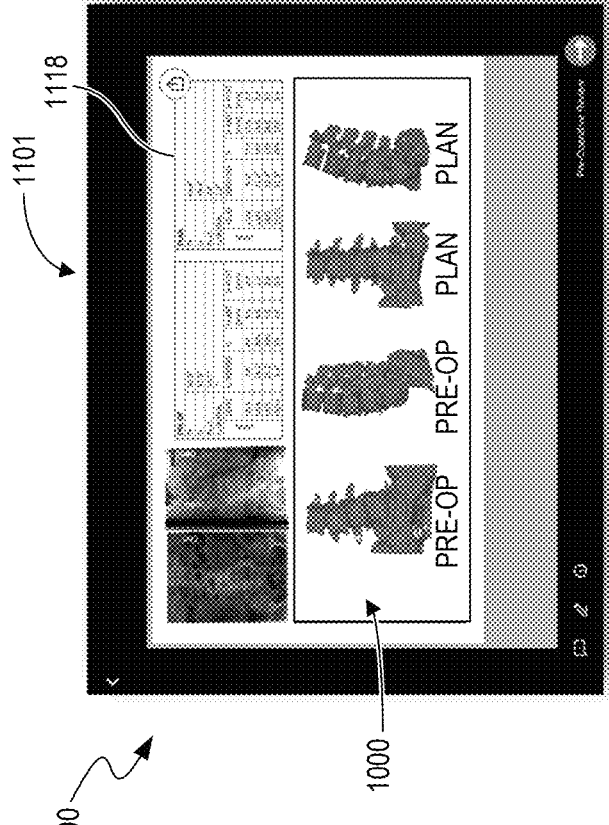
Figure 11:
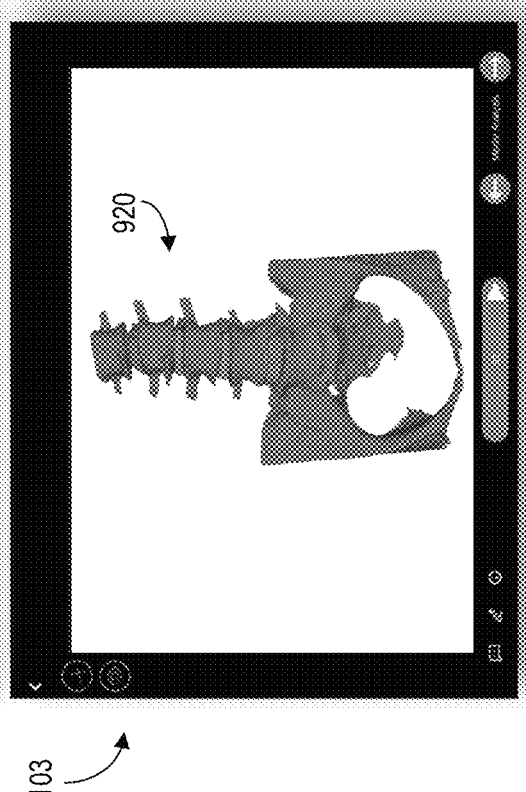

FIG. 11 provides a series of images illustrating an example of a patient surgical plan report 1100 that includes the surgical plan 1000 and that may be transmitted to a surgeon for review and approval (e.g., as transmitted in step 508 of the method 500). The surgical plan report 1100 can include a multi-page report detailing aspects of the surgical plan 1000. For example, the multi-page report may include a first page 1101 demonstrating an overview of the surgical plan 1000 (e.g., as shown in FIG. 10), a second page 1102 illustrating patient images (e.g., such as the patient images 703 received in step 502 and shown in FIG. 7D), a third page 1103 illustrating an enlarged view of the virtual model of the corrected anatomical configuration (e.g., the virtual model 920 shown in FIG. 9), and a fourth page 1104 prompting the surgeon to either approve or reject the surgical plan via a user input element 901 (e.g., one or more buttons, a drop down menu, etc.). The surgical plan report 1100 can include one or more pre-operative metrics for pre-determined indications.

Page two 1102 can include pre-operative metrics 1109 determined based on the patient images 1113. The pre-operative metrics 1109 can be used to perform a reimbursement analysis, including whether a procedure, kit, instrument, implants, or other treatment-related item or step will qualify for payment or reimbursement. In some embodiments, planned metrics 1118 (page 1101) can be used to validate a predicted outcome for the pre-determined indications will qualify for payment or reimbursement.

Page two 1102 can also include reimbursement data 123 and regulatory data 127. The reimbursement data 123 can include the data discussed in connection with FIG. 10B. The output (e.g., recommended codes) can be labeled in the illustrated images 703. The pre-operative metrics 1109 correlated to the coding can be bolded or otherwise identified. This allows a user to simultaneously view reimbursement information and physiology associated with those reimbursements. The regulatory data 127 can include images of virtual models with anatomical features and regulatory compliant implants. The planned anatomical model (e.g., virtual anatomical model 920 of FIG. 10A) can have implants with regulatory approved configurations. The physician can therefore have confidence that the implants and planned outcome is based on regulatory approved technology.

In some embodiments, the system can measure the anatomical features and generate virtual models. The system can then generate the regulatory compliant implants that fit the model. If the physician modifies the model or implants resulting in a non-regulatory compliant treatment or implant, the system can generate an alert indicating that regulatory compliance has not been maintained. Advantageously, page 1102 allows a user to simultaneously view patient images, anatomical planned models, planned pathologies based on regulatory compliance, reimbursement data, and regulatory data. Moreover, correlations between various elements of different data sets can be identified to enable a viewer to understand the interrelationships.

Of course, additional information about the surgical plan can be presented with the report 1100 in the same or different formats. In some embodiments, if the surgeon rejects the surgical plan 1000, the surgeon can be prompted to provide feedback regarding the aspects of the surgical plan 1000 the surgeon would like adjusted.

The patient surgical plan report 1100 can be presented to the surgeon on a digital display of a computing device (e.g., the client computing device 102 shown in FIG. 1). In some embodiments, the report 1100 is interactive and the surgeon can manipulate various aspects of the report 1100 (e.g., adjust views of the virtual model, zoom-in, zoom-out, annotate, etc.). However, even if the report 1100 is interactive, the surgeon generally cannot directly change the surgical plan 1000. Rather, the surgeon may provide feedback and suggested changes to the surgical plan 1000, which can be sent back to the computing system that generated the surgical plan 1000 for analysis and refinement.

Figure 12A:
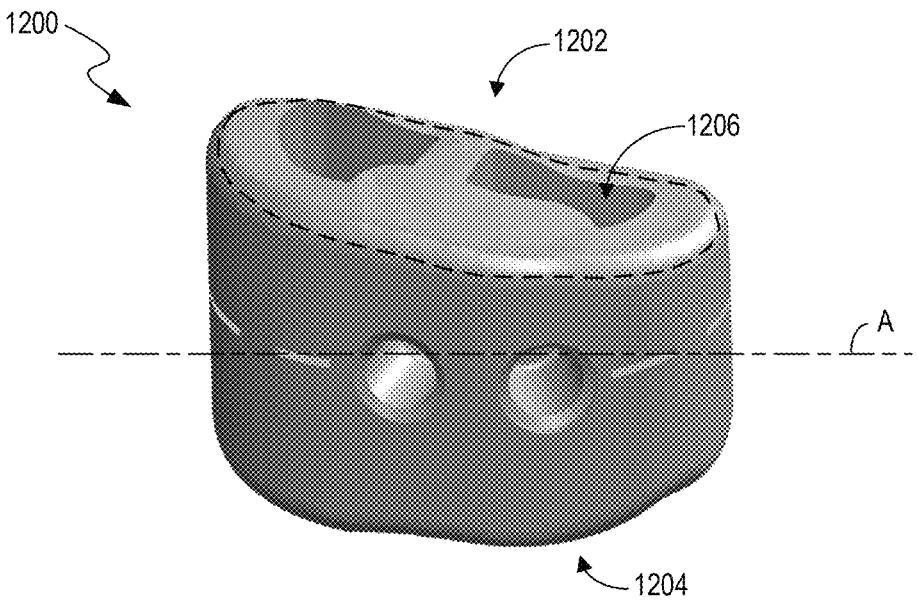
FIGS. 12A and 12B illustrate an exemplary patient-specific implant that can be used and/or generated in connection with the methods described herein, according to an embodiment.
Figure 12B:
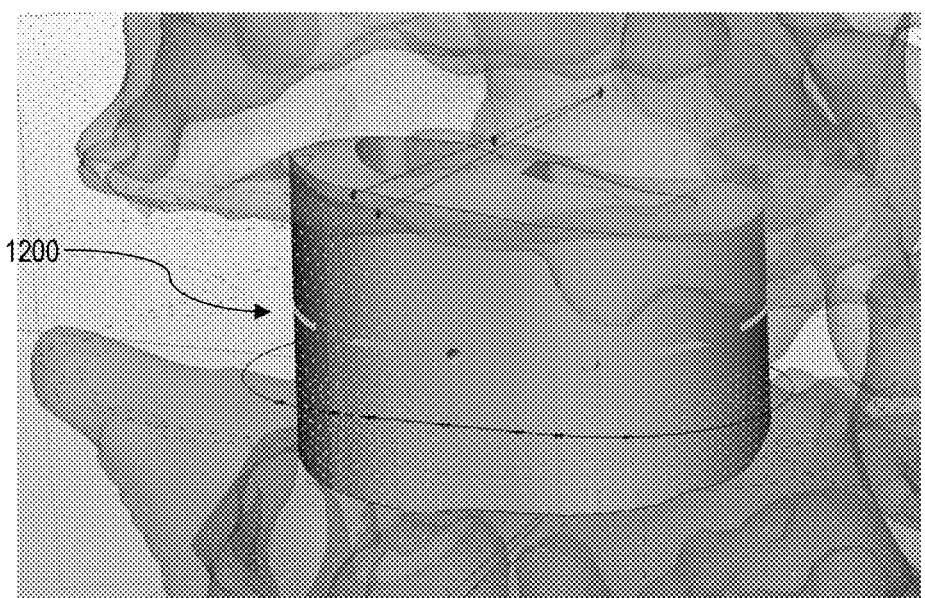

FIG. 12A illustrates an example of a patient-specific implant 1200 (e.g., as designed in step 516 and manufactured in step 518 of the method 500), and FIG. 12B illustrates the implant 1200 implanted in the patient. The implant 1200 can be any orthopedic or other implant specifically designed to induce the patient's body to conform to the previously identified corrected anatomical configuration. The implant 1202 can be based on a design generated by mapping a negative space between segmented anatomic elements of a corrected pathology. The negative space is then filled with a virtual implant. In imbursement-constrained embodiments, the configuration of the negative space can be selected based on one or more parameters for the medical reimbursable virtual implant. For example, the implant 1200 can be a cervical fusion implant, a lumbar fusion implant, an artificial disc, an expandable intervertebral cage, or other implant disclosed herein.

For example, system 100 of FIG. 1 can obtaining insurance information for the patient from the database 151. The system 100 can then retrieve one or more design parameters from a database 151 based on the obtained insurance information. The treatment model 181 can then design the patient-specific implant 1202 using the retrieved design parameter(s). The design parameters can be a configuration (e.g., an implant footprint shown in dashed line in FIG. 12A) for devices approved for use by regulatory agency or governmental body, payment requirement, imbursement requirement, etc. Prior to manufacturing the implant 1202, the system can notify the user of the at least one medical reimbursement code for user review and approval.

In the illustrated embodiment, the implant 1200 is a vertebral interbody device having a first (e.g., upper) surface 1202 configured to engage an inferior endplate surface of a superior vertebral body and a second (e.g., lower) surface 1204 configured to engage a superior endplate surface of an inferior vertebral body. The first surface 1202 can have a patient-specific topography designed to match (e.g., mate with) the topography of the inferior endplate surface of the superior vertebral body to form a generally gapless interface therebetween. Likewise, the second surface 1204 can have a patient-specific topography designed to match or mate with the topography of the superior endplate surface of the inferior vertebral body to form a generally gapless interface therebetween. The implant 1200 may also include a recess 1206 or other feature configured to promote bony ingrowth. Because the implant 1200 is patient-specific and designed to induce a geometric change in the patient, the implant 1200 is not necessarily symmetric, and is often asymmetric. For example, in the illustrated embodiment, the implant 1200 has a non-uniform thickness such that a plane defined by the first surface 1202 is not parallel to a central longitudinal axis A of the implant 1200. Of course, because the implants described herein, including the implant 1200, are patient-specific, the present technology is not limited to any particular implant design or characteristic. Additional features of patient-specific implants that can be designed and manufactured in accordance with the present technology are described in U.S. patent application Ser. Nos. 16/987,113 and 17/100,396, the disclosures of which are incorporated by reference herein in their entireties.

Figure 13:
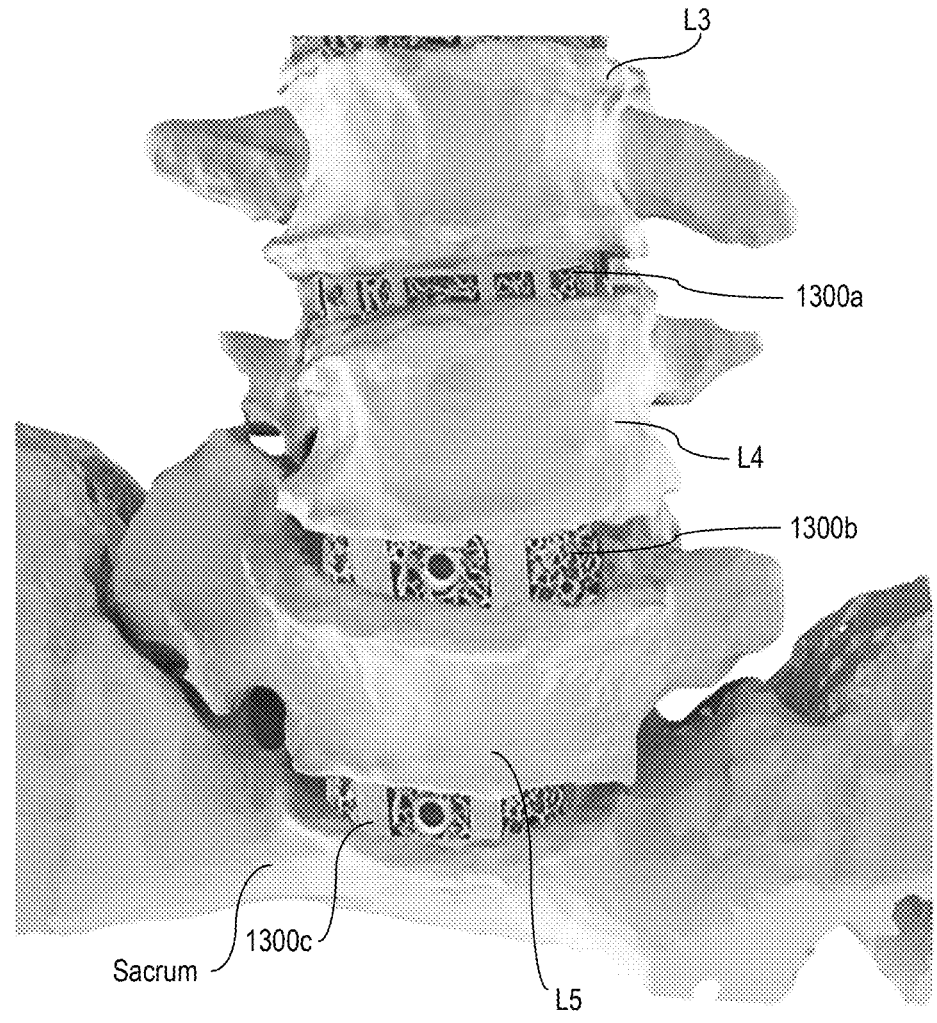
FIG. 13 illustrates a segment of a patient's spine after several patient-specific implants have been implanted therein.

The patient-specific medical procedures described herein can involve implanting more than one patient-specific implant into the patient to achieve the corrected anatomical configuration (e.g., a multi-site procedure). FIG. 13, for example, illustrates a lower spinal cord region having three patient specific implants 1300a-1300c implanted at different vertebral levels. More specifically, a first implant 1300a is implanted between the L3 and L4 vertebral bodies, a second implant 1300b is implanted between the L4 and L5 vertebral bodies, and a third implant 1300c is implanted between the L5 vertebral body and the sacrum. Together, the implants 1300a-c can cause the patient's spinal cord region to assume the previously identified corrected anatomical configuration (e.g., transforming the patient's anatomy from its pre-operative diseased configuration to the post-operative optimized configuration). In some embodiments, more or fewer implants are used to achieve the corrected anatomical configuration. For example, in some embodiments one, two, four, five, six, seven, eight, or more implants are used to achieve the corrected anatomical configuration. In embodiments involving more than one implant, the implants do not necessarily have the same shape, size, or function. In fact, the multiple implants will often have different geometries and topographies to correspond to the target vertebral level at which they will be implanted. As also shown in FIG. 13, the patient-specific medical procedures described herein can involve treating the patient at multiple target regions (e.g., multiple vertebral levels).

In addition to designing patient-specific medical care based off reference patient data sets, the systems and methods of the present technology may also design patient-specific medical care based off disease progression for a particular patient. In some embodiments, the present technology therefore includes software modules (e.g., machine learning models or other algorithms) that can be used to analyze, predict, and/or model disease progression for a particular patient. The machine learning models can be trained based off a plurality of reference patient data sets that includes, in addition to the patient data described with respect to FIG. 1, disease progression metrics for each of the reference patients. The progression metrics can include measurements for disease metrics over a period of time. Suitable metrics may include spinopelvic parameters (e.g., lumbar lordosis, pelvic tilt, sagittal vertical axis (SVA), cobb angel, coronal offset, etc.), disability scores, functional ability scores, flexibility scores, VAS pain scores, or the like. The progression of the metrics for each reference patient can be correlated to other patient information for the specific reference patient (e.g., age, sex, height, weight, activity level, diet, etc.).

In some embodiments, the present technology includes a disease progression module that includes an algorithm, machine learning model, or other software analytical tool for predicting disease progression in a particular patient. The disease progression module can be trained based on reference patient data sets that includes patient information (e.g., age, sex, height, weight, activity level, diet) and disease metrics (e.g., diagnosis, spinopelvic parameters such as lumbar lordosis, pelvic tilt, sagittal vertical axis, cobb angel, coronal offset, etc., disability scores, functional ability scores, flexibility scores, VAS pain scores, etc.). The disease metrics can include values over a period of time. For example, the reference patient data may include values of disease metrics on a daily, weekly, monthly, bi-monthly, yearly, or other basis. By measuring the metrics over a period of time, changes in the values of the metrics can be tracked as an estimate of disease progression and correlated to other patient data.

In some embodiments, the disease progression module can therefore estimate the rate of disease progression for a particular patient. The progression may be estimated by providing estimated changes in one or more disease metrics over a period of time (e.g., X % increase in a disease metric per year). The rate can be constant (e.g., 5% increase in pelvic tilt per year) or variable (e.g., 5% increase in pelvic tilt for a first year, 10% increase in pelvic tilt for a second year, etc.). In some embodiments, the estimated rate of progression can be transmitted to a surgeon or other health-care provider, who can review and update the estimate, if necessary.

As a non-limiting example, a particular patient who is a fifty-five-year-old male may have a SVA value of 6 mm. The disease progression module can analyze patient reference data sets to identify disease progression for individual reference patients have one or more similarities with the particular patient (e.g., individual patients of the reference patients who have an SVA value of about 6 mm and are approximately the same age, weight, height, and/or sex of the patient). Based on this analysis, the disease progression module can predict the rate of disease progression if no surgical intervention occurs (e.g., the patient's VAS pain scores may increase 5%, 10%, or 15% annually if no surgical intervention occurs, the SVA value may continue to increase by 5% annually if no surgical intervention occurs, etc.).

The systems and methods described herein can also generate models/simulations based on the estimated rates of disease progression, thereby modeling different outcomes over a desired period of times. Additionally, the models/ simulations can account for any number of additional dis-eases or condition to predict the patient's overall health, mobility, or the like. These additional diseases or conditions can, in combination with other patient health factors (e.g., height, weight, age, activity level, etc.) be used to generate a patient health score reflecting the overall health of the patient. The patient health score can be displayed for sur-geon review and/or incorporated into the estimation of disease progression. Accordingly, the present technology can generate one or more virtual simulations of the predicted disease progression to demonstrate how the patient's anatomy is predicted to change over time. Physician input can be used to generate or modify the virtual simulation(s). The present technology can generate one or more post-treatment virtual simulations based on the received physi-cian input for review by the healthcare provider, patient, etc.

In some embodiments, the present technology can also predict, model, and/or simulate disease progression based on one or more potential surgical interventions. For example, the disease progression module may simulate what a patient's anatomy may look like 1, 2, 5, or 10 years post-surgery for several surgical intervention options. The simulations may also incorporate non-surgical factors, such as patient age, height, weight, sex, activity level, other health conditions, or the like, as previously described. Based on these simulations, the system and/or a surgeon can select which surgical intervention is best suited for long-term efficacy. These simulations can also be used to determine patient-specific corrections that compensate for the pro-jected diseases progression.

Accordingly, in some embodiments, multiple disease pro-gression models (e.g., two, three, four, five, six, or more) are simulated to provide disease progression data for several different surgical intervention options or other scenarios. For example, the disease progression module can generate mod-els that predict post-surgical disease progression for each of three different surgical interventions. A surgeon or other healthcare provider can review the disease progression mod-els and, based on the review, select which of the three surgical intervention options is likely to provide the patient with the best long-term outcome. Of course, selecting the optimal intervention can also be fully or semi-automated, as described herein.

Based off of the modeled disease progression, the systems and methods described herein can also (i) identify the optimal time for surgical intervention, and/or (ii) identify the optimal type of surgical procedure for the patient. In some embodiments, the present technology therefore includes an intervention timing module that includes an algorithm, machine learning model, or other software analytical tool for determining the optimal time for surgical intervention in a particular patient. This can be done, for example, by ana-lyzing patient reference data that includes (i) pre-operative disease progression metrics for individual reference patients, (ii) disease metrics at the time of surgical intervention for individual reference patients, (iii) post-operative disease progression metrics for individual reference patients, and/or (iv) scored surgical outcomes for individual reference patients. The intervention timing module can compare the disease metrics for a particular patient to the reference patient data sets to determine, for similar patients, the point of disease progression at which surgical intervention pro-duced the most favorable outcomes.

As a non-limiting example, the reference patient data sets may include data associated with reference patients' sagittal vertical axis. The data can include (i) sagittal vertical axis values for individual patients over a period of time before surgical intervention (e.g., how fast and to what degree the sagittal vertical axis value changed), (ii) sagittal vertical axis of the individual patients at the time of surgical intervention, (iii) the change in sagittal vertical axis after surgical inter-vention, and (iv) the degree to which the surgical interven-tion was successful (e.g., based on pain, quality of life, or other factors). Based on the foregoing data, the intervention timing module can, based on a particular patient's sagittal vertical axis value, identify at which point surgical inter-vention will have the highest likelihood of producing the most favorable outcome. Of course, the foregoing metric is provided by way of example only, and the intervention timing module can incorporate other metrics (e.g., lumbar lordosis, pelvic tilt, sagittal vertical axis, cobb angel, coronal offset, disability scores, functional ability scores, flexibility scores, VAS pain scores) instead of or in combination with sagittal vertical axis to predict the time at which surgical intervention has the highest probability of providing a favorable outcome for the particular patient.

The intervention timing module may also incorporate one or more mathematical rules based on value thresholds for various disease metrics. For example, the intervention tim-ing module may indicate surgical intervention is necessary if one or more disease metrics exceed a predetermined threshold or meet some other criteria. Representative thresholds that indicate surgical intervention may be necessary include SVA values greater than 7 mm, a mismatch between lumbar lordosis and pelvic incidence greater than 10 degrees, a cobb angle of greater than 10 degrees, and/or a combination of cobb angle and LL/PI mismatch greater than 20 degrees. Of course, other threshold values and metrics can be used; the foregoing are provided as examples only and in no way limit the present disclosure. In some embodiments, the foregoing rules can be tailored to specific patient populations (e.g., for males over 50 years of age, an SVA value greater than 7 mm indicates the need for surgical intervention). If a particular patient does not exceed the thresholds indicating surgical intervention is recommended, the intervention timing module may provide an estimate for when the patient's metrics will exceed one or more thresholds, thereby providing the patient with an estimate of when surgical intervention may become recommended.

The present technology may also include a treatment planning module that can identify the optimal type of surgical procedure for the patient based on the disease progression of the patient. The treatment planning module can be an algorithm, machine learning model, or other software analytical tool trained or otherwise based on a plurality of reference patient data sets, as previously described. The treatment planning module may also incorporate one or more mathematical rules for identifying surgical procedures. As a non-limiting example, if a LL/PI mismatch is between 10 and 20 degrees, the treatment planning module may recommend an anterior fusion surgery, but if the LL/PI mismatch is greater than 20 degrees, the treatment planning module may recommend both anterior and posterior fusion surgery. As another non-limiting example, if a SVA value is between 7 mm and 15 mm, the treatment planning module may recommend posterior fusion surgery, but if the SVA is above 15 mm, the treatment planning module may recommend both posterior fusion surgery and anterior fusion surgery. Of course, other rules can be used; the foregoing are provided as examples only and in no way limit the present disclosure.

Without being bound by theory, incorporating disease progression modeling into the patient-specific medical procedures described herein may even further increase the effectiveness of the procedures. For example, in many cases it may be disadvantageous to operate after a patient's disease progresses to an irreversible or unstable state. However, it may also be disadvantageous to operate too early, before the patient's disease is causing symptoms and/or if the patient's disease may not progress further. The disease progression module and/or the intervention timing module can therefore help identify the window of time during which surgical intervention in a particular patient has the highest probability of providing a favorable outcome for the patient.

As one skilled in the art will appreciate, any of the software modules described previously may be combined into a single software module for performing the operations described herein. Likewise, the software modules can be distributed across any combination of the computing systems and devices described herein, and are not limited to the express arrangements described herein. Accordingly, any of the operations described herein can be performed by any of the computing devices or systems described herein, unless expressly noted otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

EXAMPLES

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples can be combined in any suitable manner, and placed into a respective independent example. The other examples can be presented in a similar manner.

1. A method comprising:
   (a) obtaining at least one image of an implant located in a patient;
   (b) identifying the implant in the at least one image;
   (c) synchronizing a virtual anatomical model and the at least one image;
   (d) comparing a position of the implant in the patient to a position of a virtual implant of the virtual anatomical model based on the synchronized virtual anatomical model and the at least one image; and
   repeating all or some of the steps (a)-(d) to determine that the implant is positioned at an acceptable location in the patient based on the comparison.
2. The method of example 1,
   wherein synchronizing the virtual anatomical model and the at least one image includes manipulating the virtual anatomical model and/or the at least one image of a pre-operative plan according to a best fit routine, and wherein the all or some of the steps (a)-(d) are repeated sequentially using images of the patient showing the implant at another location.

3. The method of any of examples 1-2, wherein manipulating the virtual anatomical model and/or the at least one image includes at least one of zooming, stretching, or rotating the virtual anatomical model to align anatomical features in the virtual anatomical model with corresponding anatomical features in the at least one image.

4. The method of any of examples 1-3, wherein manipulating the virtual anatomical model and/or the at least one image includes at least one of zooming, stretching, or rotating the at least one image to align the at least one image with the virtual anatomical model.

5. The method of any of examples 1-4, further comprising determining the acceptable location in the patient using a ML engine, wherein the acceptable location is inputted by a user.

6. The method of any of examples 1-5, further comprising sequentially receiving images of the patient to repeatedly perform steps (a)-(d) using a respective one of the received images.

7. The method of any of examples 1-6, further comprising:

retrieving a patient-specific surgical plan for the patient;
generating instructions for moving the implant toward a target location in the patient-specific surgical plan; and
causing the instructions to be intra-operatively outputted to assist with repositioning the implant.

8. The method of any of examples 1-7,
wherein the at least one image is a fluoroscopic image,
wherein the synchronization includes performing an anatomical alignment between the virtual anatomical model and the fluoroscopic image, and
wherein the acceptable location is a maximum acceptable distance from a target location for the implant.

9. The method of any of examples 1-8, further comprising:

obtaining type of implant information for the implant;
obtaining intra-operative image data from one or more imaging devices during a surgical procedure;
selecting an implant-type deviation analysis based on the type of implant information;
generating deviation annotation for positioning the implant that has been inserted into the patient based on the implant-type deviation analysis; and
displaying the deviation annotation via an electronic display.

10. The method of any of examples 1-9, wherein the implant-type deviation analysis includes at least one of:

an interbody cage analysis for deviation annotation of vertebral endplate-based positioning for fusion,
an artificial disk analysis for deviation annotation of vertebral endplate-based positioning for joint articulation, or
a screw and rod fusion system analysis for vertebral body-based positioning for fusion.

11. A computer-implemented method for monitoring patient-specific implant positioning, the method comprising:

displaying, via a user-interface, a patient-specific interactive surgical plan generated by a surgical planning platform based on one or more images of a patient,
wherein the patient-specific interactive surgical plan includes a pre-operatively planned position of a patient-specific implant in the patient for achieving a corrected anatomical configuration;

obtaining intra-operative image data from one or more imaging devices during a surgical procedure;
identifying an intra-operative position of the patient-specific implant in the patient in the intra-operative image data;
determining whether the intra-operative position matches the planned position; and in response to determining the intra-operative position does not match the planned position,
displaying, via the user-interface, the intra-operative position and the planned position to identify a difference between the intra-operative position and the planned position.

12. The computer-implemented method of example 11, further comprising:

comparing the intra-operative image data to planned anatomical configuration data;
determining positional information for the patient-specific implant based on the comparison; and
displaying, via the user-interface, the positional information for the patient-specific implant for evaluating a position of the patient-specific implant.

13. The computer-implemented method of any of examples 11-12, wherein the positional information includes at least one of the position of the patient-specific implant relative to a target planned position,
distance between the patient-specific implant and an anatomical feature,
boundary indicating target position for the patient-specific implant, or
labelling of anatomical elements of the patient proximate to the patient-specific implant.

14. The computer-implemented method of any of examples 11-13, further comprising:

determining a viewing perspective of the intra-operative image data;
generating one or more reference images of the planned position of the patient-specific implant from the viewing perspective; and
comparing the one or more reference images to the intra-operative image data to identify one or more differences between the intra-operative position and the planned position of the patient-specific implant.

15. The computer-implemented method of any of examples 11-14, further comprising:

generating one or more images of the planned position of the patient-specific implant matching intra-operative images of the intra-operative image data; and
overlaying at least one of the images of the planned position onto the intra-operative images to indicate the difference between the intra-operative position and the planned position.

16. The computer-implemented method of any of examples 11-15, wherein the one or more images of the planned position of the patient-specific implant includes one or more images of a virtual three-dimensional model representing anatomy of the patient, images of the patient generated by an imaging device, and/or scans of the patient.

17. The computer-implemented method of any of examples 11-16, wherein the surgical planning platform is configured to determining one or more measurements of the difference between the intra-operative position and the planned position; and

displaying, via the user-interface, the one or more measurements of the difference between the intra-operative position and the planned position.

18. The computer-implemented method of any of examples 11-17, further comprising:

displaying a comparison of the patient-specific interactive surgical plan and the intra-operative image data, wherein the comparison includes:

overlaying the intra-operative image data on the patient-specific interactive surgical plan; and marking one or more differences between the intra-operative position of the patient-specific implant and the planned position.

19. The computer-implemented method of any of examples 11-18, further comprising:

determining, based on the intra-operative position, a progress metric of the surgical procedure to install the patient-specific implant in the patient; and displaying, via the user-interface, the progress metric of the surgical procedure.

20. The computer-implemented method of any of examples 11-19, further comprising:

selecting reference patient data sets each including one or more pre-operative patient images and one or more intra-operative images;

training a machine-learning model using the selected reference patient data sets; and inputting the intra-operative image data of the patient into the trained machine-learning model to determine whether the intra-operative position matches the planned position.

21. The computer-implemented method of any of examples 11-20, further comprising:

overlaying the intra-operative image data on the patient-specific interactive surgical plan; and orienting and scaling the intra-operative image data based on a location of one or more anatomical landmarks of the patient.

22. The computer-implemented method of any of examples 11-21, further comprising:

obtaining one or more pre-operative metrics for pre-determined indications; and obtaining one or more post-operative metrics to validate a target outcome for the pre-determined indications.

23. A computer-implemented method for monitoring implant positioning, the method comprising:

obtaining intra-operative image data from one or more imaging devices during a surgical procedure;

identifying an intra-operative position of an implant in a patient in the intra-operative image data;

generating a comparison image of the intra-operative position of the implant relative to a planned position of the implant according to a surgical plan; and displaying, via a display device, the comparison image for viewing of the intra-operative position of the implant relative to the planned position of the implant.

24. The computer-implemented method of example 23, further comprising:

determining positional information for repositioning of the implant to position the implant at a target position according to the surgical plan; and annotating the comparison image with the positional information.

25. The computer-implemented method of any of examples 23-24, further comprising:

synchronizing planned position image data and the intra-operative image data; and generating the comparison image based on the synchronized planned position image data and the intra-operative image data.

26. A computer-implemented method for monitoring implant positioning, the method comprising:

obtaining intra-operative image data from one or more imaging devices during a surgical procedure;

determining whether the surgical procedure is proceeding according to a surgical plan for the procedure;

in response to determining the surgical procedure is not proceeding according to the surgical plan, generating a deviation from surgical plan annotation for positioning one or more items that have been inserted into a patient; and displaying, via a display, the deviation from surgical plan annotation for viewing by a user.

27. The computer-implemented method of example 26, further comprising displaying the surgical plan annotation overlaid onto an intra-operative image of the intra-operative image data, wherein the one or more items include one or more implants and/or surgical instruments.

28. The computer-implemented method of any of examples 26-27, further comprising displaying, via the display, a comparison image for viewing of an intra-operative position of implant relative to a planned position of the implant, wherein the deviation from surgical plan annotation includes one or more measurements, spacing indicators, or mis-positioning labels.

29. A computing system comprising:

one or more processors; and one or more memories storing instructions that, when executed by the one or more processors, cause the computing system to perform a process of any one of methods in examples 1-28.

30. A non-transitory computer-readable medium storing instructions that, when executed by a computing system, cause the computing system to perform operations of any one of methods in examples 1-28.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected," or "operably coupled," to each other to achieve the desired functionality, and any two components capable of being so associated can also be viewed as being "operably couplable" to each other to achieve the desired functionality. Specific examples of operably couplable include but are not limited to physically malleable and/or physically interacting components and/or wirelessly interactable and/or wirelessly interacting components and/or logically interacting and/or logically interactable components.

The embodiments, features, systems, devices, materials, methods and techniques described herein may, in some embodiments, be similar to any one or more of the embodiments, features, systems, devices, materials, methods and techniques described in the following:

U.S. application Ser. No. 16/048,167, filed on Jul. 27, 2017, titled "SYSTEMS AND METHODS FOR ASSISTING AND AUGMENTING SURGICAL PROCEDURES";

U.S. application Ser. No. 16/242,877, filed on Jan. 8, 2019, titled "SYSTEMS AND METHODS OF ASSISTING A SURGEON WITH SCREW PLACEMENT DURING SPINAL SURGERY";

U.S. application Ser. No. 16/207,116, filed on Dec. 1, 2018, titled "SYSTEMS AND METHODS FOR MULTI-PLANAR ORTHOPEDIC ALIGNMENT";

U.S. application Ser. No. 16/352,699, filed on Mar. 13, 2019, titled "SYSTEMS AND METHODS FOR ORTHOPEDIC IMPLANT FIXATION";

U.S. application Ser. No. 16/383,215, filed on Apr. 12, 2019, titled "SYSTEMS AND METHODS FOR ORTHOPEDIC IMPLANT FIXATION";

U.S. application Ser. No. 16/569,494, filed on Sep. 12, 2019, titled "SYSTEMS AND METHODS FOR ORTHOPEDIC IMPLANTS";

U.S. Application No. 62/773,127, filed on Nov. 29, 2018, titled "SYSTEMS AND METHODS FOR ORTHOPEDIC IMPLANTS";

U.S. Application No. 62/928,909, filed on Oct. 31, 2019, titled "SYSTEMS AND METHODS FOR DESIGNING ORTHOPEDIC IMPLANTS BASED ON TISSUE CHARACTERISTICS";

U.S. application Ser. No. 16/735,222 (now U.S. Pat. No. 10,902,944), filed Jan. 6, 2020, titled "PATIENT-SPECIFIC MEDICAL PROCEDURES AND DEVICES, AND ASSOCIATED SYSTEMS AND METHODS";

U.S. application Ser. No. 16/987,113, filed Aug. 6, 2020, titled "PATIENT-SPECIFIC ARTIFICIAL DISCS, IMPLANTS AND ASSOCIATED SYSTEMS AND METHODS";

U.S. application Ser. No. 16/990,810, filed Aug. 11, 2020, titled "LINKING PATIENT-SPECIFIC MEDICAL DEVICES WITH PATIENT-SPECIFIC DATA, AND ASSOCIATED SYSTEMS, DEVICES, AND METHODS";

U.S. application Ser. No. 17/085,564, filed Oct. 30, 2020, titled "SYSTEMS AND METHODS FOR DESIGNING ORTHOPEDIC IMPLANTS BASED ON TISSUE CHARACTERISTICS";

U.S. application Ser. No. 17/100,396, filed Nov. 20, 2020, titled "PATIENT-SPECIFIC VERTEBRAL IMPLANTS WITH POSITIONING FEATURES";

U.S. application Ser. No. 17/124,822, filed Dec. 17, 2020, titled "PATIENT-SPECIFIC MEDICAL PROCEDURES AND DEVICES, AND ASSOCIATED SYSTEMS AND METHODS";

U.S. application Ser. No. 17/868,729, filed Jul. 19, 2022, titled "SYSTEMS FOR PREDICTING INTRAOPERATIVE PATIENT MOBILITY AND IDENTIFYING MOBILITY-RELATED SURGICAL STEPS";

U.S. application Ser. No. 17/978,746, filed Nov. 1, 2022, titled "PATIENT-SPECIFIC SPINAL INSTRUMENTS FOR IMPLANTING IMPLANTS AND DECOMPRESSION PROCEDURES";

International Application No. PCT/US2021/012065, filed Jan. 4, 2021, titled "PATIENT-SPECIFIC MEDICAL PROCEDURES AND DEVICES, AND ASSOCIATED SYSTEMS AND METHODS";

International Patent Application No. PCT/US22/48729, filed Nov. 2, 2022, titled "PATIENT-SPECIFIC ARTHROPLASTY DEVICES AND ASSOCIATED SYSTEMS AND METHODS";

U.S. application Ser. No. 18/113,573, filed Feb. 23, 2023, titled "PATIENT-SPECIFIC IMPLANT DESIGN AND MANUFACTURING SYSTEM WITH A DIGITAL FILING CABINET MANAGER";

U.S. application Ser. No. 17/878,633, filed Aug. 1, 2022, titled "NON-FUNGIBLE TOKEN SYSTEMS AND METHODS FOR STORING AND ACCESSING HEALTHCARE DATA";

U.S. Pat. No. 11,806,241, issued Nov. 7, 2023, titled "SYSTEM FOR MANUFACTURING AND PRE-OPERATIVE INSPECTING OF PATIENT-SPECIFIC IMPLANTS";

U.S. application Ser. No. 18/120,979, filed Mar. 13, 2023, titled "MULTI-STAGE PATIENT-SPECIFIC SURGICAL PLANS AND SYSTEMS AND METHODS FOR CREATING AND IMPLEMENTING THE SAME";

U.S. application Ser. No. 18/455,881, filed Aug. 25, 2023, titled "SYSTEMS AND METHODS FOR GENERATING MULTIPLE PATIENT-SPECIFIC SURGICAL PLANS AND MANUFACTURING PATIENT-SPECIFIC IMPLANTS";

U.S. Pat. No. 11,793,577, issued Oct. 24, 2023, titled "TECHNIQUES TO MAP THREE-DIMENSIONAL HUMAN ANATOMY DATA TO TWO-DIMENSIONAL HUMAN ANATOMY DATA";

International Patent Application No. PCT/US22/48729, filed Nov. 2, 2022, titled "PATIENT-SPECIFIC ARTHROPLASTY DEVICES AND ASSOCIATED SYSTEMS AND METHODS";

U.S. application Ser. No. 18/113,573, filed Feb. 23, 2023, titled "PATIENT-SPECIFIC IMPLANT DESIGN AND MANUFACTURING SYSTEM WITH A DIGITAL FILING CABINET MANAGER";

U.S. application Ser. No. 17/878,633, filed Aug. 1, 2022, titled "NON-FUNGIBLE TOKEN SYSTEMS AND METHODS FOR STORING AND ACCESSING HEALTHCARE DATA";

U.S. Pat. No. 11,806,241, issued Nov. 7, 2023, titled "SYSTEM FOR MANUFACTURING AND PRE-OPERATIVE INSPECTING OF PATIENT-SPECIFIC IMPLANTS";

U.S. application Ser. No. 18/120,979, filed Mar. 13, 2023, titled "MULTI-STAGE PATIENT-SPECIFIC SURGICAL PLANS AND SYSTEMS AND METHODS FOR CREATING AND IMPLEMENTING THE SAME";

U.S. application Ser. No. 18/455,881, filed Aug. 25, 2023, titled "SYSTEMS AND METHODS FOR GENERAT- ING MULTIPLE PATIENT-SPECIFIC SURGICAL PLANS AND MANUFACTURING PATIENT-SPE-CIFIC IMPLANTS"; and U.S. Pat. No. 11,793,577, issued Oct. 24, 2023, titled "TECHNIQUES TO MAP THREE-DIMENSIONAL HUMAN ANATOMY DATA TO TWO-DIMENSIONAL HUMAN ANATOMY DATA."

All of the above-identified patents and applications are incorporated by reference in their entireties. In addition, the embodiments, features, systems, devices, materials, methods and techniques described herein may, in certain embodiments, be applied to or used in connection with any one or more of the embodiments, features, systems, devices, or other matter.

The ranges disclosed herein also encompass any and all overlap, sub-ranges, and combinations thereof. Language such as "up to," "at least," "greater than," "less than," "between," or the like includes the number recited. Numbers preceded by a term such as "approximately," "about," and "substantially" as used herein include the recited numbers (e.g., about 10%=10%), and also represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of the stated amount.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting.

What is claimed is:

1. A method comprising:
obtaining at least one image of an implant located in a patient;
obtaining a virtual anatomical model of the patient;
performing an anatomical alignment routine by
synchronizing virtual anatomical features of the virtual anatomical model with corresponding anatomical features in the at least one image,
comparing a position of the implant in the at least one image to a planned position of a virtual implant of the virtual anatomical model, wherein the comparison is based on the synchronized virtual anatomical features and the corresponding anatomical features, and
causing display, via a user interface, of a first annotation for positioning the implant at the planned position based on the comparison; and
repeating the anatomical alignment routine to determine the implant is positioned at an acceptable location in the patient based on the comparison, wherein the acceptable location is identified by a second annotation within the user interface and is within a maximum acceptable distance from a target location for the implant, wherein the first annotation is different from the second annotation.

2. The method of claim 1, wherein
the at least one image includes a fluoroscopic image,
the synchronizing includes manipulating the virtual anatomical model and/or the at least one image according to a best fit routine, and the anatomical alignment routine is repeated using images of the patient showing the implant at another location for achieving a planned anatomical alignment.

3. The method of claim 2, wherein synchronizing the virtual anatomical features with the corresponding anatomical features includes
manipulating the virtual anatomical model and/or the at least one image by at least one of
zooming,
stretching, or
rotating the virtual anatomical model to align the virtual anatomical features of the virtual anatomical model with the corresponding anatomical features in the at least one image.

4. The method of claim 1, wherein the anatomical alignment routine is performed to determine whether a new position of the implant is a new acceptable location.

5. The method of claim 1, further comprising using a trained machine learning engine to perform the anatomical alignment routine.

6. The method of claim 1, further comprising sequentially receiving additional images of the patient to repeatedly perform the anatomical alignment routine using a respective one of the additional images.

7. The method of claim 1, further comprising:
retrieving a patient-specific surgical plan for the patient;
generating instructions for moving the implant toward the target location in the patient-specific surgical plan; and
causing the instructions to be intra-operatively outputted to assist with repositioning of the implant.

8. The method of claim 1, wherein the first annotation includes one or more measurements of the comparison or a distance from a current position of the implant to the planned position.

9. The method of claim 1, wherein the second annotation includes a rectangular window that changes color.

10. A system comprising:
one or more processors; and
one or more memories storing instructions that, when executed by the one or more processors, cause the system to perform a process comprising:
obtaining at least one image of an implant located in a patient;
obtaining a virtual anatomical model of the patient;
performing an anatomical alignment routine by
synchronizing virtual anatomical features of the virtual anatomical model with corresponding anatomical features in the at least one image,
comparing a position of the implant in the at least one image to a planned position of a virtual implant of the virtual anatomical model, wherein the comparison is based on the synchronized virtual anatomical features and the corresponding anatomical features, and
causing display, via a user interface, of a first annotation for positioning the implant at the planned position based on the comparison; and
repeating the anatomical alignment routine to determine the implant is positioned at an acceptable location in the patient based on the comparison, wherein the acceptable location is identified by a second annotation within the user interface and is within a maximum acceptable distance from a target location for the implant, wherein the first annotation is different from the second annotation.

11. The system of claim 10, wherein the at least one image includes a fluoroscopic image, the synchronizing includes manipulating the virtual anatomical model and/or the at least one image according to a best fit routine, and the anatomical alignment routine is repeated using images of the patient showing the implant at another location for achieving a planned anatomical alignment.

12. The system of claim 11, wherein synchronizing the virtual anatomical features with the corresponding anatomical features includes manipulating the virtual anatomical model and/or the at least one image by at least one of zooming, stretching, or rotating the virtual anatomical model to align the virtual anatomical features of the virtual anatomical model with the corresponding anatomical features in the at least one image.

13. The system of claim 10, wherein the anatomical alignment routine is performed to determine whether a new position of the implant is a new acceptable location.

14. The system of claim 10, further comprising using a trained machine learning engine to perform the anatomical alignment routine.

15. The system of claim 10, wherein the process further comprises sequentially receiving additional images of the patient to repeatedly perform the anatomical alignment routine using a respective one of the additional images.

16. The system of claim 10, wherein the process further comprises:

retrieving a patient-specific surgical plan for the patient;

generating instructions for moving the implant toward the target location in the patient-specific surgical plan; and causing the instructions to be intra-operatively outputted to assist with repositioning of the implant.

17. A non-transitory computer-readable medium storing instructions that, when executed by a computing system, cause the computing system to perform operations comprising:

obtaining at least one image of an implant located in a patient;

obtaining a virtual anatomical model of the patient;

performing an anatomical alignment routine by synchronizing virtual anatomical features of the virtual anatomical model with corresponding anatomical features in the at least one image, comparing a position of the implant in the at least one image to a planned position of a virtual implant of the virtual anatomical model, wherein the comparison is based on the synchronized virtual anatomical features and the corresponding anatomical features, and causing display, via a user interface, of a first annotation for positioning the implant at the planned position based on the comparison; and repeating the anatomical alignment routine to determine the implant is positioned at an acceptable location in the patient based on the comparison, wherein the acceptable location is identified by a second annotation within the user interface and is within a maximum acceptable distance from a target location for the implant, wherein the first annotation is different from the second annotation.

18. The non-transitory computer-readable medium of claim 17, wherein the at least one image includes a fluoroscopic image, the synchronizing includes manipulating the virtual anatomical model and/or the at least one image according to a best fit routine, and the anatomical alignment routine is repeated using images of the patient showing the implant at another location for achieving a planned anatomical alignment.

19. The non-transitory computer-readable medium of claim 18, wherein synchronizing the virtual anatomical features with the corresponding anatomical features includes manipulating the virtual anatomical model and/or the at least one image by at least one of zooming, stretching, or rotating the virtual anatomical model to align the virtual anatomical features of the virtual anatomical model with the corresponding anatomical features in the at least one image.

20. The non-transitory computer-readable medium of claim 17, wherein the anatomical alignment routine is performed to determine whether a new position of the implant is a new acceptable location.

21. The non-transitory computer-readable medium of claim 17, wherein the operations further comprise using a trained machine learning engine to perform the anatomical alignment routine.

22. The non-transitory computer-readable medium of claim 17, wherein the operations further comprise sequentially receiving additional images of the patient to repeatedly perform the anatomical alignment routine using a respective one of the additional images.

23. The non-transitory computer-readable medium of claim 17, wherein the operations further comprise:

retrieving a patient-specific surgical plan for the patient;

generating instructions for moving the implant toward the target location in the patient-specific surgical plan; and causing the instructions to be intra-operatively outputted to assist with repositioning of the implant.

* * * * *